US008980442B2

(12) United States Patent
Yabunouchi et al.

(10) Patent No.: US 8,980,442 B2
(45) Date of Patent: Mar. 17, 2015

(54) AROMATIC AMINE DERIVATIVE AND ORGANIC ELECTROLUMINESCENT ELEMENT USING SAME

(75) Inventors: Nobuhiro Yabunouchi, Sodegaura (JP); Tomoki Kato, Chiba (JP); Takahiro Fujiyama, Yao (JP); Yoshiyuki Totani, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 551 days.

(21) Appl. No.: 13/257,358

(22) PCT Filed: Mar. 18, 2010

(86) PCT No.: PCT/JP2010/001956
§ 371 (c)(1),
(2), (4) Date: Sep. 19, 2011

(87) PCT Pub. No.: WO2010/106806
PCT Pub. Date: Sep. 23, 2010

(65) Prior Publication Data
US 2012/0012832 A1    Jan. 19, 2012

(30) Foreign Application Priority Data
Mar. 19, 2009    (JP) .................. 2009-068306

(51) Int. Cl.
H01L 51/54    (2006.01)
H01L 51/00    (2006.01)
C07C 211/61   (2006.01)
C09K 11/06    (2006.01)
H05B 33/10    (2006.01)
C09B 57/00    (2006.01)
H01L 51/50    (2006.01)

(52) U.S. Cl.
CPC ............ *H01L 51/006* (2013.01); *C07C 211/61* (2013.01); *C09K 11/06* (2013.01); *H05B 33/10* (2013.01); *C09B 57/00* (2013.01); *C09B 57/008* (2013.01); *C07C 2103/18* (2013.01); *C07C 2103/26* (2013.01); *C07C 2103/52* (2013.01); *C07C 2103/94* (2013.01); *C09K 2211/1007* (2013.01); *C09K 2211/1011* (2013.01); *H01L 51/0081* (2013.01); *H01L 51/5056* (2013.01); *Y10S 428/917* (2013.01)
USPC ........... 428/690; 428/917; 313/504; 313/505; 313/506; 257/40; 257/E51.05; 257/E51.026; 257/E51.032; 564/26; 564/426; 564/430; 564/432; 564/434; 564/18; 564/79; 564/81; 564/101

(58) Field of Classification Search
USPC .................. 428/690, 917; 313/504, 505, 506; 257/40, E51.05, E51.026, E51.032; 564/26, 426, 430, 432, 434; 546/18, 546/79, 81, 101
See application file for complete search history.

(56) References Cited

U.S. PATENT DOCUMENTS

| 4,720,432 | A | 1/1988 | VanSlyke et al. |
| 5,061,569 | A | 10/1991 | VanSlyke et al. |
| 5,510,218 | A | 4/1996 | Nakata et al. |
| 8,394,510 | B2 | 3/2013 | Mizuki et al. |
| 2002/0028329 | A1* | 3/2002 | Ise et al. ................ 428/336 |
| 2003/0087126 | A1 | 5/2003 | Ishida et al. |
| 2005/0074631 | A1 | 4/2005 | Ishida et al. |
| 2006/0154105 | A1* | 7/2006 | Yamamoto et al. ........... 428/690 |
| 2006/0166034 | A1* | 7/2006 | Saitoh et al. ................. 428/690 |
| 2008/0014464 | A1 | 1/2008 | Kawamura et al. |
| 2008/0124572 | A1 | 5/2008 | Mizuki et al. |
| 2008/0145708 | A1 | 6/2008 | Heil et al. |
| 2009/0066225 | A1 | 3/2009 | Kimura et al. |
| 2009/0261717 | A1 | 10/2009 | Buesing et al. |
| 2010/0001636 | A1 | 1/2010 | Yabunouchi |
| 2012/0161119 | A1 | 6/2012 | Yabunouchi |
| 2013/0187137 | A1 | 7/2013 | Mizuki et al. |
| 2014/0061630 | A1 | 3/2014 | Yabunouchi |

FOREIGN PATENT DOCUMENTS

| CN | 101142170 A | 3/2008 |
| CN | 101155895 A | 4/2008 |
| CN | 102046613 | 5/2011 |
| EP | 2 295 421 A1 | 3/2011 |

(Continued)

OTHER PUBLICATIONS

International Search Report (PCT/ISA/210) issued on Apr. 20, 2010, by Japanese Patent Office as the International Searching Authority for International Application No. PCT/JP2010/001956.
C.W. Tang et al., "Organic Electroluminescent Diodes", Appl. Phys. Lett., vol. 51, No. 12, Sep. 21, 1987, pp. 913-915.
Extended European Search Report dated May 14, 2013, issued by the European Patent Office in corresponding European Patent Application No. 10753302.8. (10 pages).

*Primary Examiner* — Gregory Clark
(74) *Attorney, Agent, or Firm* — Buchanan, Ingersoll & Rooney PC

(57) ABSTRACT

There are provided an aromatic monoamine derivative having a fluorene structure-containing organic group and an aromatic hydrocarbon group-containing organic group, and an organic electroluminescent element containing an organic thin film layer composed of a single layer or plural layers while including at least a light emitting layer, the organic thin film layer being between a cathode and an anode, wherein at least one layer of the organic thin film layer, particularly a hole transport layer, contains the aromatic amine derivative alone or as a component of a mixture. An organic electroluminescent element which maintains high luminous efficiency even if exposed to a high temperature environment, and has a low driving voltage and a long emission lifetime, and an aromatic amine derivative capable of realizing the organic electroluminescent element are provided.

4 Claims, No Drawings

(56) References Cited

FOREIGN PATENT DOCUMENTS

| | | |
|---|---|---|
| EP | 2 348 017 A1 | 7/2011 |
| JP | 7-072639 A | 3/1995 |
| JP | 11-144875 A | 5/1999 |
| JP | 2002-154993 A | 5/2002 |
| JP | 2003-261471 A | 9/2003 |
| JP | 2004-043349 A | 2/2004 |
| JP | 2004-091350 A | 3/2004 |
| WO | WO 02/14244 A1 | 2/2002 |
| WO | WO 2006/108497 A1 | 10/2006 |
| WO | WO 2007/086701 A1 | 8/2007 |
| WO | 2007148660 A1 | 12/2007 |
| WO | WO 2008/006449 A1 | 1/2008 |
| WO | 2008062636 A1 | 5/2008 |
| WO | 2009145016 A1 | 3/2009 |

* cited by examiner

AROMATIC AMINE DERIVATIVE AND ORGANIC ELECTROLUMINESCENT ELEMENT USING SAME

TECHNICAL FIELD

The present invention relates to an aromatic amine derivative and an organic electroluminescent (EL) element using the same. More particularly, the present invention relates to an aromatic amine derivative which has a particular structure and is asymmetric, and which, when used in a hole transporting material, enhances the efficiency, suppresses the crystallization of molecules, and also enhances the yield of the production of organic electroluminescent elements, thereby improving the service life of organic electroluminescent elements.

BACKGROUND ART

An organic electroluminescent element is a spontaneous light emitting element which utilizes the principle that when an electric field is applied, a fluorescent substance emits light by means of the recombination energy of holes injected from an anode and electrons injected from a cathode. Since the report by C. W. Tang, et al. of Eastman Kodak Company on a low voltage-driven organic electroluminescent element based on a laminated type element (see Non-Patent Document 1), research has been actively conducted on organic electroluminescent elements using organic materials as the constituent materials. Tang, et al. used tris(8-quinolinolato)aluminum in the light emitting layer, and a triphenyldiamine derivative in the hole transport layer. A laminated structure is advantageous in that the efficiency of hole injection into the light emitting layer may be increased, the efficiency for the generation of excitons that are generated by recombination may be increased by blocking electrons injected from the cathode, and the excitons generated in the light emitting layer may be trapped. As the element structure of organic electroluminescent elements such as in this example, a two-layered structure which includes a hole transport (injection) layer and an electron transport and light emitting layer, a three-layered structure which includes a hole transport (injection) layer, a light emitting layer and an electron transport (injection) layer, and the like are well known. In such elements having a laminated type structure, the element structure and the method for forming such a structure have been devised so as to increase the recombination efficiency of injected holes and electrons.

Generally, when an organic electroluminescent element is driven or stored in a high temperature environment, adverse effects occur, such as change in the emitted light color, a decrease in the luminous efficiency, an increase in the driving voltage, and shortening of the emission lifetime. In order to prevent these, it has been necessary to increase the glass transition temperature (Tg) of the hole transporting material. Accordingly, a hole transporting material needs to have many aromatic groups in the molecule (see, for example, Patent Documents 1 and 2: aromatic diamine derivatives of Patent Document 1, and aromatic fused-ring diamine derivatives of Patent Document 2), and conventionally, structures each having 8 to 12 benzene rings have been used with preference.

However, if a substance has a large number of aromatic groups in the molecule, crystallization is prone to occur when a thin film is formed using such a hole transporting material, and an organic electroluminescent element is produced using the thin film. Also, there are problems that the outlet of the crucible used in vapor deposition is blocked, defects attributable to crystallization occur in the thin film, or a decrease in the yield of the organic electroluminescent element may occur. Furthermore, a compound having a large number of aromatic groups in the molecule generally has a high glass transition temperature (Tg); however, such a compound has problems that the sublimation temperature is high, and the service life is short because decomposition at the time of deposition, or an occurrence in which deposition is non-uniformly formed is believed to occur.

Meanwhile, monoamine derivatives having fluorene with aryl groups have been disclosed (see Patent Documents 3 to 8). Patent Document 3 is a patent document related to a photoreceptor. Patent Documents 4 to 8 are patent documents related to organic EL. Particularly, patent document 8 describes an example of using a fluorene-containing monoamine compound in the hole injection/transport layer of an organic electroluminescent element, but a further enhancement of performance is desired.

As discussed above, there have been reports on high-efficiency, long-life organic electroluminescent elements, but there has been a strong demand for an organic electroluminescent element having superior performance.

Patent Document 1: U.S. Pat. No. 4,720,432
Patent Document 2: U.S. Pat. No. 5,061,569
Patent Document 3: Japanese Patent Application Laid-Open No. 7-72639
Patent Document 4: Japanese Patent Application Laid-Open No. 2002-154993
Patent Document 5: Japanese Patent Application Laid-Open No. 2004-043349
Patent Document 6: Japanese Patent Application Laid-Open No. 2003-261471
Patent Document 7: Japanese Patent Application Laid-Open No. 2004-91350
Patent Document 8: Japanese Patent Application Laid-Open No. 11-144875
Non-Patent Document 1: C. W. Tang, S. A. Vanslyke, Applied Physics Letters, Vol. 51, p. 913 (1987)

DISCLOSURE OF INVENTION

Problems to be Solved by the Invention

The present invention was made in order to solve the problems described above, and an object of the present invention is to provide an organic electroluminescent element which maintains high luminous efficiency even when exposed to a high temperature environment, has a low driving voltage, and has a long emission lifetime, and an aromatic amine derivative capable of realizing the organic electroluminescent element.

Means for Solving the Problem

The inventors of the present invention have conducted a thorough investigation in order to achieve the object described above, and as a result, they provide a novel aromatic amine derivative having a particular structure. Furthermore, the inventors found that when this aromatic amine derivative is used in an organic electroluminescent element having an organic thin film layer which is composed of a single layer or plural layers while including at least a light emitting layer, and is interposed between a cathode and an anode, such that the aromatic amine derivative is incorporated alone or as a component of a mixture into at least one layer (particularly, a hole transport layer) of the organic thin film layer, a suitable organic electroluminescent element is obtained. Thus, the inventors completed the present invention. That is, a first aspect of the present invention relates to an aromatic amine derivative shown below.

<1> An aromatic amine derivative represented by the following formula (1).

[Chemical formula 1]

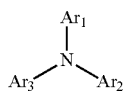

(1)

In the formula (1), $Ar_1$ represents an organic group A represented by the following formula (2) or (2-2); $Ar_2$ represents the organic group A, or an organic group B represented by the following formula (3); $Ar_3$ represents the organic group A, the organic group B, or an organic group C represented by the following formula (3-2). When two or more of $Ar_1$ to $Ar_3$ each represent the organic group A, the two or more organic groups A may be identical or different; when two of $Ar_1$ to $Ar_3$ each represent the organic group B, the two organic groups B may be identical or different.

[Chemical formula 2]

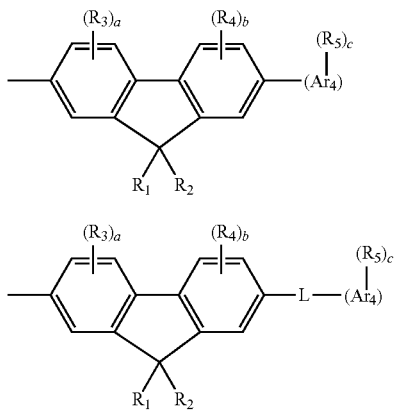

In the formulas (2) and (2-2), $Ar_4$ represents a substituted or unsubstituted fused-ring group having 10 to 14 ring-forming carbon atoms. $R_1$ to $R_5$ each independently represent a hydrogen atom, a linear, branched or cyclic alkyl group having 1 to 10 carbon atoms, or an aryl group having 6 to 12 ring-forming carbon atoms. a, b and c each independently represent an integer from 0 to 2; two of $R_3$, $R_4$, and $R_5$ may be joined together to form a saturated ring structure. When a, b or c is 2, $R_3$ and $R_3$, $R_4$ and $R_4$, or $R_5$ and $R_5$ may be respectively joined together to form a saturated ring structure. Further, in the formula (2-2), L represents a substituted or unsubstituted arylene group having 6 to 10 ring-forming carbon atoms.

[Chemical formula 3]

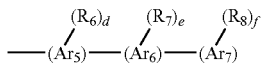

(3)

In the formula (3), $Ar_5$ and $Ar_6$ each independently represent a substituted or unsubstituted arylene group having 6 to 14 ring-forming carbon atoms. $Ar_7$ represents a single bond, or a substituted or unsubstituted arylene group having 6 to 14 ring-forming carbon atoms. $R_6$ to $R_8$ each independently represent a hydrogen atom, a linear, branched or cyclic alkyl group having 1 to 10 carbon atoms, or an aryl group having 6 to 12 ring-forming carbon atoms. d, e and f each independently represent an integer from 0 to 2; two of $R_6$, $R_7$ and $R_8$ may be joined together to form a saturated ring structure. Further, when d, e or f is 2, $R_6$ and $R_6$, $R_7$ and $R_7$, or $R_8$ and $R_8$ may be respectively joined together to form an unsaturated ring structure.

[Chemical formula 4]

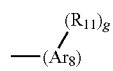

(3-2)

In the formula (3-2), $Ar_8$ represents a substituted or unsubstituted arylene group having 10 to 14 ring-forming carbon atoms. $R_{11}$ represents a hydrogen atom, a linear, branched or cyclic alkyl group having 1 to 10 carbon atoms, or an aryl group having 6 to 12 ring-forming carbon atoms; and g represents an integer from 0 to 2.

<2> The aromatic amine derivative as set forth in item <1>, wherein the organic group B is represented by the following formula (4).

[Chemical formula 5]

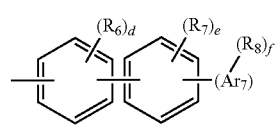

(4)

In the formula (4), $Ar_7$ represents a single bond, or a substituted or unsubstituted arylene group having 6 to 14 ring-forming carbon atoms. $R_6$ to $R_8$ each independently represent a hydrogen atom, a linear, branched or cyclic alkyl group having 1 to 10 carbon atoms, or an aryl group having 6 to 12 ring-forming carbon atoms. d, e and f each independently represent an integer from 0 to 2. Two of $R_6$, $R_7$ and $R_8$ may be joined together to form a saturated ring structure. Further, when d, e or f is 2, $R_6$ and $R_6$, $R_7$ and $R_7$, or $R_8$ and $R_8$ may be respectively joined together to form an unsaturated ring structure.

<3> The aromatic amine derivative as set forth in item <2>, wherein the organic group B is represented by any one of the following formulas (5) to (7).

[Chemical formula 6]

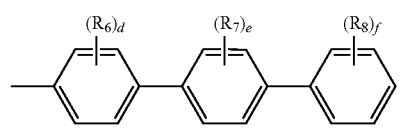

(5)

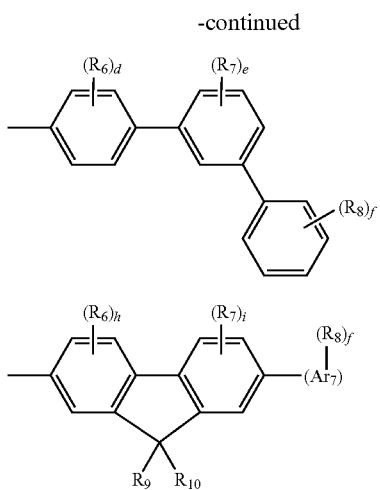

In the formula (7), $Ar_7$ represents a single bond, or a substituted or unsubstituted arylene group having 6 to 14 ring-forming carbon atoms. $R_6$ to $R_8$ each independently represent a hydrogen atom, a linear, branched or cyclic alkyl group having 1 to 10 carbon atoms, or an aryl group having 6 to 12 ring-forming carbon atoms. $R_9$ and $R_{10}$ each independently represent a linear, branched or cyclic alkyl group having 1 to 10 carbon atoms, or an aryl group having 6 to 12 ring-forming carbon atoms; d, e and f in the formulas (5) to (7) each independently represent an integer from 0 to 2. Further, h and i in the formula (7) each independently represent 0 or 1. Two of $R_6$, $R_7$ and $R_8$ may be joined together to form a saturated ring structure. Further, when d, e or f in the formulas (5) to (7) is 2, and when h or i in the formula (7) is 1 while f is 2, $R_6$ and $R_6$, $R_7$ and $R_7$, or $R_8$ and $R_8$ may be respectively joined together to form an unsaturated ring structure.

<4> The aromatic amine derivative as set forth in item <3>, wherein $Ar_1$ and $Ar_2$ each represent the organic group A, and $Ar_3$ represents the organic group B represented by any one of the formulas (5) to (7).

<5> The aromatic amine derivative as set forth in item <3>, wherein $Ar_1$ represents the organic group A, and $Ar_2$ and $Ar_3$ each independently represent the organic group B represented by any one of the formulas (5) to (7).

<6> The aromatic amine derivative as set forth in item <1>, wherein $Ar_1$ to $Ar_3$ each independently represent the organic group A.

<7> The aromatic amine derivative as set forth in item <1>, which is a material for use in organic electroluminescent elements.

<8> The aromatic amine derivative as set forth in item <1>, which is a hole transporting material or a hole injecting material for use in organic electroluminescent elements.

A second aspect of the present invention relates to an organic electroluminescent element shown below.

<9> An organic electroluminescent element containing an organic thin film layer composed of a single layer or plural layers while including at least a light emitting layer, the organic thin film layer being between a cathode and an anode, wherein at least one layer of the organic thin film layer contains the aromatic amine derivative as set forth in item <1> or mixture thereof.

<10> The organic electroluminescent element as set forth in item <9>, wherein the organic thin film layer contains a hole transport layer, and the aromatic amine derivative is contained in the hole transport layer.

<11> The organic electroluminescent element as set forth in item <9>, wherein the organic thin film layer contains plural hole transport layers, and the aromatic amine derivative is contained in the layer which is in direct contact with the light emitting layer.

<12> The organic electroluminescent element as set forth in item <9>, wherein the organic thin film layer contains a hole injection layer, and the aromatic amine derivative is contained in the hole injection layer.

<13> The organic electroluminescent element as set forth in item <9>, wherein the organic thin film layer contains plural hole injection layers, and the aromatic amine derivative is contained in the layer which is in direct contact with the anode.

<14> An organic electroluminescent element containing an organic thin film layer composed of a single layer or plural layers while including at least a light emitting layer, the organic thin film layer being between a cathode and an anode, wherein the organic thin film layer contains a hole transport layer, and the aromatic amine derivative element as set forth in item <4> or <5> is contained in the hole transport layer.

<15> An organic electroluminescent element containing an organic thin film layer composed of a single layer or plural layers while including at least a light emitting layer, the organic thin film layer being between a cathode and an anode, wherein the organic thin film layer contains a hole injection layer, and the aromatic amine derivative as set forth in item <4> or <6> is contained in the hole injection layer.

<16> An organic electroluminescent element containing an organic thin film layer composed of a single layer or plural layers while including at least a light emitting layer, the organic thin film layer being between a cathode and an anode, wherein the organic thin film layer contains a hole transport layer and a hole injection layer, and the aromatic amine derivative as set forth in item <4> is respectively contained in the hole transport layer and the hole injection layer.

<17> An organic electroluminescent element, containing an organic thin film layer composed of a single layer or plural layers while including at least a light emitting layer, the organic thin film layer being between a cathode and an anode, wherein the organic thin film layer contains a hole transport layer and a hole injection layer, the aromatic amine derivative as set forth in item <4> is contained in the hole transport layer, and the aromatic amine derivative as set forth in item <6> is contained in the hole injection layer.

<18> An organic electroluminescent element containing an organic thin film layer composed of a single layer or plural layers while including at least a light emitting layer, the organic thin film layer being between a cathode and an anode, wherein the organic thin film layer contains a hole transport layer and a hole injection layer, the aromatic amine derivative as set forth in item <5> is contained in the hole transport layer, and the aromatic amine derivative as set forth in item <4> is contained in the hole injection layer.

<19> An organic electroluminescent element containing an organic thin film layer composed of a single layer or plural layers while including at least a light emitting layer, the organic thin film layer being between a cathode and an anode, wherein the organic thin film layer contains a hole transport layer and a hole injection layer, the aromatic amine derivative as set forth in item <5> is contained in the hole transport layer, and the aromatic amine derivative as set forth in item <6> is contained in the hole injection layer.

<20> An organic electroluminescent element containing an organic thin film layer composed of a single layer or plural layers while including at least a light emitting layer, the organic thin film layer being between a cathode and an anode, wherein the organic thin film layer is a single layer serving as a hole transport layer and a hole injection layer, and the aromatic amine derivative as set forth in any one of items <4> to <6> is contained in the organic thin film layer.

<21> The organic electroluminescent element as set forth in item <9>, wherein a styrylamine compound and/or an arylamine compound is contained in the light emitting layer.

<22> The organic electroluminescent element as set forth in item <9>, wherein the organic thin film layer contains plural hole transport layers and hole injection layers, and at least one layer among the hole transport layers and the hole injection layers is a layer containing an acceptor material.

Advantageous Effects of Invention

When the aromatic amine derivative according to the present invention is used, an organic electroluminescent element which maintains high luminous efficiency even if exposed to a high temperature environment, and has a low driving voltage and a long emission lifetime, is obtained.

BEST MODE FOR CARRYING OUT THE INVENTION

In the formula (1), $Ar_1$ represents an organic group A represented by the following formula (2) or (2-2). $Ar_2$ represents the organic group A, or an organic group B represented by the following formula (3). Furthermore, $Ar_3$ represents the organic group A, the organic group B, or an organic group C represented by the following formula (3-2). In addition, at least one of $Ar_1$ to $Ar_3$ represents the organic group A. When two or more of $Ar_1$ to $Ar_3$ respectively represent the organic group A, the two or more organic groups A may be identical or different. Similarly, when two of $Ar_1$ to $Ar_3$ respectively represent the organic group B, the two organic groups B may be identical or different.

[Chemical formula 7]

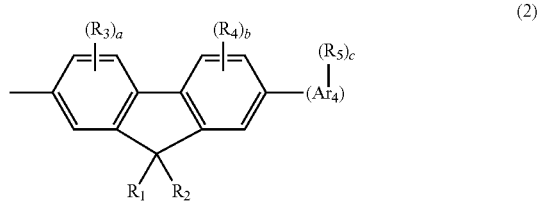

(2)

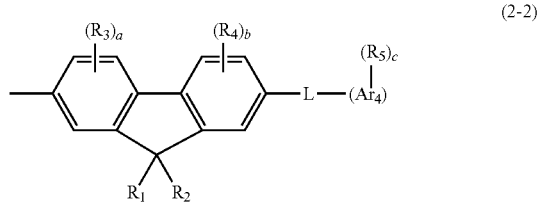

(2-2)

[Chemical formula 8]

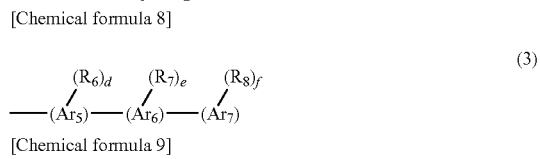

(3)

[Chemical formula 9]

(3-2)

In the formula (2), $R_1$ to $R_5$ each independently represent a linear, branched or cyclic alkyl group having 1 to 10 carbon atoms (preferably 1 to 5 carbon atoms), or an aryl group having 6 to 12 ring-forming carbon atoms.

Specific examples of the alkyl group represented by $R_1$ to $R_5$ include a methyl group, an ethyl group, an isopropyl group, an n-propyl group, an s-butyl group, a t-butyl group, a pentyl group, a hexyl group, a cyclopropyl group, a cyclobutyl group, a cyclopentyl group, a cyclohexyl group, and the like. Specific examples of the aryl group represented by $R_1$ to $R_5$ include a phenyl group, a naphthyl group, a biphenyl group, and the like.

Two of $R_3$, $R_4$, and $R_5$ may be joined together to form a saturated ring structure, and the saturated ring structure may be a 5-membered or 6-membered saturated ring structure.

In the formula (2), $Ar_4$ represents a substituted or unsubstituted fused-ring group having 10 to 14 ring-forming carbon atoms. Specific examples thereof include a 1-naphthyl group, a 2-naphthyl group, a 1-phenanthryl group, a 2-phenanthryl group, a 3-phenanthryl group, a 9-phenanthryl group, and the like.

In the formula (2), a, b and c each represent an integer from 0 to 2. When a, b or c is 2, $R_3$ and $R_3$, $R_4$ and $R_4$, or $R_5$ and $R_5$ may be respectively joined together to form an unsaturated ring structure. The unsaturated ring may be a 5-membered ring, a 6-membered ring, or the like.

In the formula (2-2), L represents a substituted or unsubstituted arylene group having 6 to 10 ring-forming carbon atoms. Examples of the arylene group represented by L include divalent groups such as a phenylene group and a naphthalenediyl group.

In the formula (3), $Ar_5$ to $Ar_7$ each independently represent a substituted or unsubstituted arylene group having 6 to 14 ring-forming carbon atoms. Examples of the arylene group represented by $Ar_5$ to $Ar_7$ include divalent groups such as a phenylene group, a naphthalenediyl group, a biphenylene group, and a phenanthrenediyl group.

In the formula (3), $R_6$ to $R_8$ each independently represent a hydrogen atom, a linear, branched or cyclic alkyl group having 1 to 10 carbon atoms, or an aryl group having 6 to 12 ring-forming carbon atoms. Specific examples thereof include the same groups as listed for $R_1$ to $R_5$. The saturated ring structure formed by $R_6$ to $R_8$ joining together may be a 5-membered or 6-membered saturated ring structure.

In the formula (3), d, e and f each represent an integer from 0 to 2. When d, e or f is 2, $R_6$ and $R_6$, $R_7$ and $R_7$, or $R_8$ and $R_8$ may be joined together to form an unsaturated ring structure. The unsaturated ring may be a 5-membered ring, a 6-membered ring, or the like.

In the formula (3-2), $Ar_8$ represents a substituted or unsubstituted arylene group having 10 to 14 ring-forming carbon atoms. Examples of the arylene group represented by $Ar_8$ include divalent groups such as a naphthalenediyl group and a phenanthrenediyl group.

In the formula (3-2), $R_{11}$ represents a hydrogen atom, a linear, branched or cyclic alkyl group having 1 to 10 carbon atoms, or an aryl group having 6 to 12 ring-forming carbon atoms. Specific examples of the alkyl group and aryl group represented by $R_{11}$ respectively include the same groups as listed above for $R_1$ to $R_5$. Furthermore, g in the formula (3-2) represents an integer from 0 to 2.

The organic group B represented by the formula (3) is preferably represented by the following formula (4).

[Chemical formula 10]

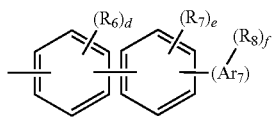

(4)

In the formula (4), $Ar_7$ represents a single bond, or a substituted or unsubstituted arylene group having 6 to 14 ring-forming carbon atoms. $R_6$ to $R_8$ each independently represent a hydrogen atom, a linear, branched or cyclic alkyl group having 1 to 10 carbon atoms, or an aryl group having 6 to 12 ring-forming carbon atoms. d, e and f each independently represent an integer from 0 to 2. Two of $R_6$, $R_7$ and $R_8$ may be joined together to form a saturated ring structure. Furthermore, when d, e or f is 2, $R_6$ and $R_6$, $R_7$ and $R_7$, or $R_8$ and $R_8$ may be joined together to form an unsaturated ring structure.

Furthermore, the organic group B represented by the formula (4) is preferably represented by any one of the following formulas (5) to (7):

[Chemical formula 11]

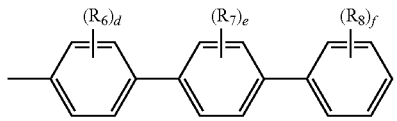

(5)

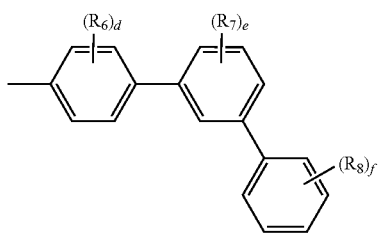

(6)

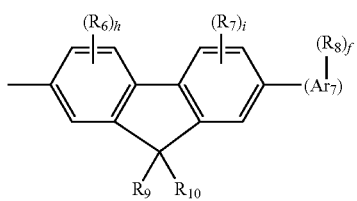

(7)

In the formula (7), $R_9$ and $R_{10}$ each independently represent a linear, branched or cyclic alkyl group having 1 to 10 carbon atoms, or an aryl group having 6 to 12 ring-forming carbon atoms. Specific examples thereof include the same groups as listed above for $R_1$ to $R_5$.

The aromatic amine derivative represented by formula (1) of the present invention is preferably such that $Ar_1$ and $Ar_2$ are each the organic group A, and $Ar_3$ is the organic group B represented by any one of the formulas (5) to (7); such that $Ar_1$ is the organic group A, and $Ar_2$ and $Ar_3$ are each independently represent the organic group B represented by any one of the formulas (5) to (7); or such that $Ar_1$ to $Ar_3$ are each independently the organic group A.

The aromatic amine derivative represented by formula (1) of the present invention can be synthesized by, for example, the following reaction.

First, an intermediate X (halogen compound) is synthesized. The intermediate X serves as the origin of the organic group A represented by formula (2) or the organic group B represented by formula (3). For example, 1-naphthylboronic acid and 4-iodo-1-bromo(9,9-dimethyl)fluorene are allowed to react at room temperature to 150° C. in an aqueous solution containing a solvent [for example, toluene] and a base [for example, sodium carbonate] in the presence of a catalyst [for example, tetrakis(triphenylphosphine)palladium(0)], and thereby the intermediate X is obtained. The reaction is preferably carried out in an inert gas atmosphere such as in argon.

[Chemical formula 12]

$Ar_1$—X (X is a halogen)          Intermediate X

Separately, an intermediate Y (amine compound) is synthesized. The intermediate Y serves as the origin of the organic group B represented by formula (3) or the organic group A represented by formula (2). A halide [for example, 4-bromo-p-terphenyl] and a compound capable of generating an amino group (may include a compound that generates a substituted or unsubstituted aryl group having 6 to 30 ring-forming carbon atoms) [for example, benzamide] are allowed to react at 50° C. to 250° C. in a solvent [for example, xylene], in the presence of a catalyst [a metal halide such as copper iodide, and an amine such as N,N'-dimethylethylenediamine] and a base [for example, potassium carbonate]. Thereafter, the compounds are allowed to react at 50° C. to 250° C. in a solvent [for example, xylene], in the presence of a base [for example, potassium hydroxide] and water, and thereby an intermediate Y is obtained. The reaction is preferably carried out in an inert gas atmosphere such as in argon.

[Chemical formula 13]

$Ar_2Ar_3N$—H          Intermediate Y

Subsequently, the intermediate X and the intermediate Y are allowed to react at 0° to 150° C. in a solvent [for example, dry toluene], in the presence of a catalyst [for example, tris(dibenzylideneacetone)dipalladium(0)] and a base [for example, t-butoxysodium], and thereby, the aromatic amine derivative of the present invention can be synthesized. The reaction is preferably carried out in an inert gas atmosphere such as in argon.

After completion of the reaction, the reaction product is cooled to room temperature, water is added thereto, and the reaction product is filtered. The filtrate is extracted with a solvent such as toluene, and the extract is dried over a drying agent such as anhydrous magnesium sulfate. The dried resultant is desolvated and concentrated under reduced pressure. The obtained crude product was purified with a column and is recrystallized from a solvent such as toluene. The crystals are separated by filtration and dried, and the aromatic amine derivative of the present invention is obtained in a purified form.

A halide of the organic group A and a halide of the organic group B can be introduced into any intermediate Y. Also, one or two aryl groups can be introduced, and the aryl groups can be introduced in any combination. When an amine compound (intermediate Y) obtained as a result of the introduction is allowed to react with any halide (intermediate X) in the same manner as in the technique described above, the target product can be obtained. The reaction procedure or combination method of these processes can be carried out in consideration of reactivity, ease of purification, and the like.

Representative examples of the aromatic amine derivative represented by formula (1) of the present invention will be shown below, but the aromatic amine derivative of the present invention is not intended to be limited to these representative examples.

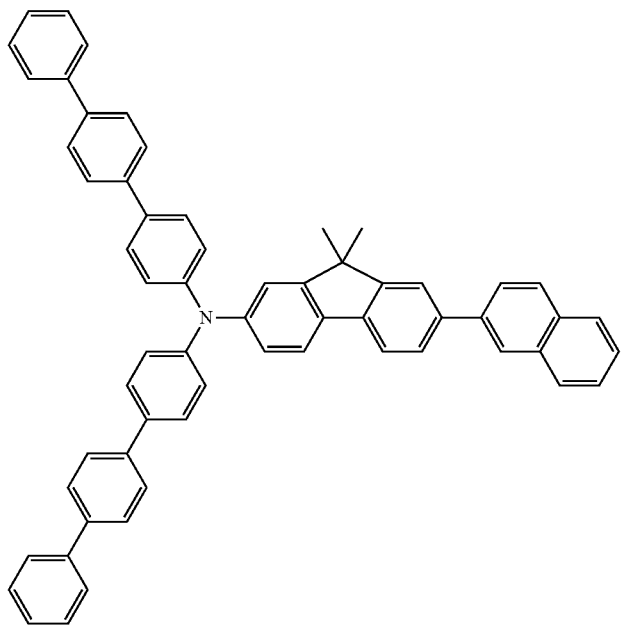
[Chemical formula 14]
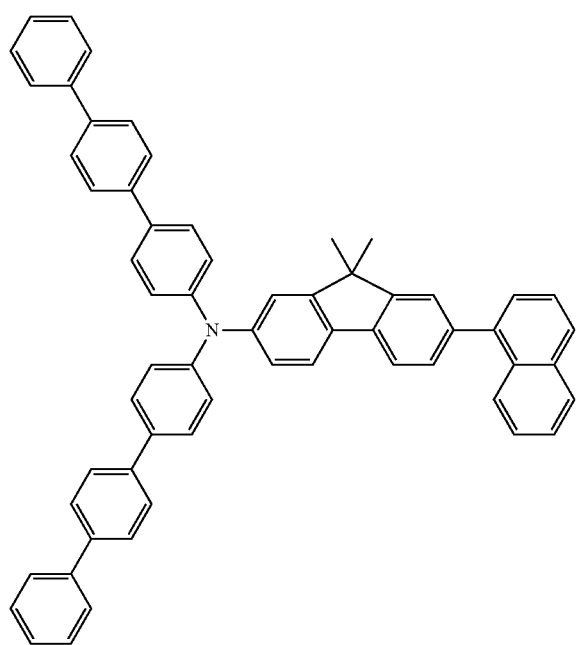

-continued
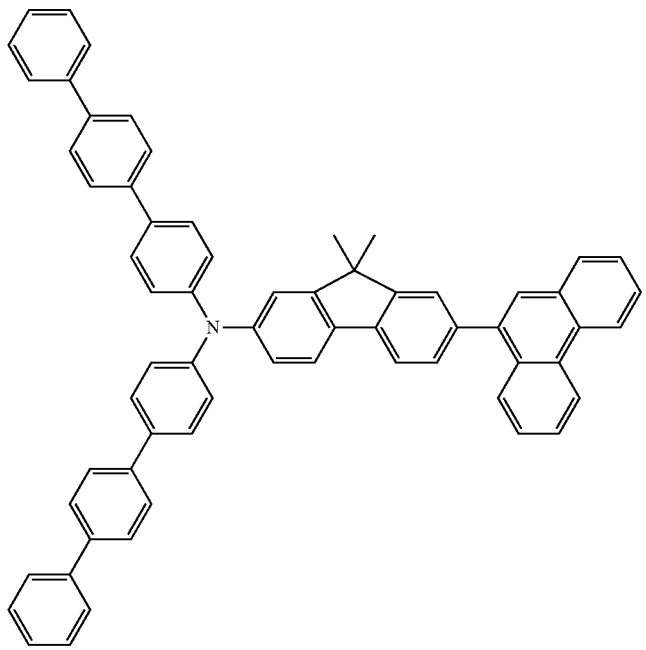
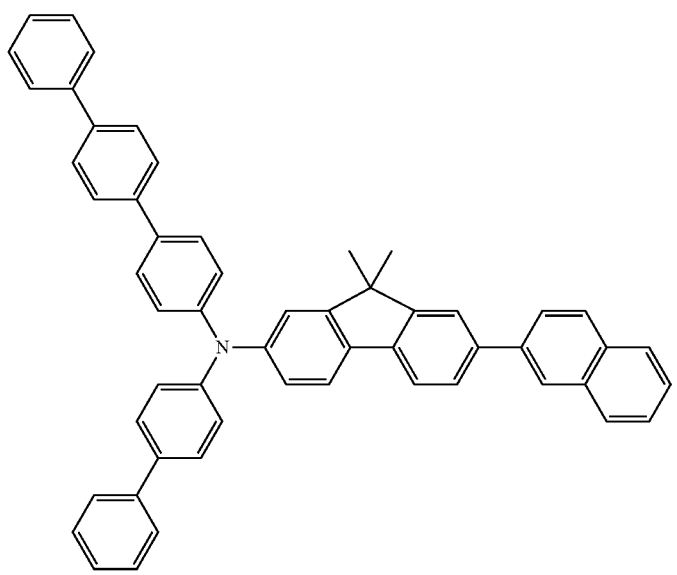

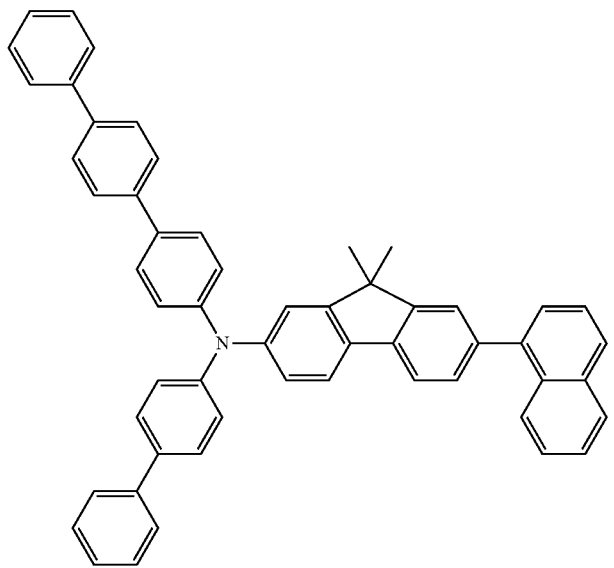
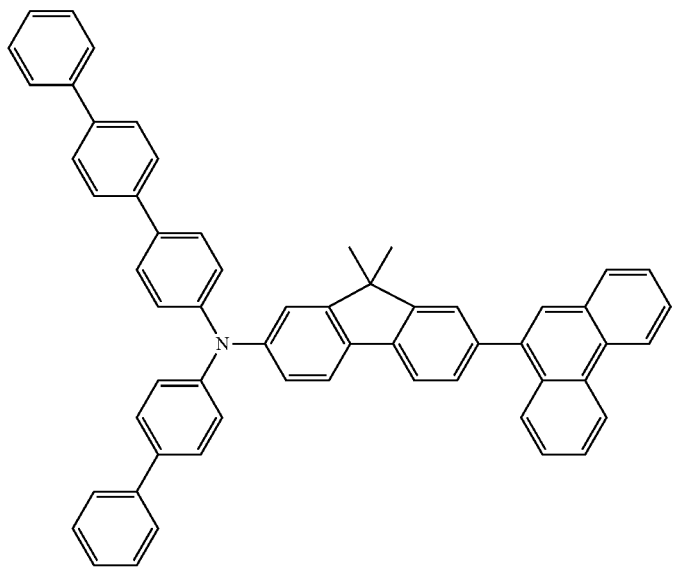
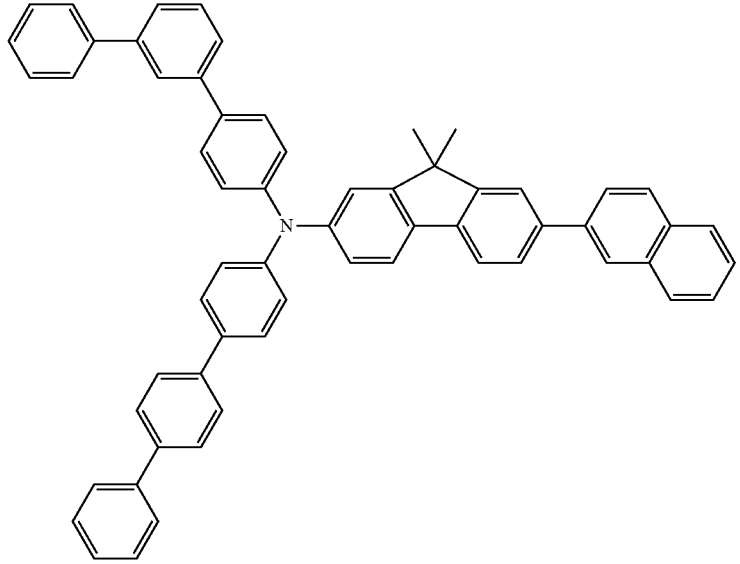

-continued
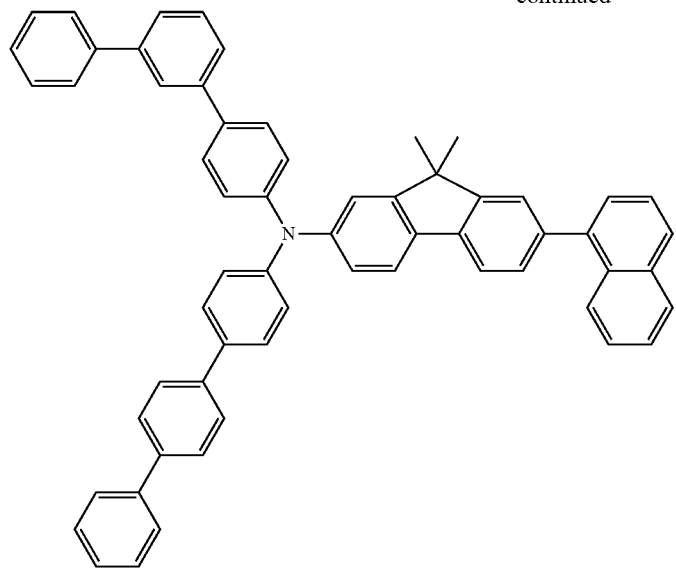
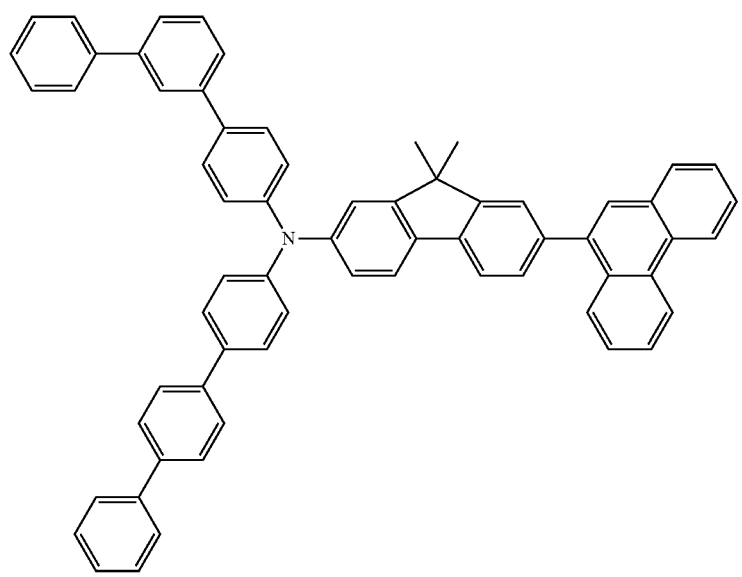
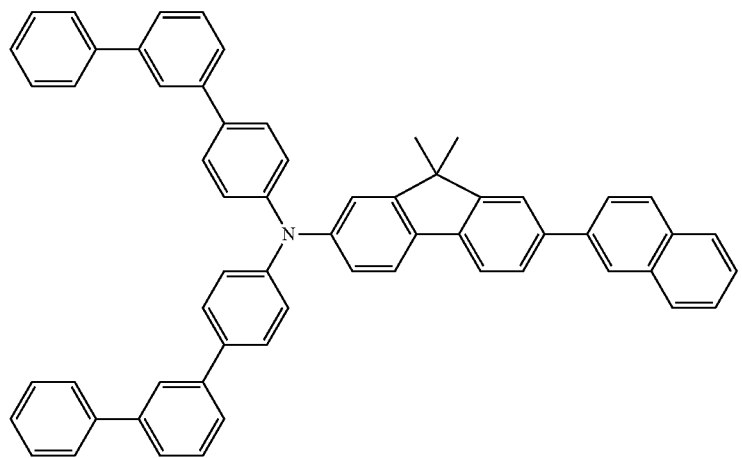

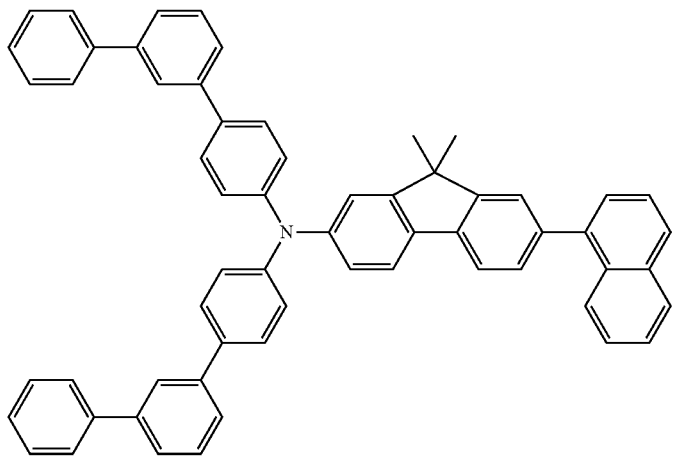
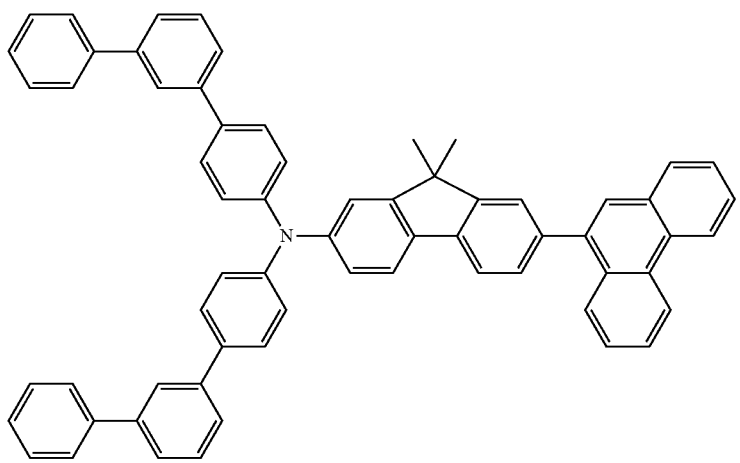
[Chemical formula 15]
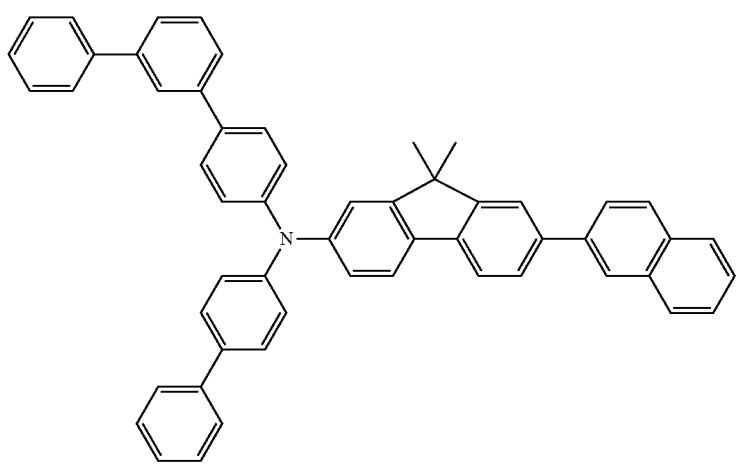

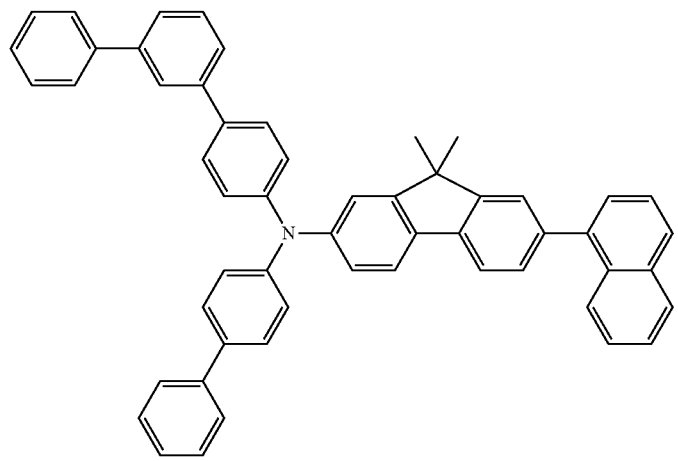
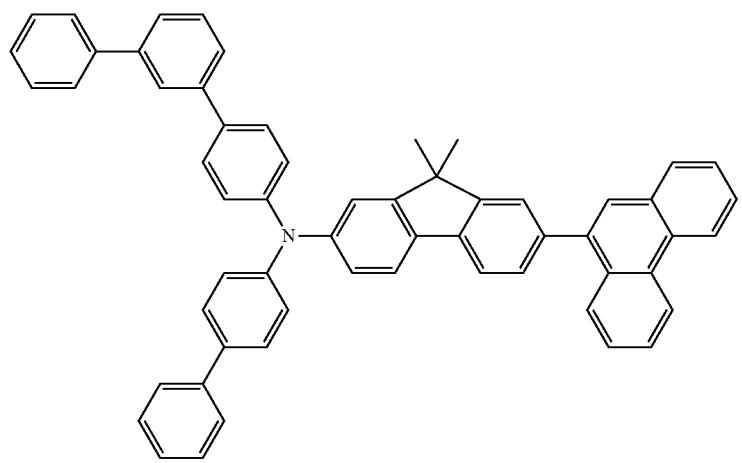
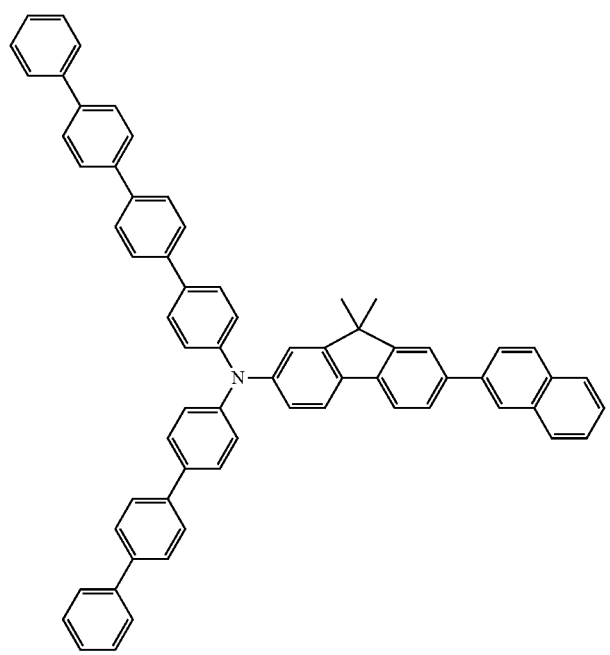

-continued
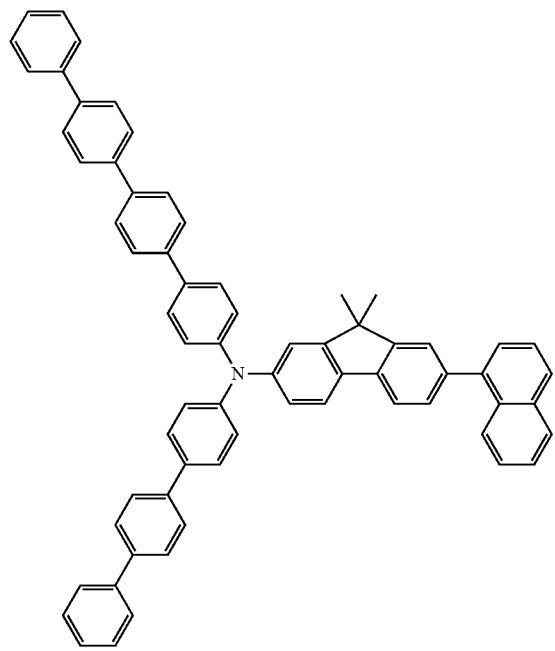
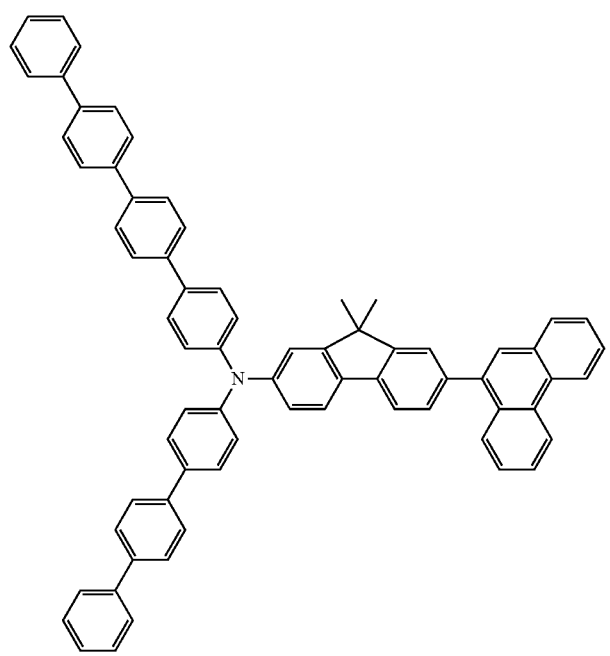

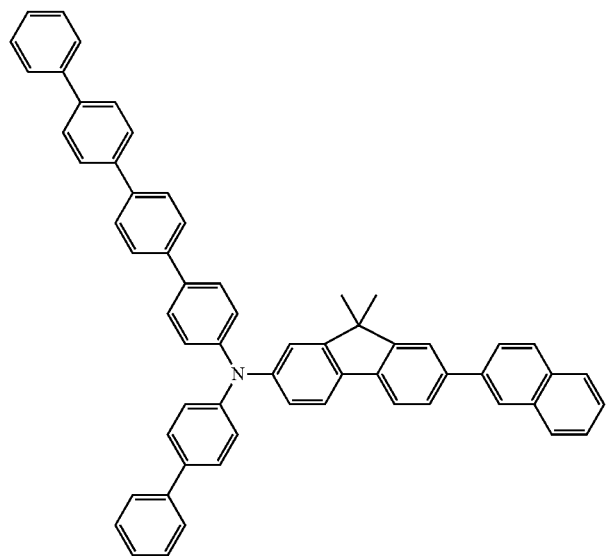
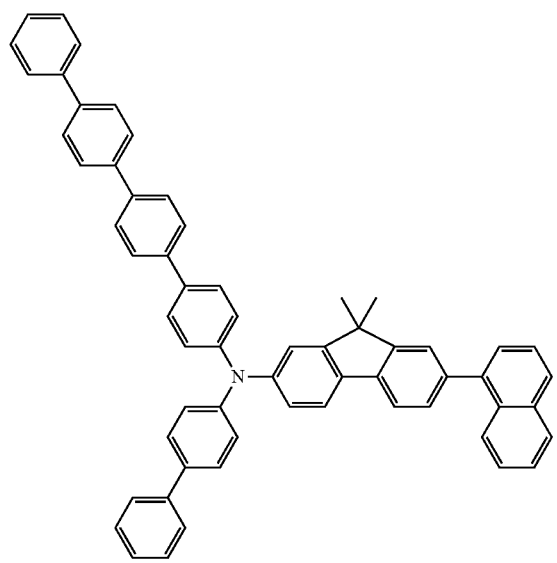

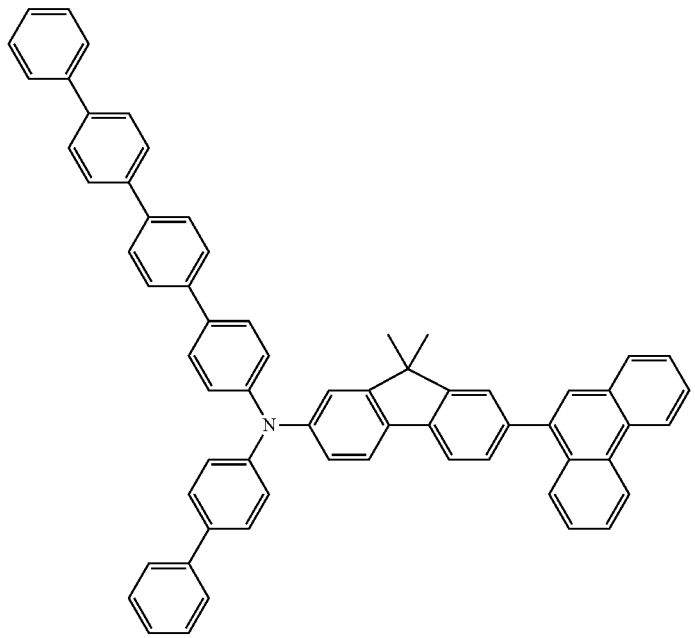
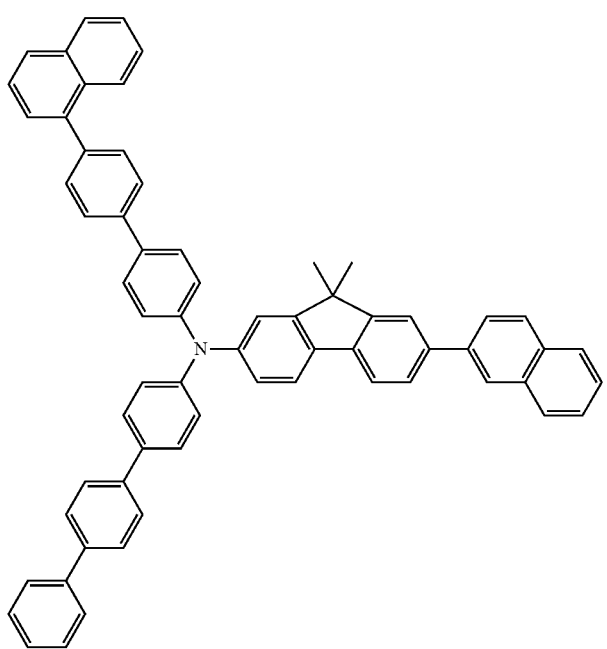

-continued
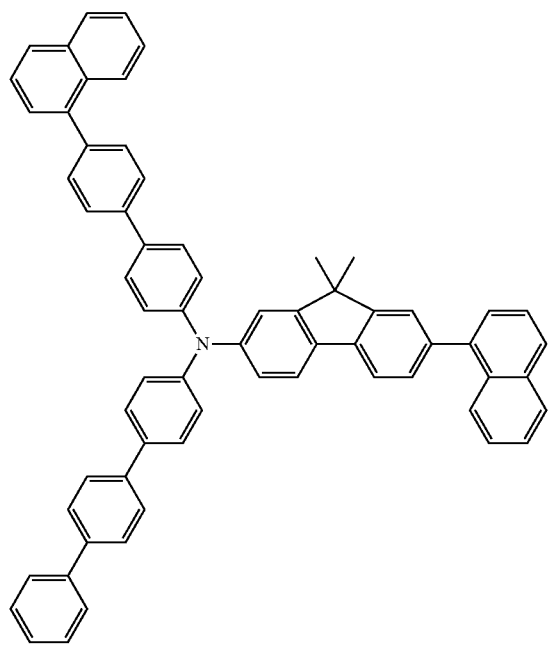
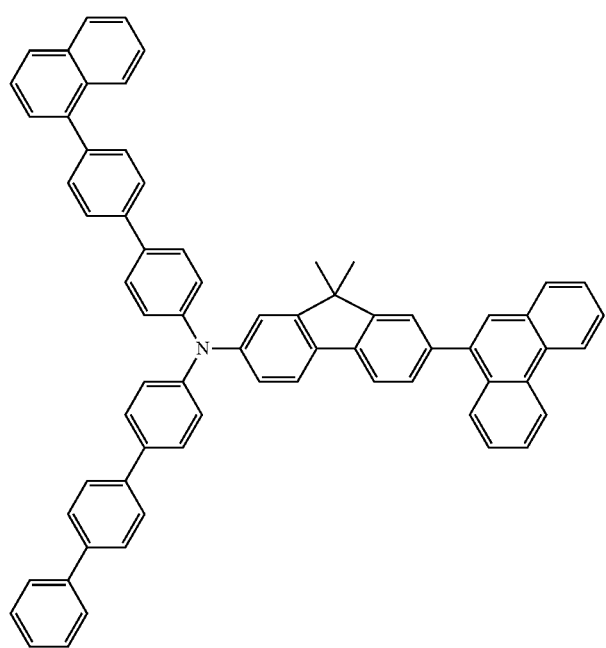

-continued
[Chemical formula 16]
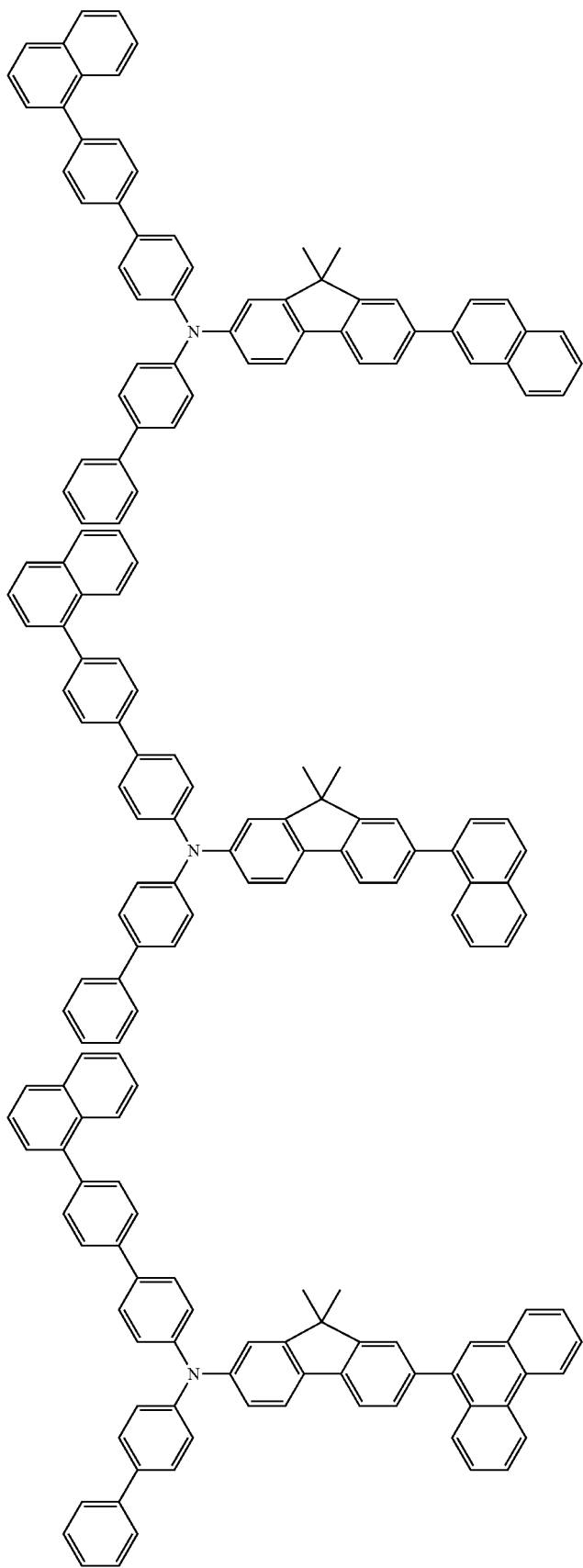

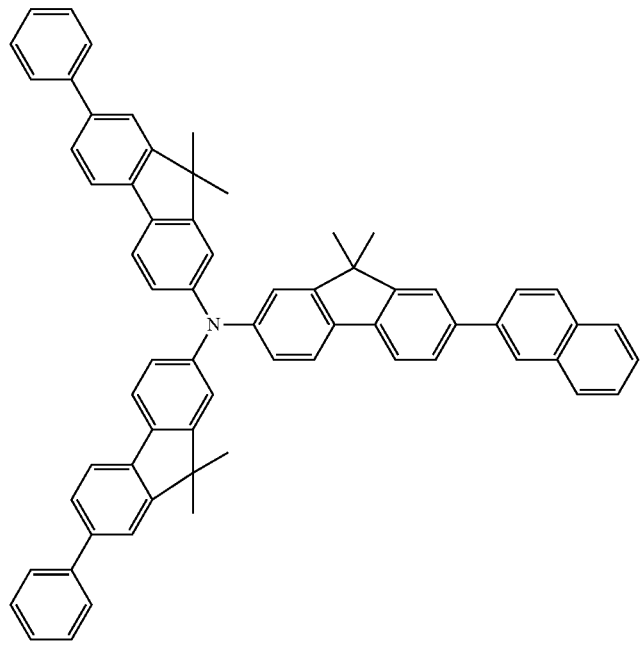
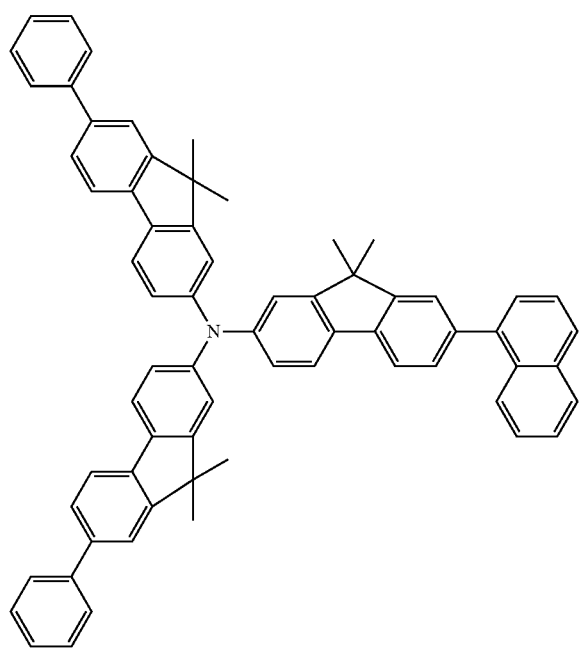

-continued
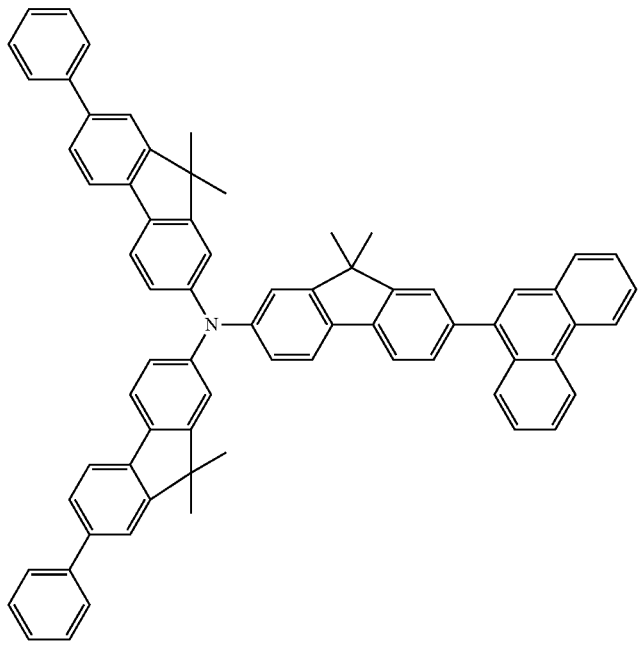
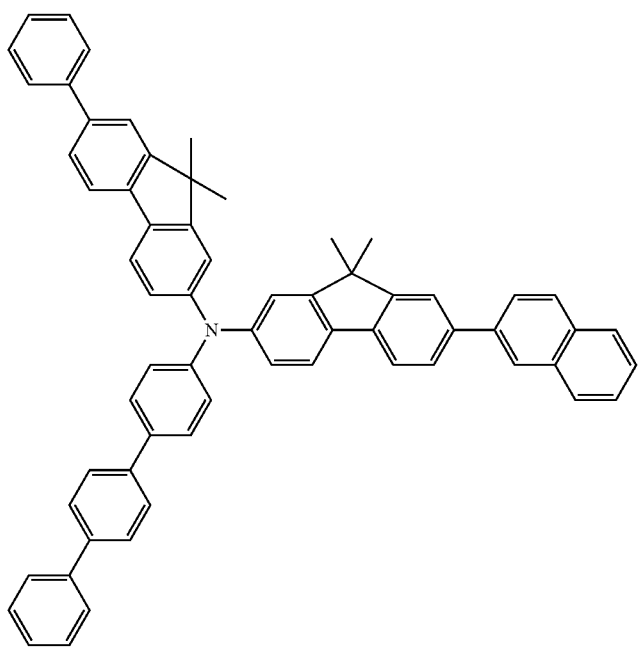

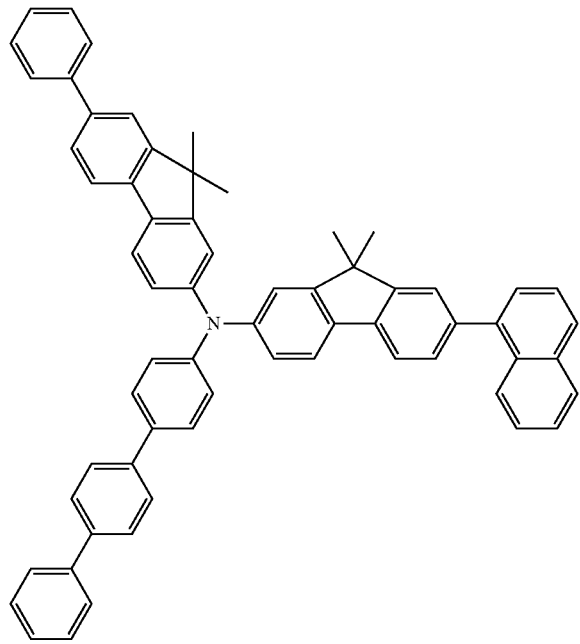
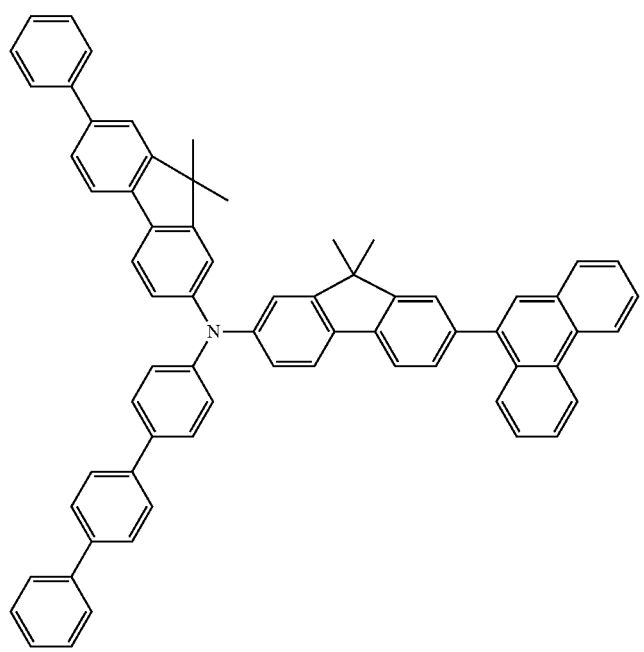

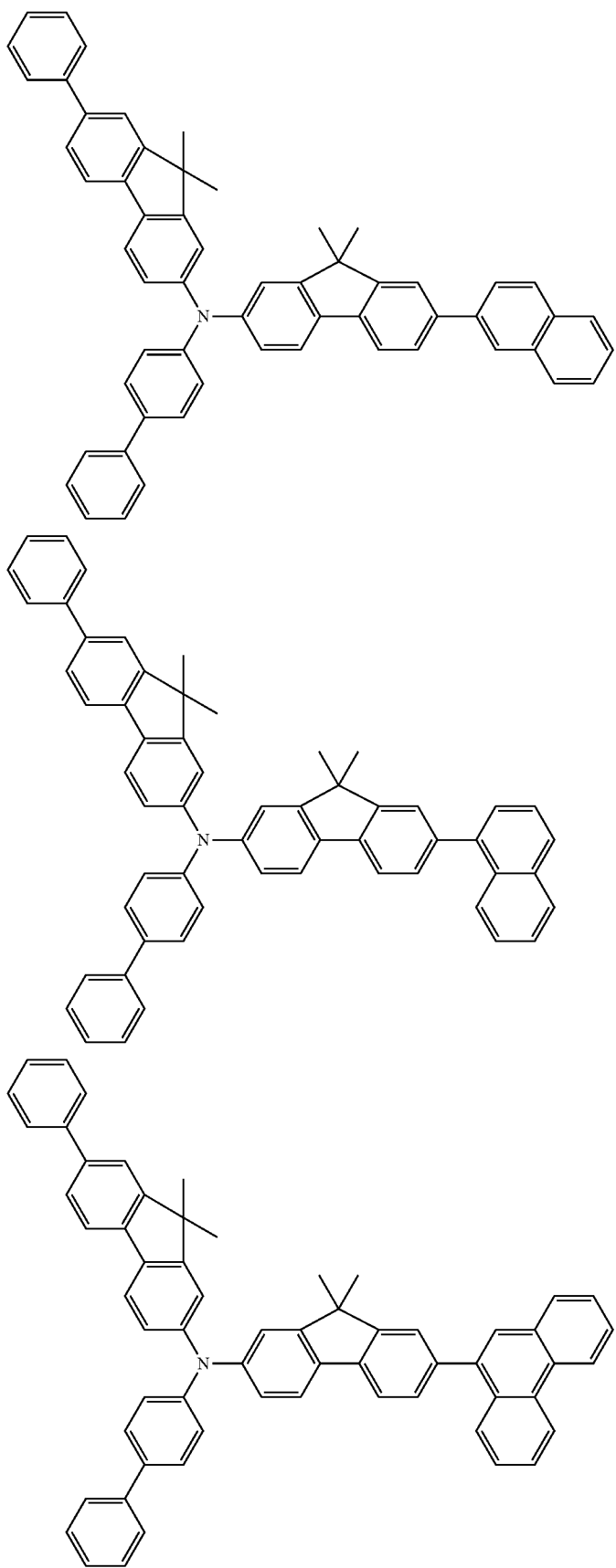

[Chemical formula 17]
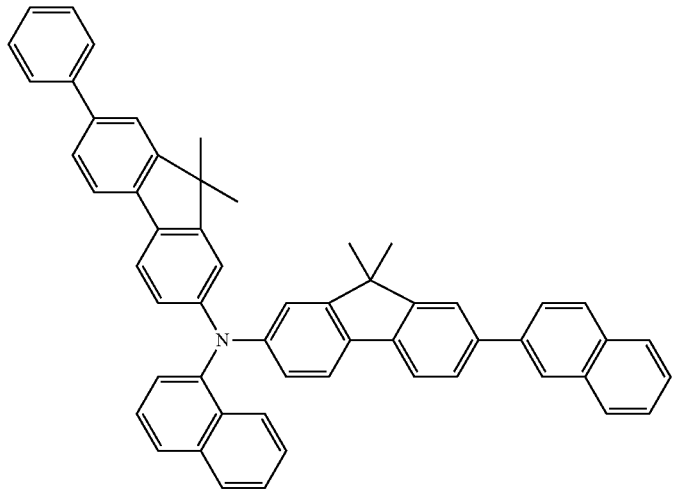
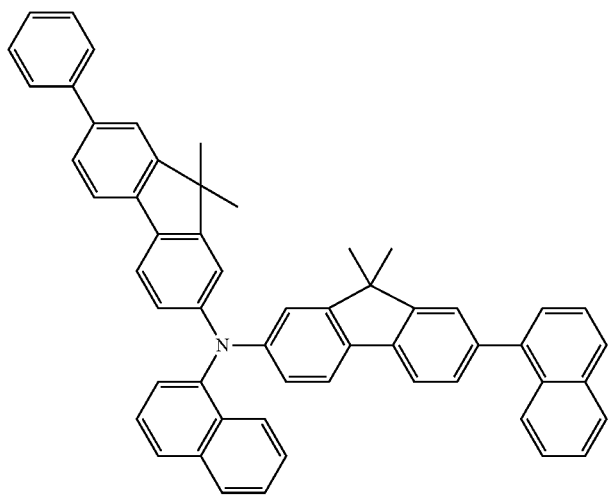
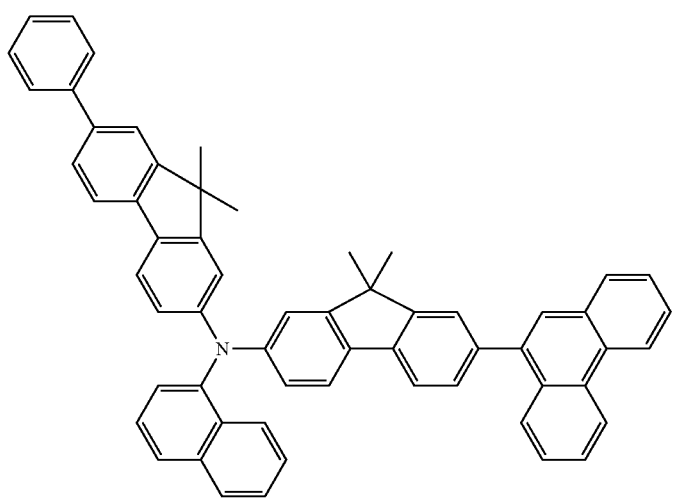

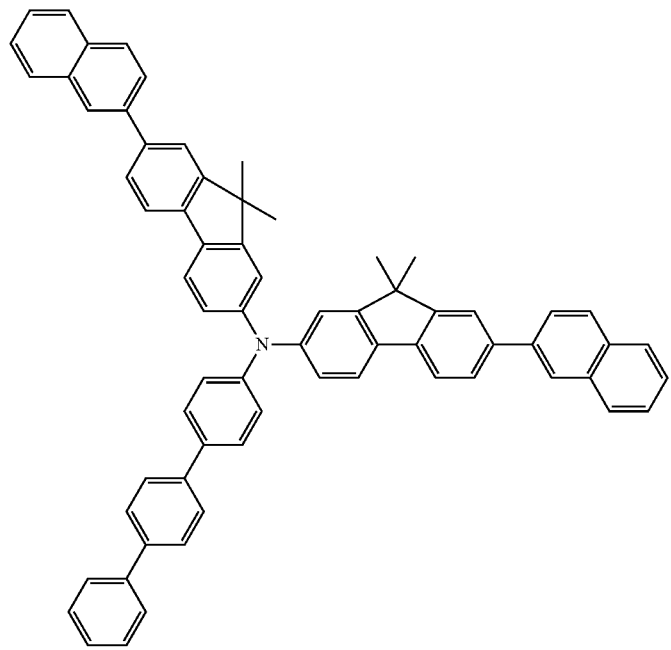
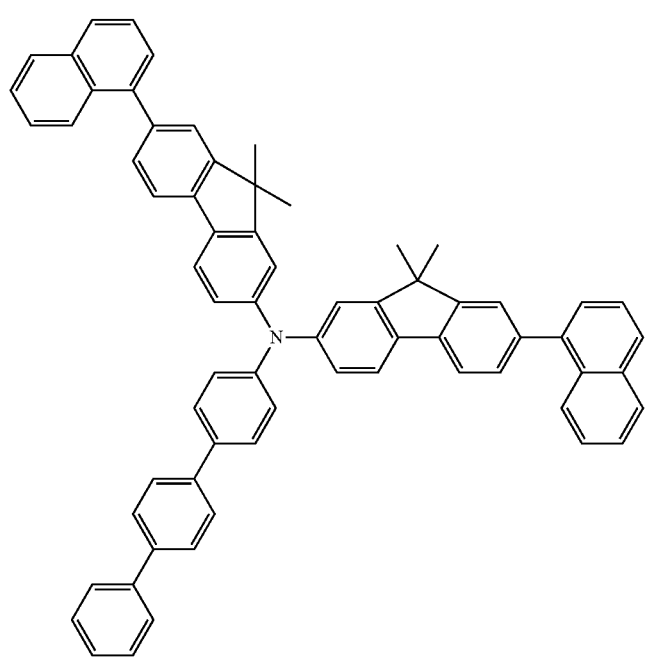

-continued
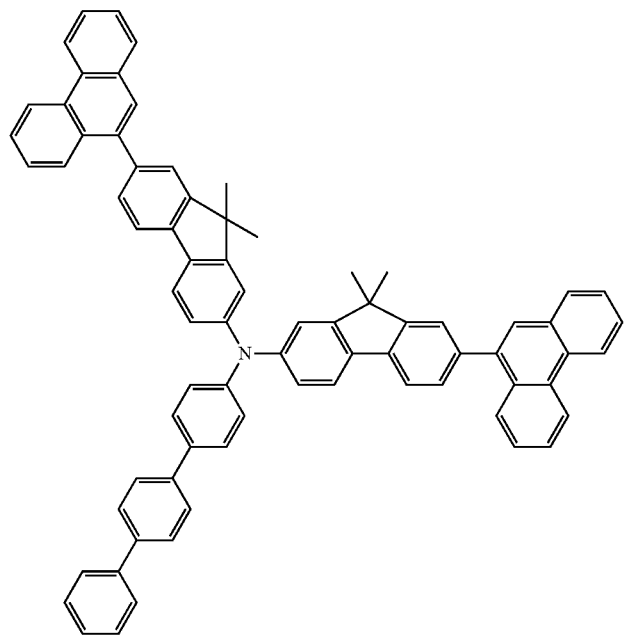
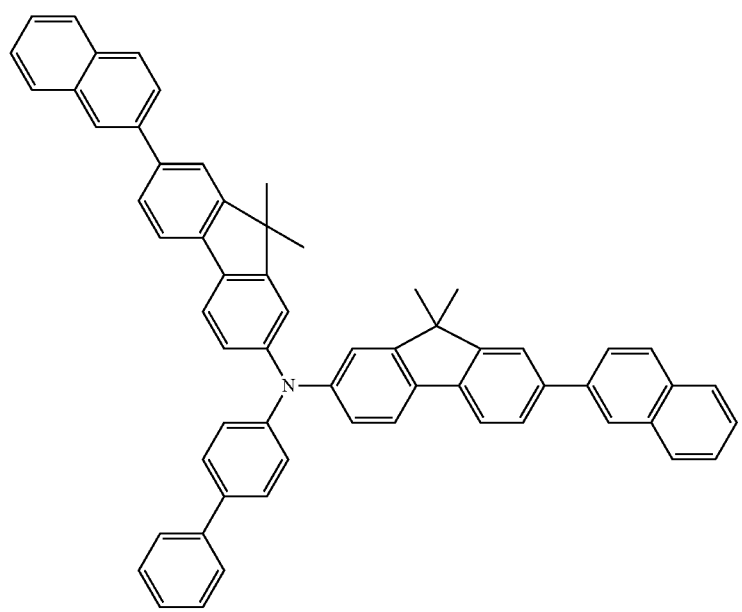

-continued
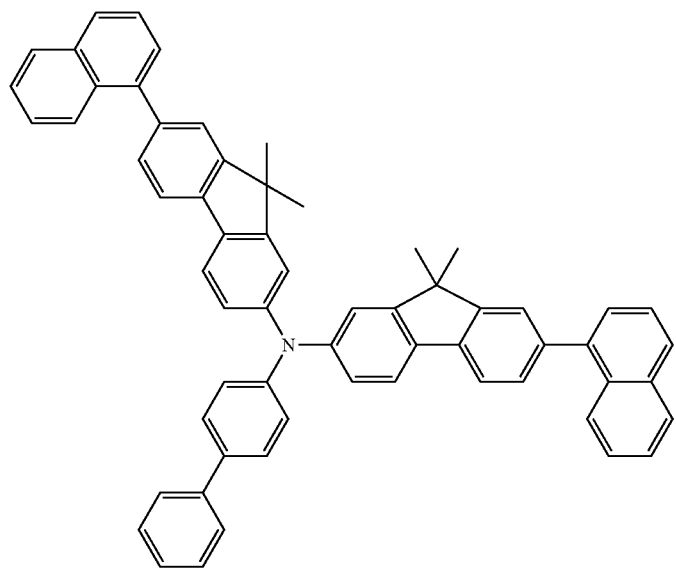
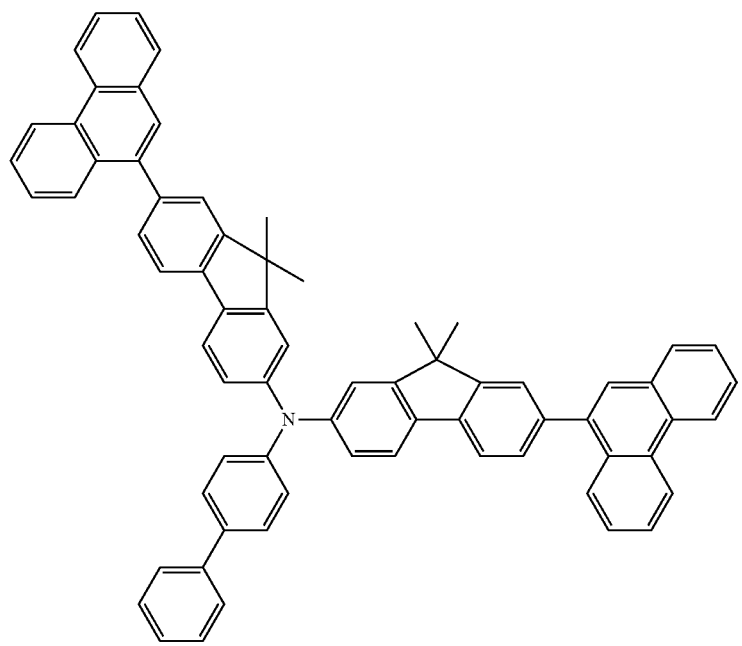

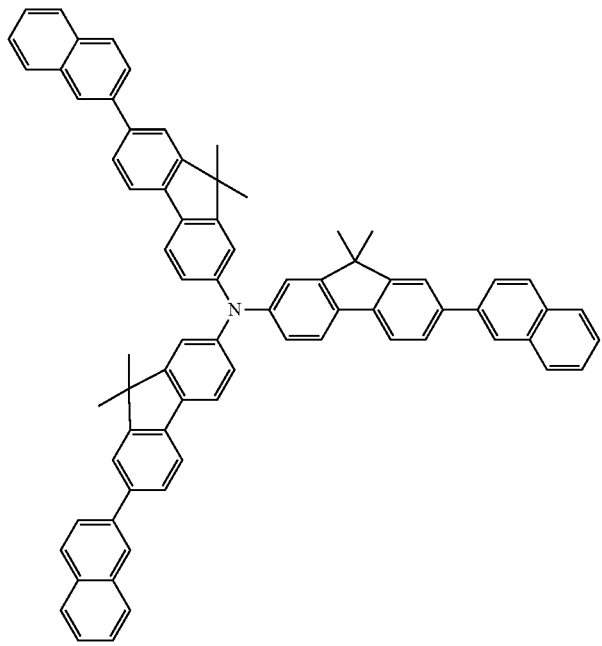
[Chemical formula 18]
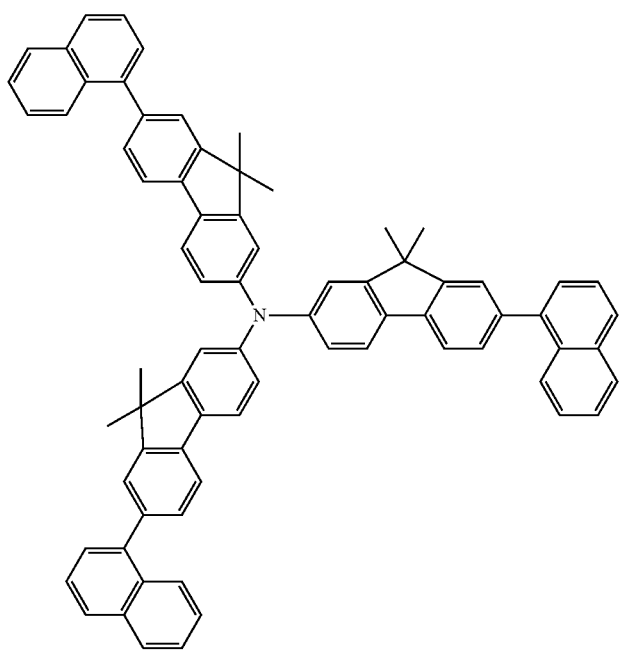 [SMILES: CC1(C)c2cc(-c3cccc4ccccc34)ccc2-c2ccc(N(c3ccc4c(c3)C(C)(C)c3cc(-c5cccc6ccccc56)ccc3-4)c3ccc4c(c3)C(C)(C)c3cc(-c5cccc6ccccc56)ccc3-4)cc21]

-continued
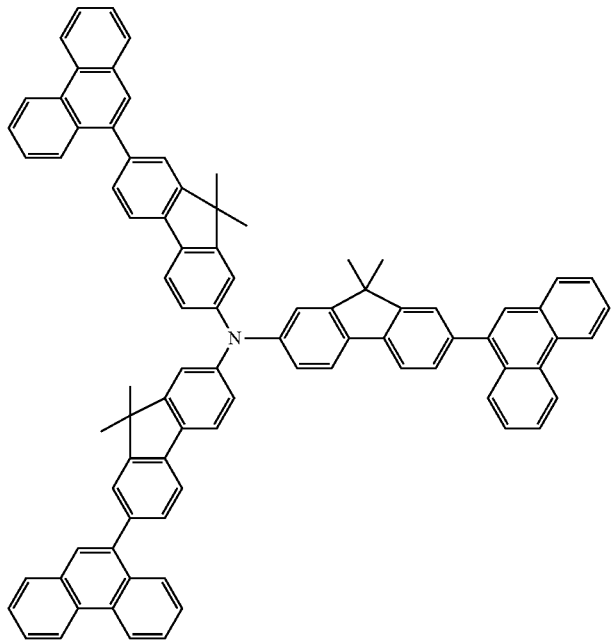
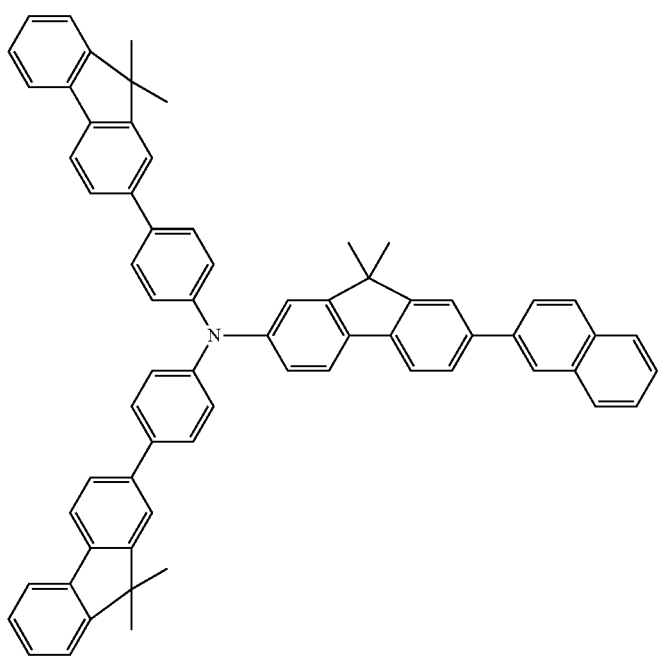

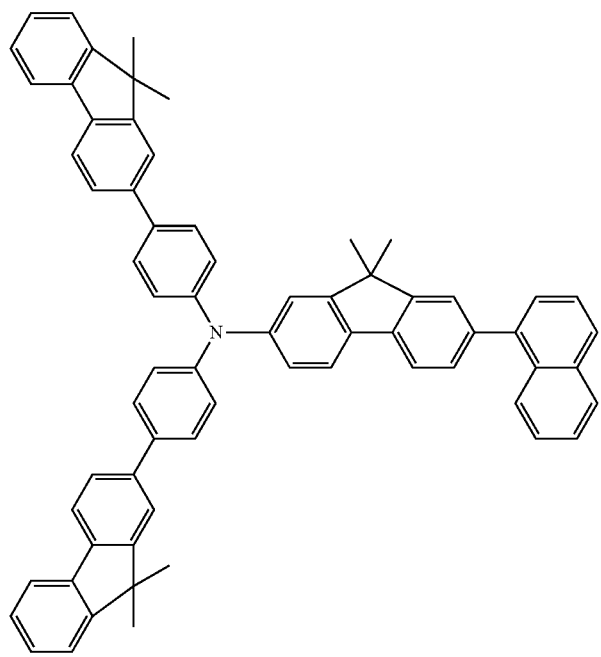
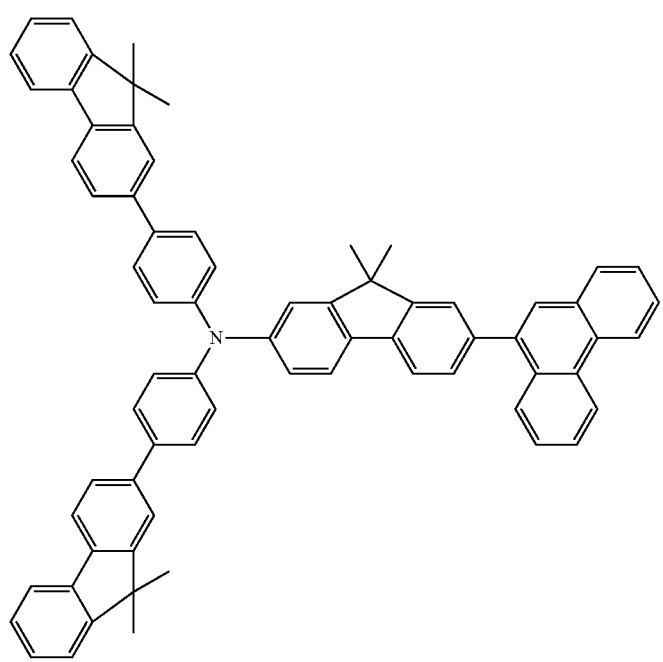

-continued
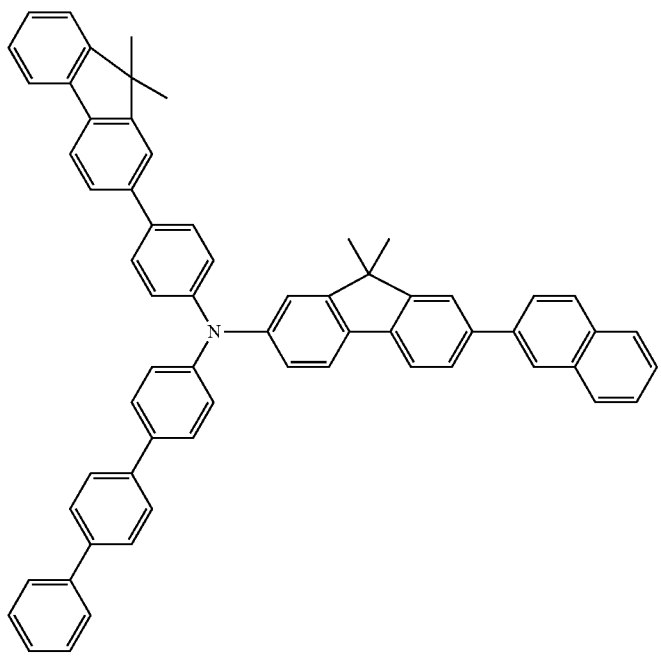
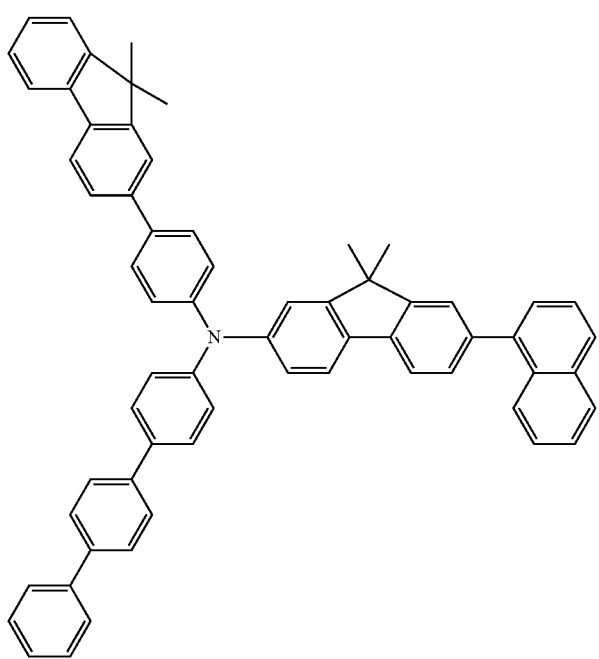

-continued
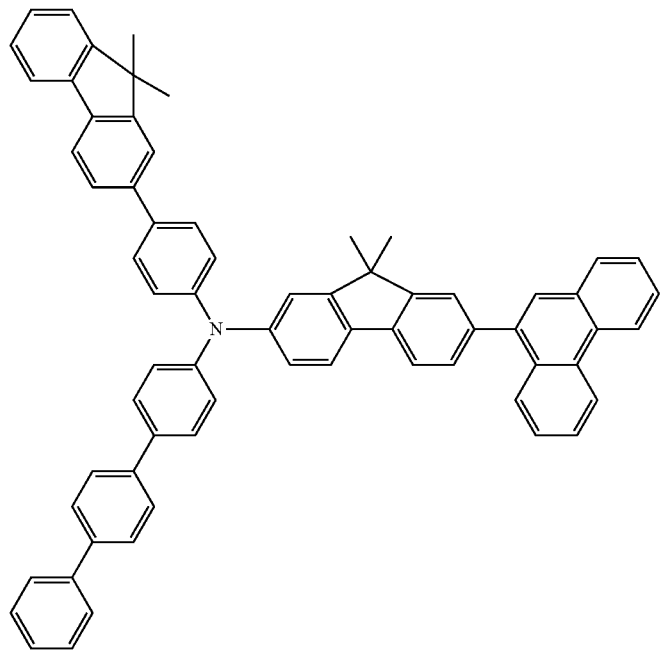
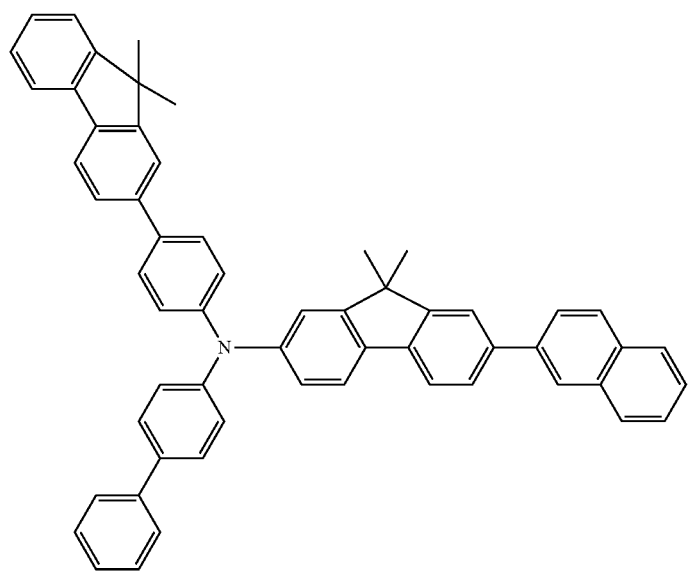

-continued
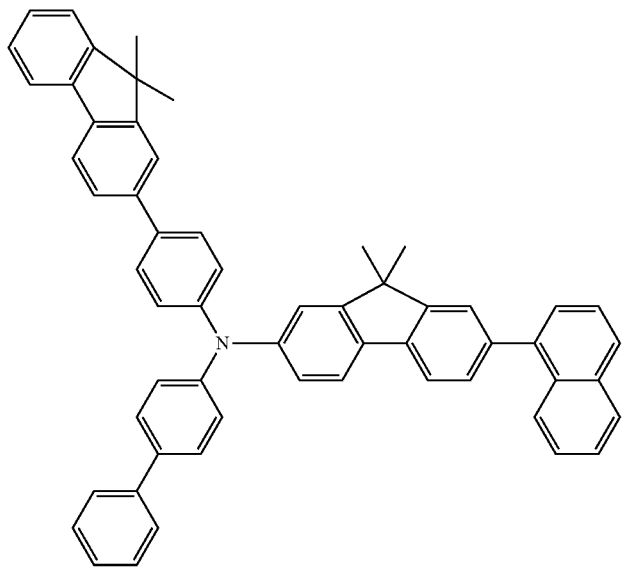
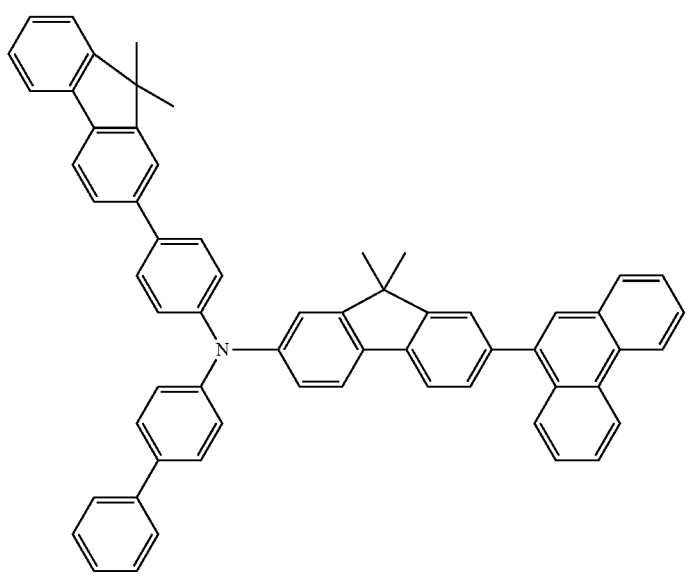

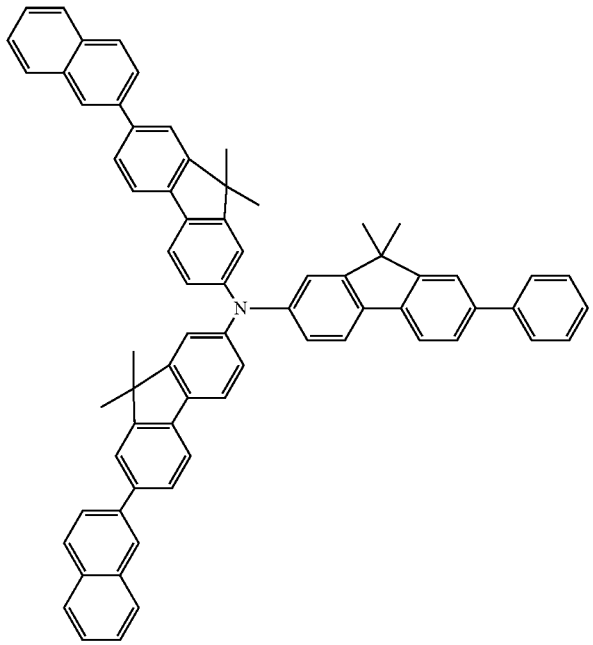
[Chemical formula 19]
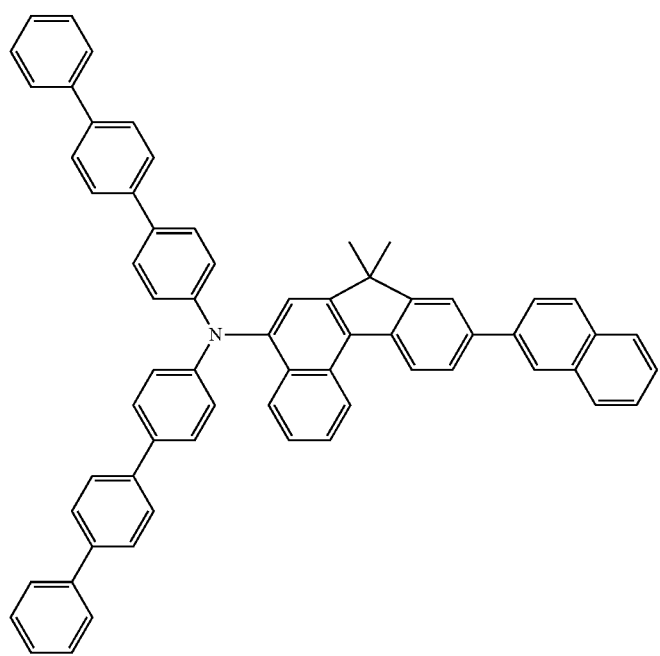

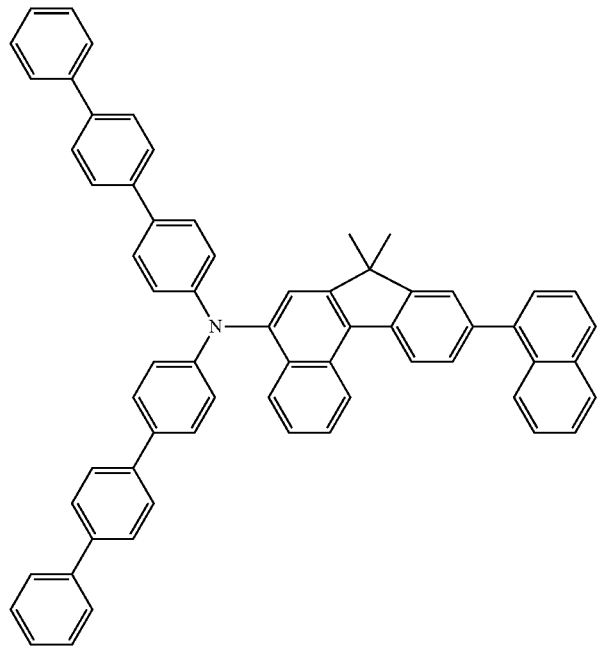
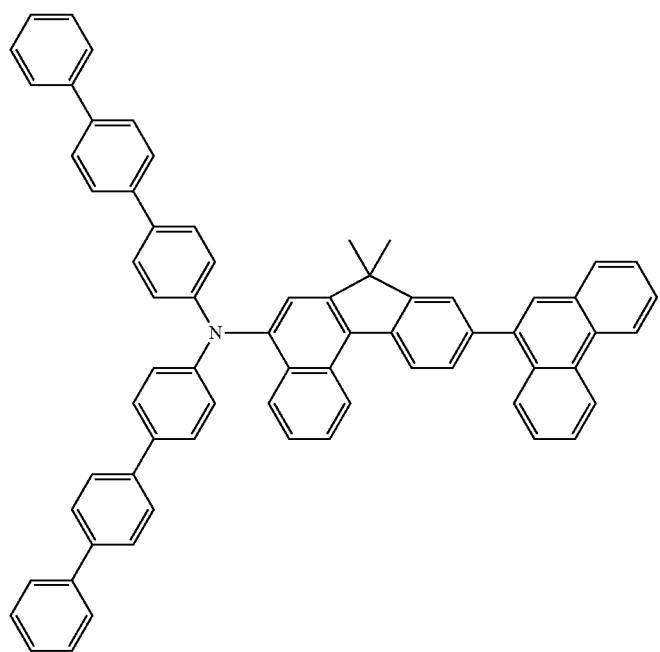

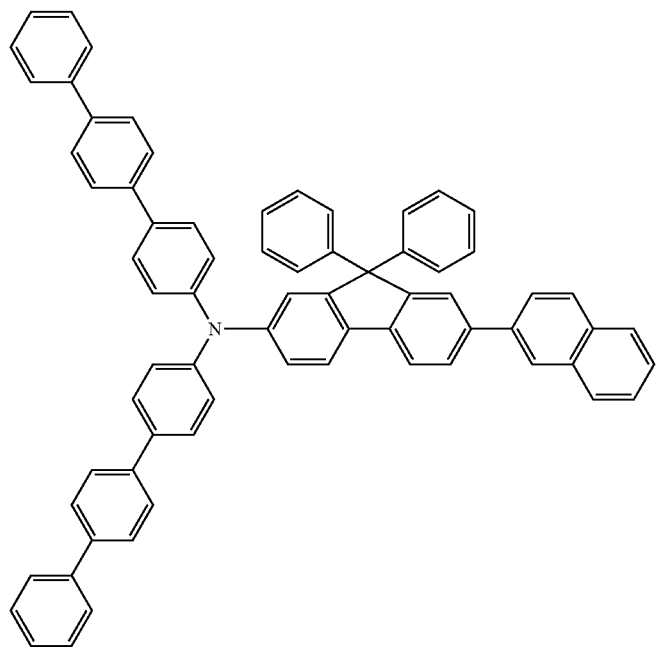
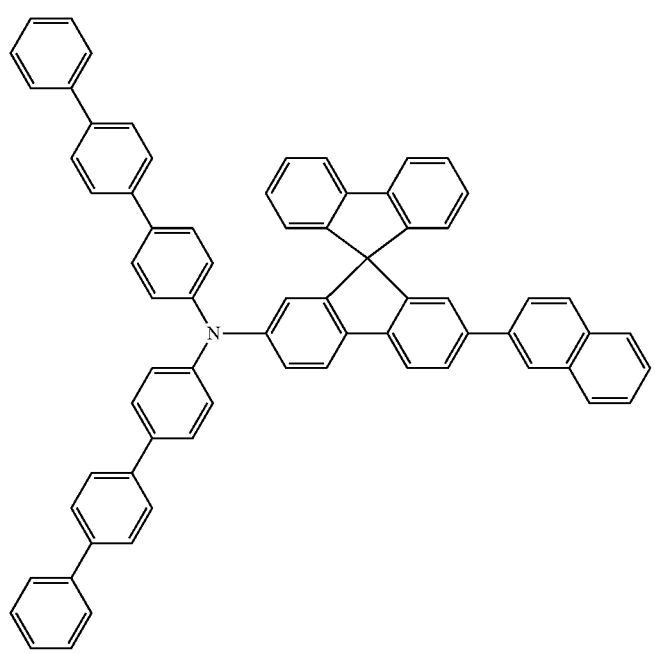

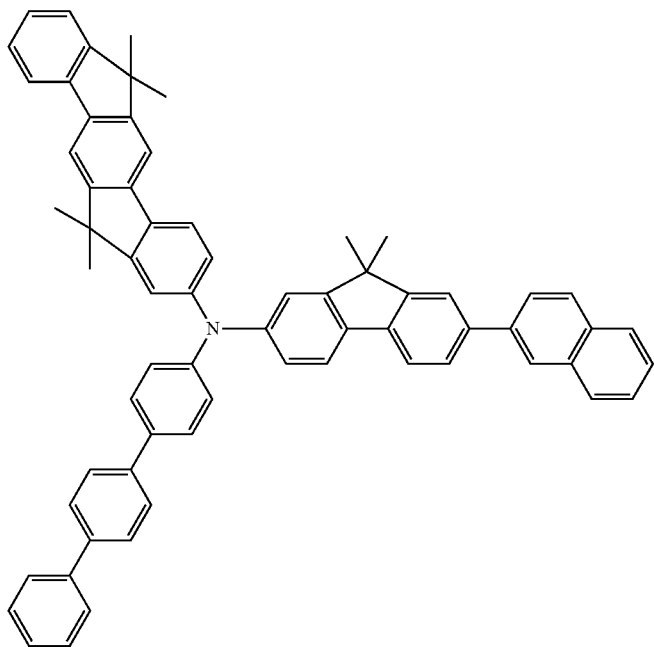
[Chemical formula 20]
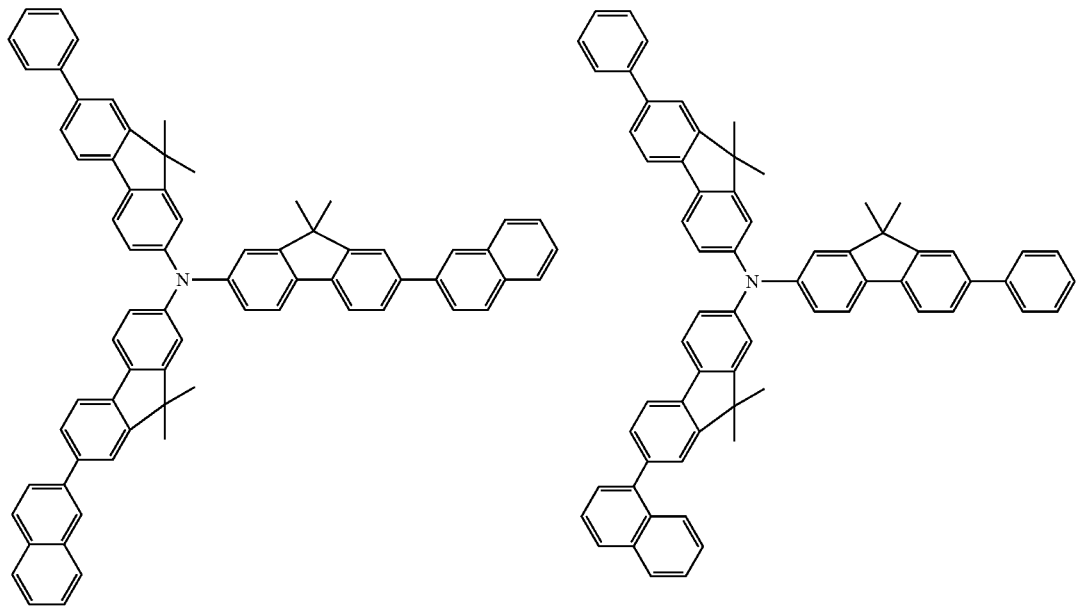

-continued
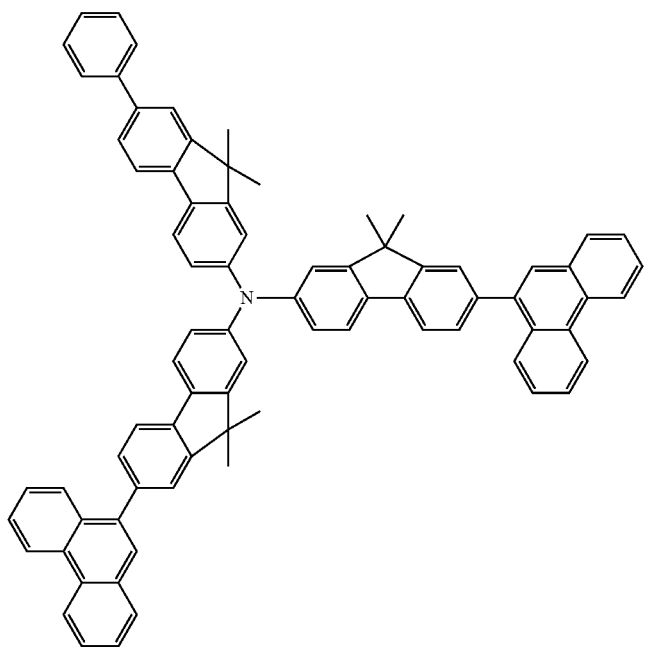
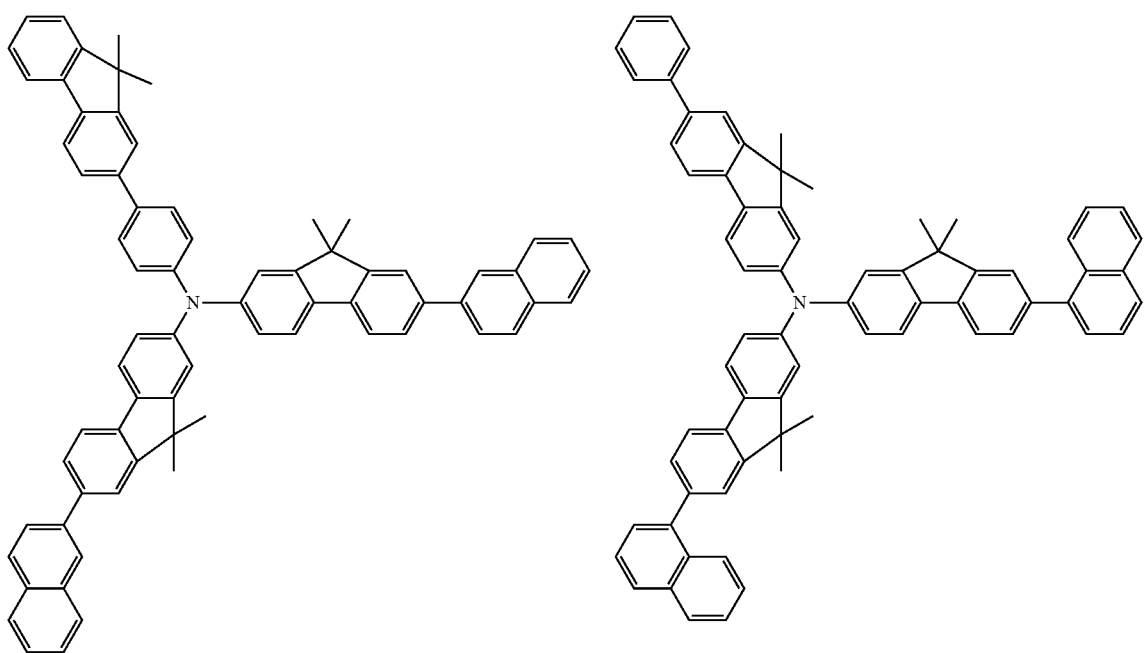

-continued
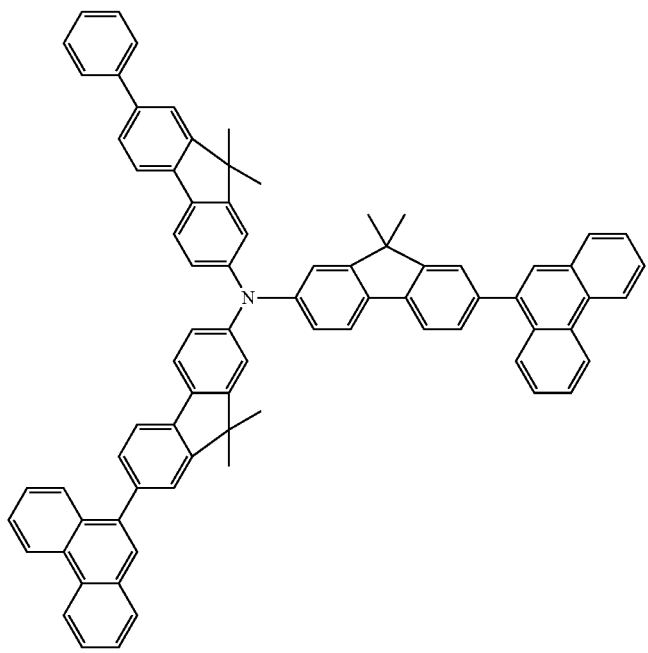
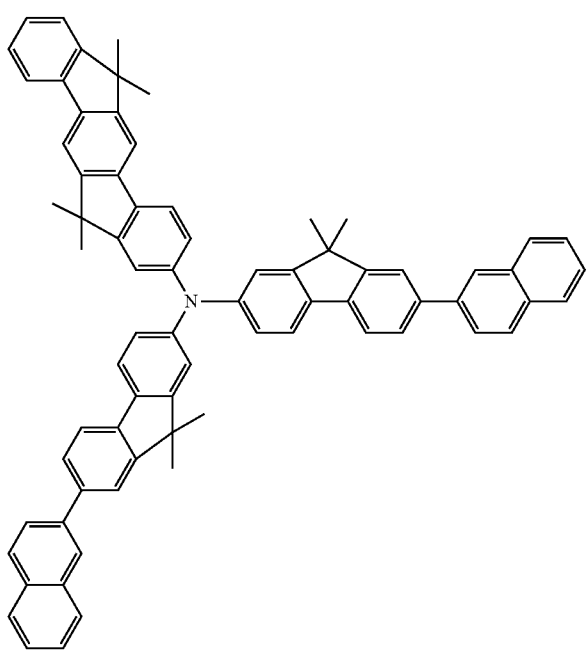

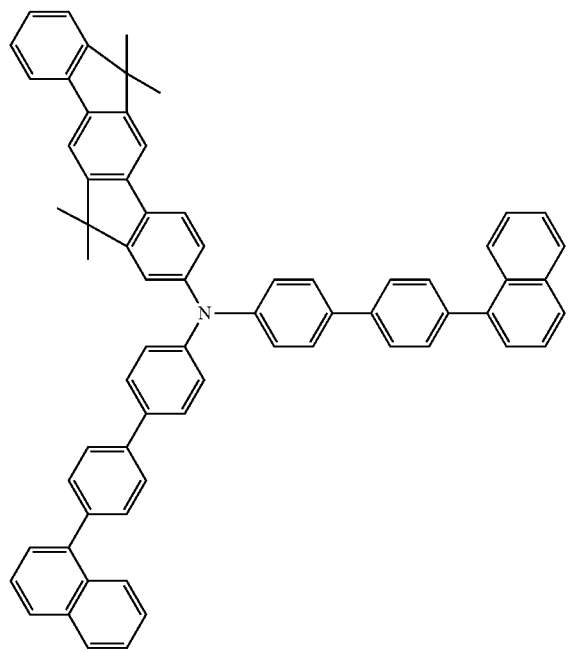
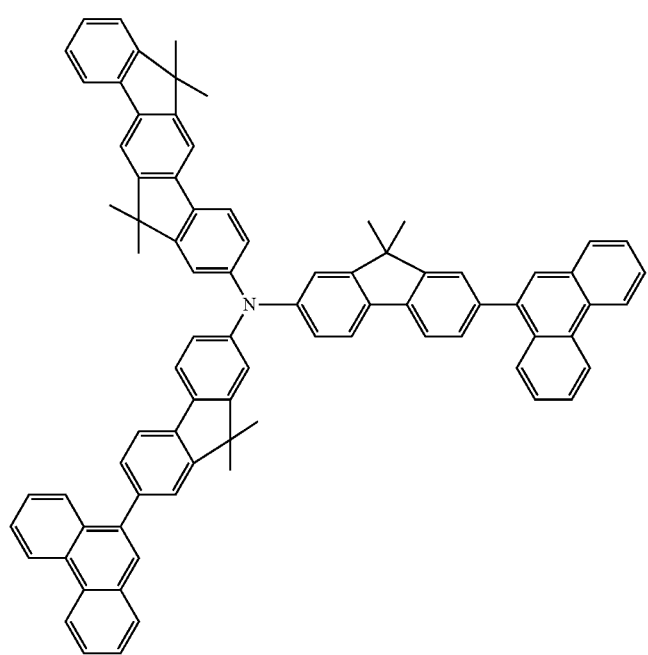

-continued
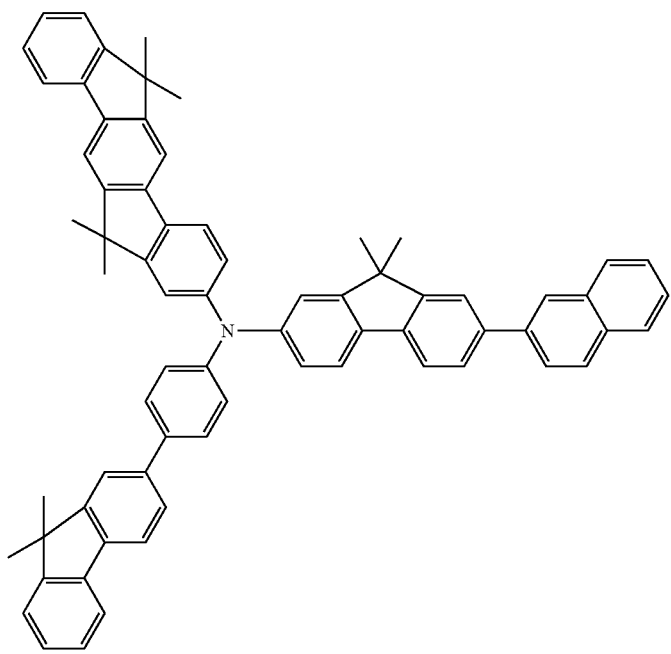
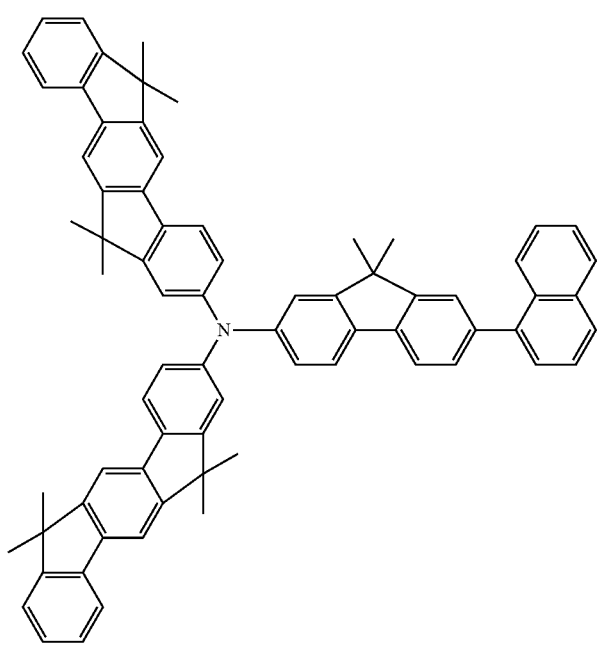

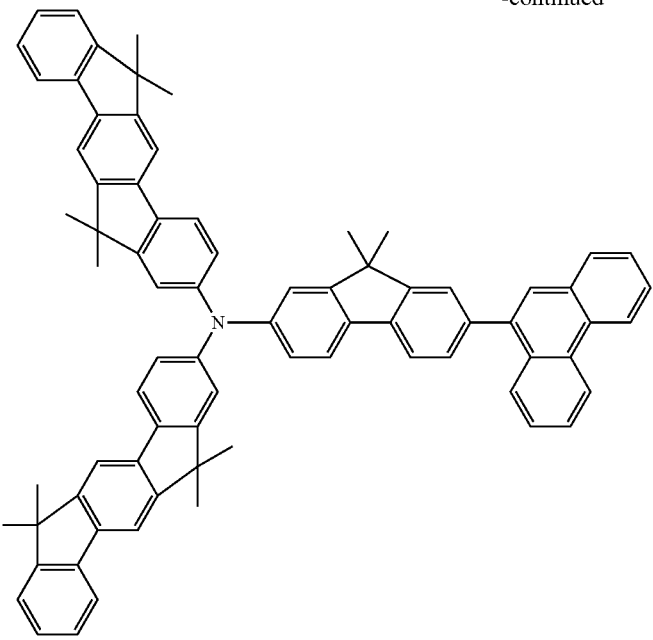
[Chemical formula 21]
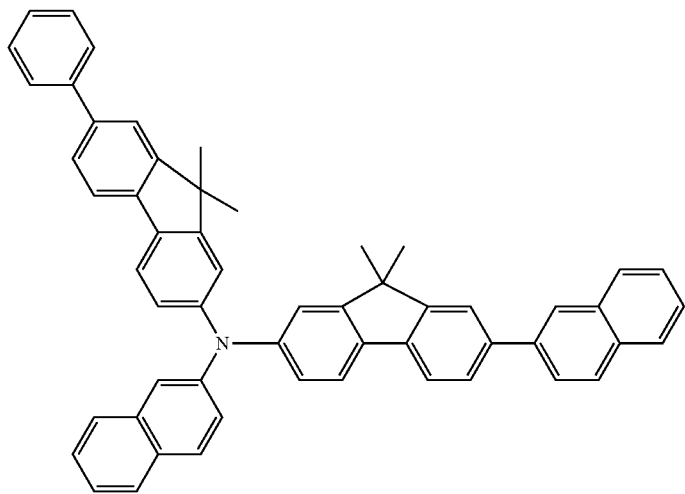
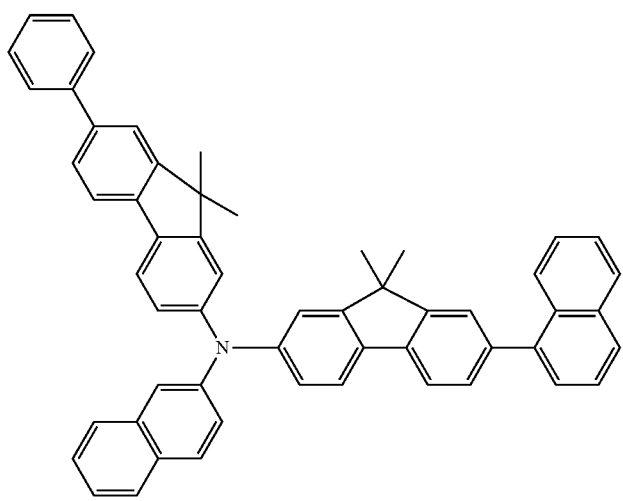

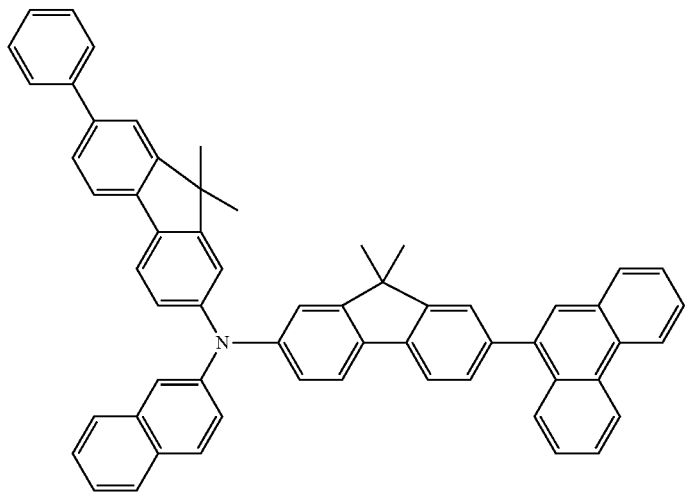
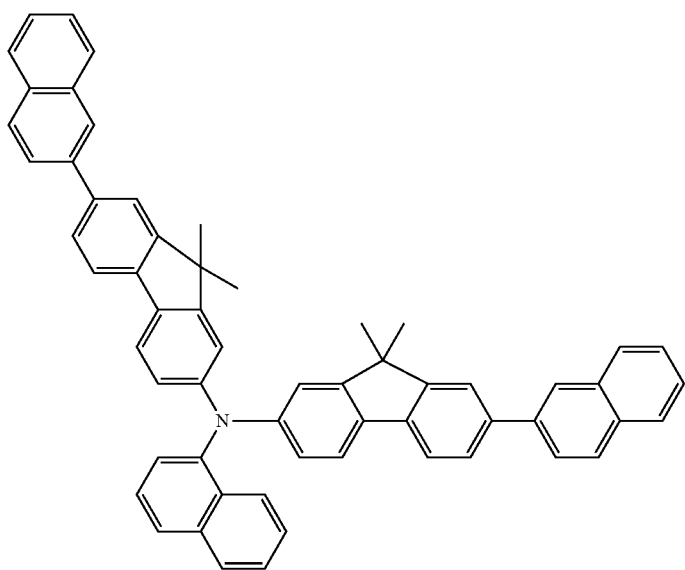
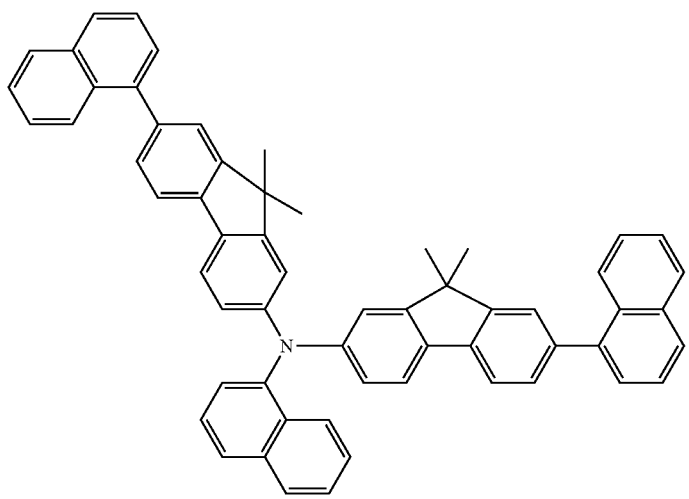

-continued
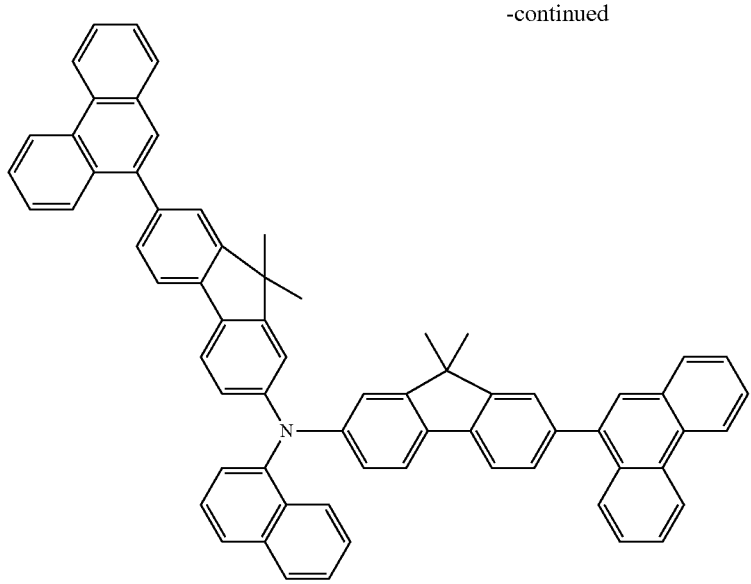
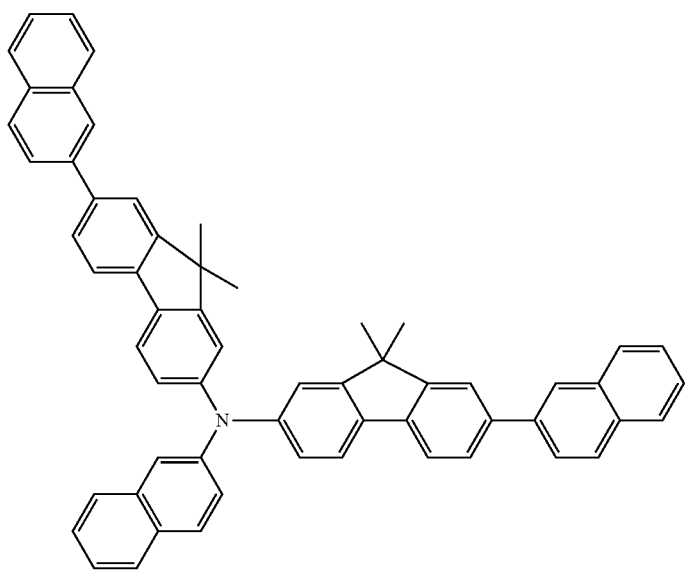
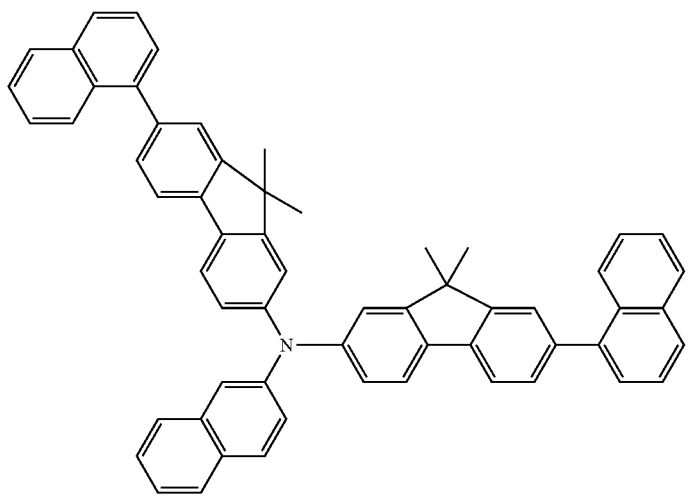

-continued
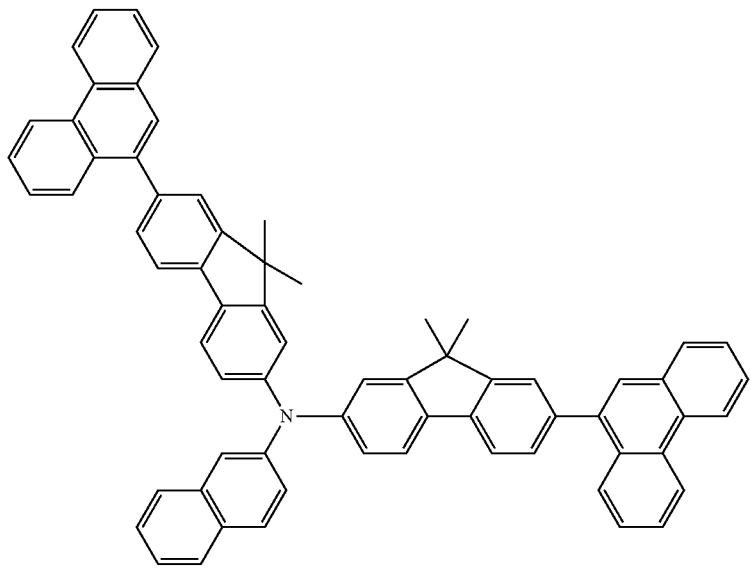
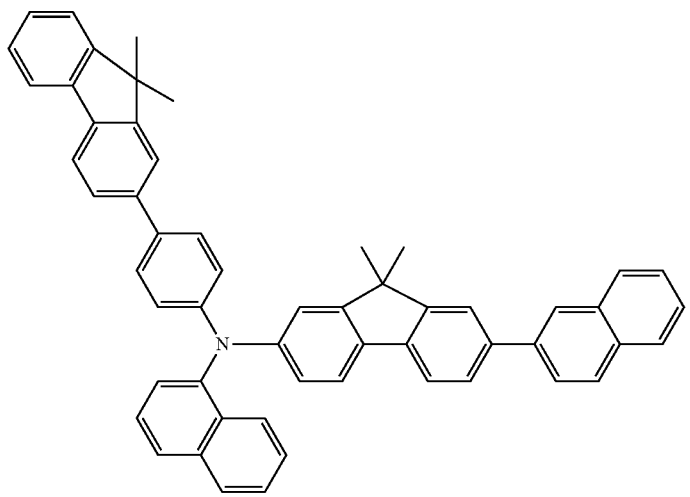
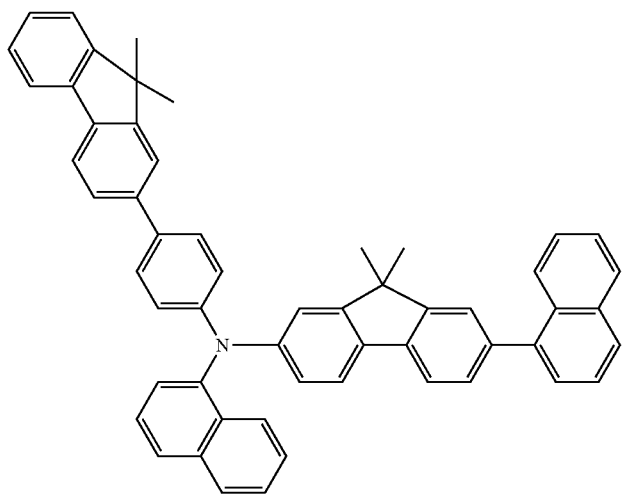

-continued
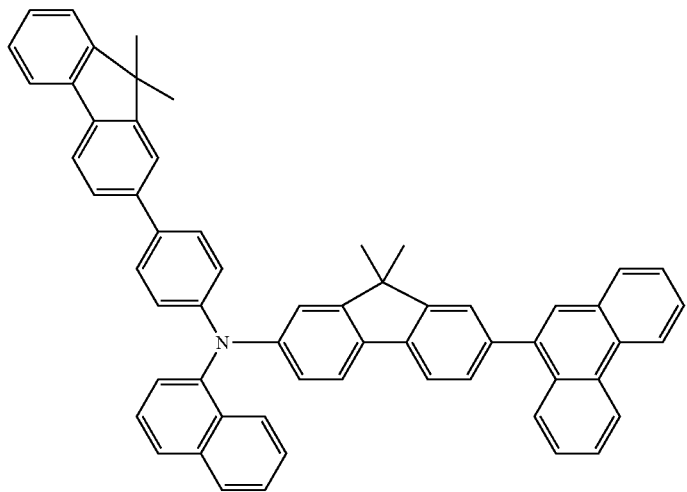
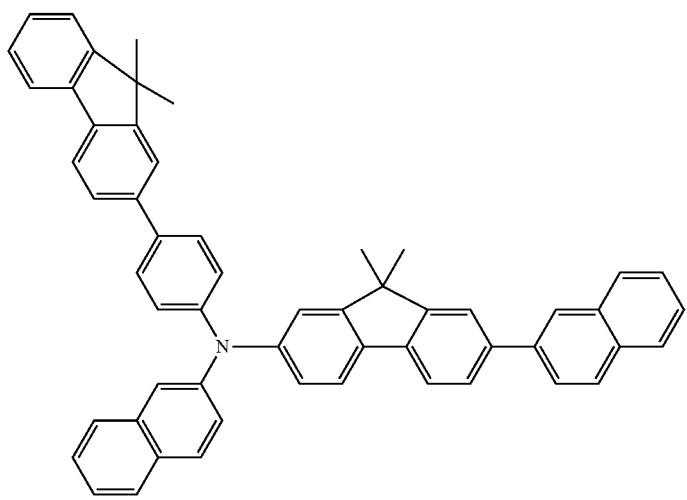
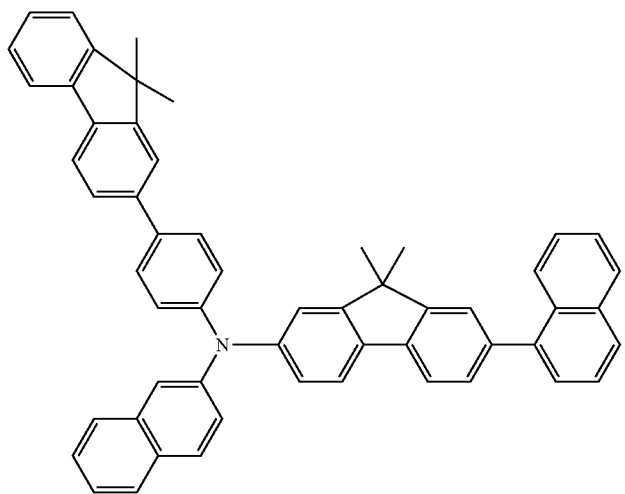

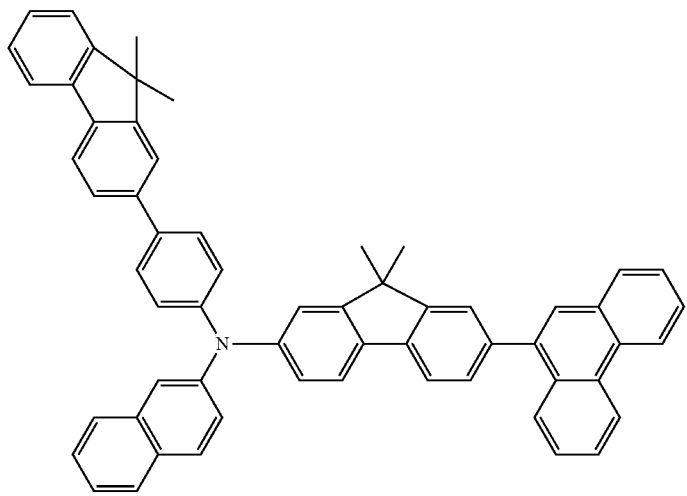
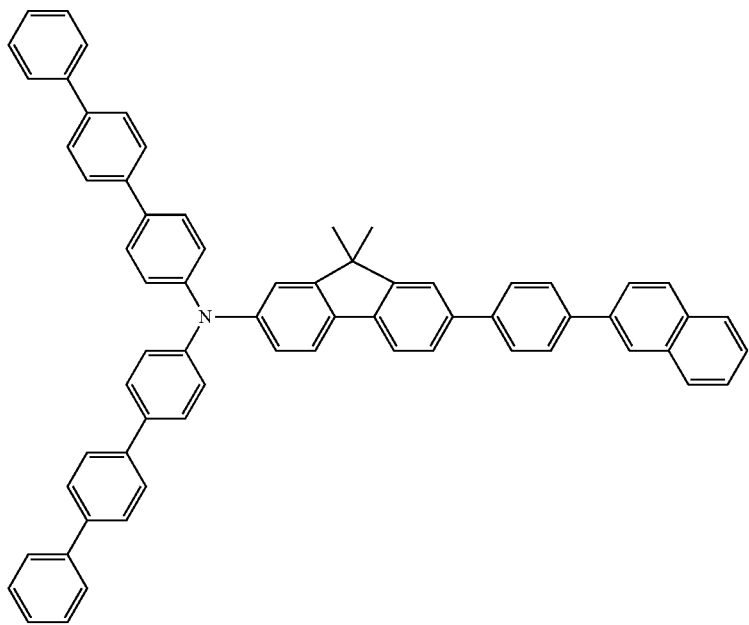
[Chemical formula 22]

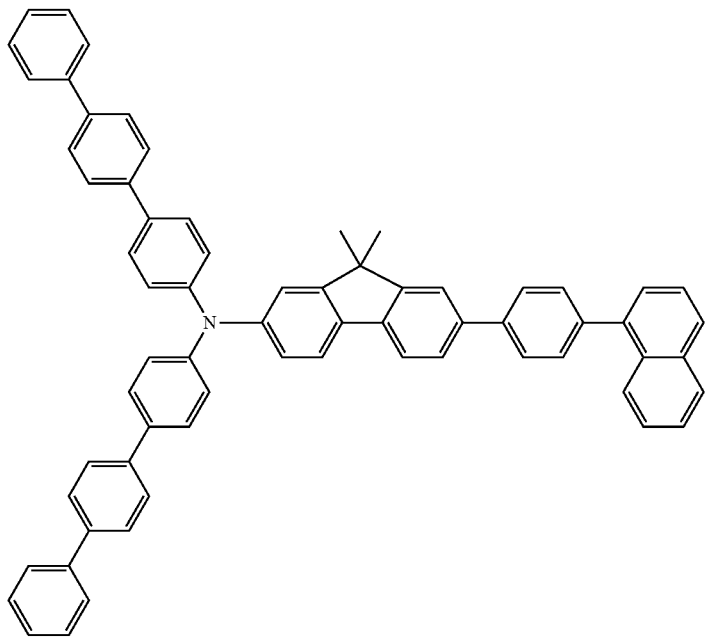
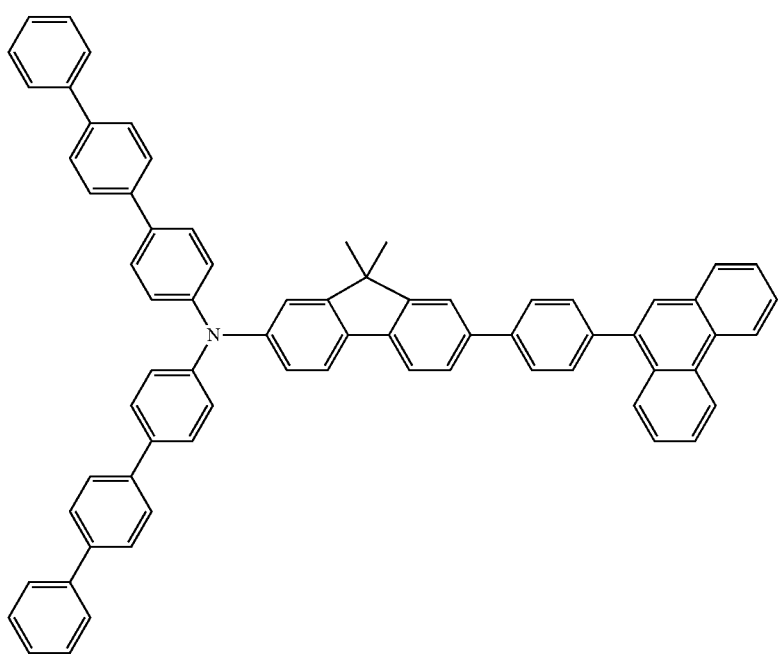

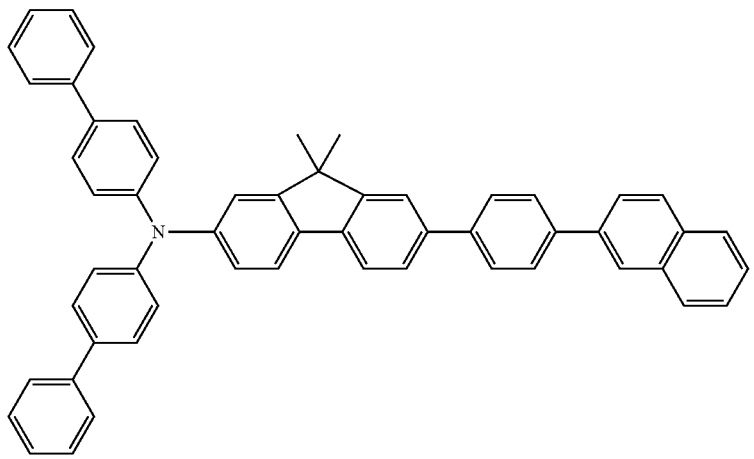
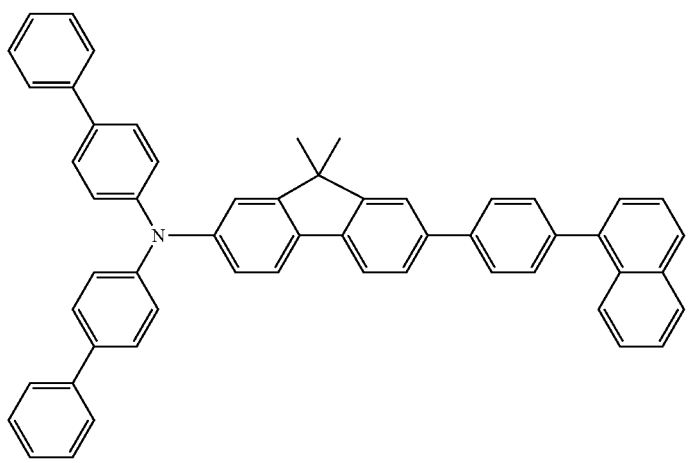
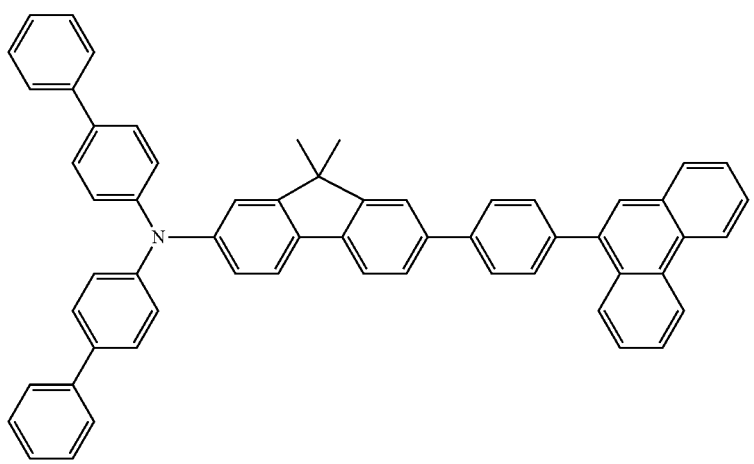

-continued
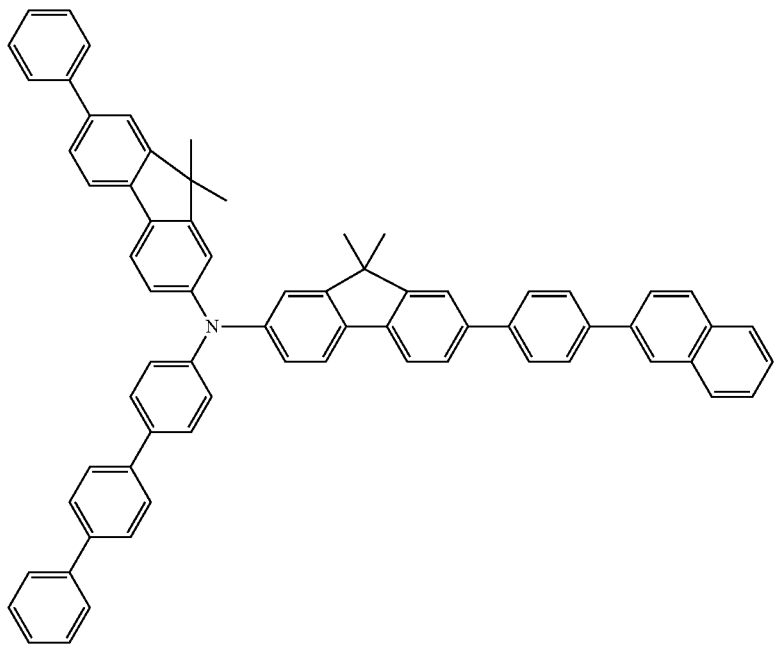
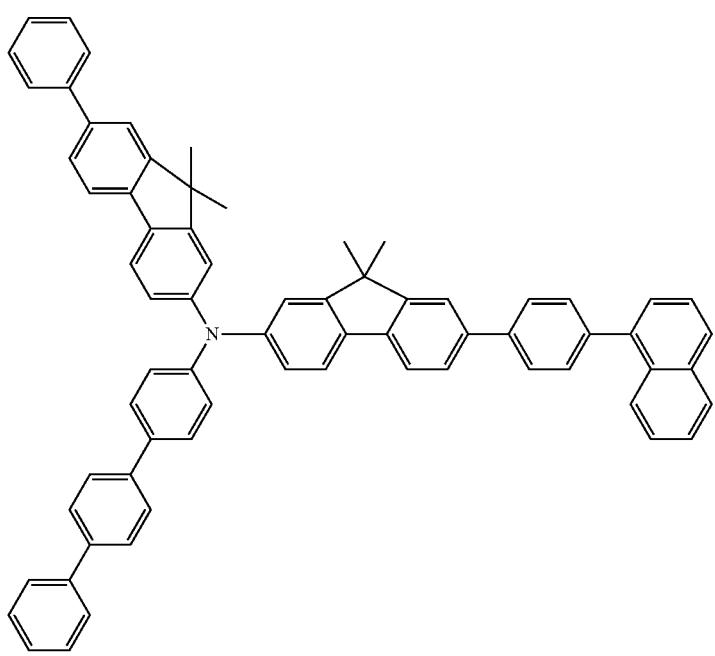

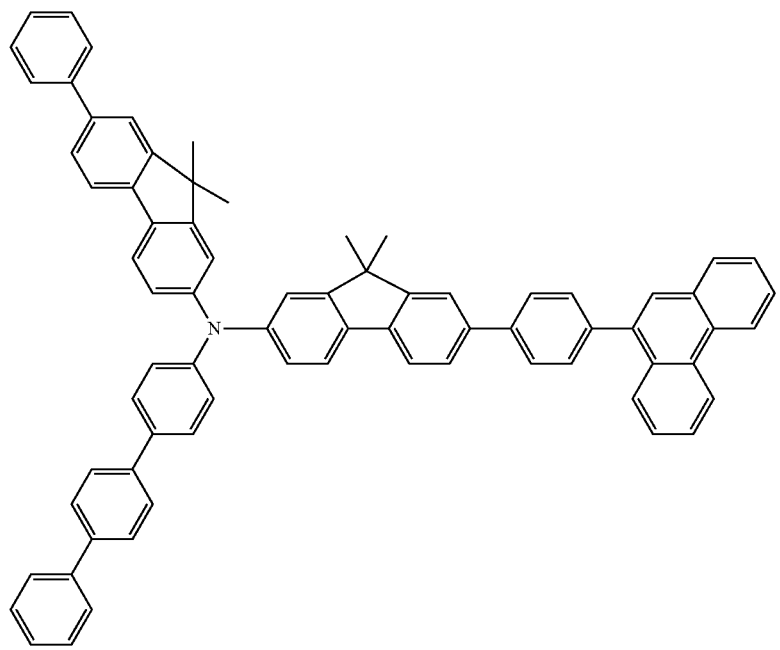
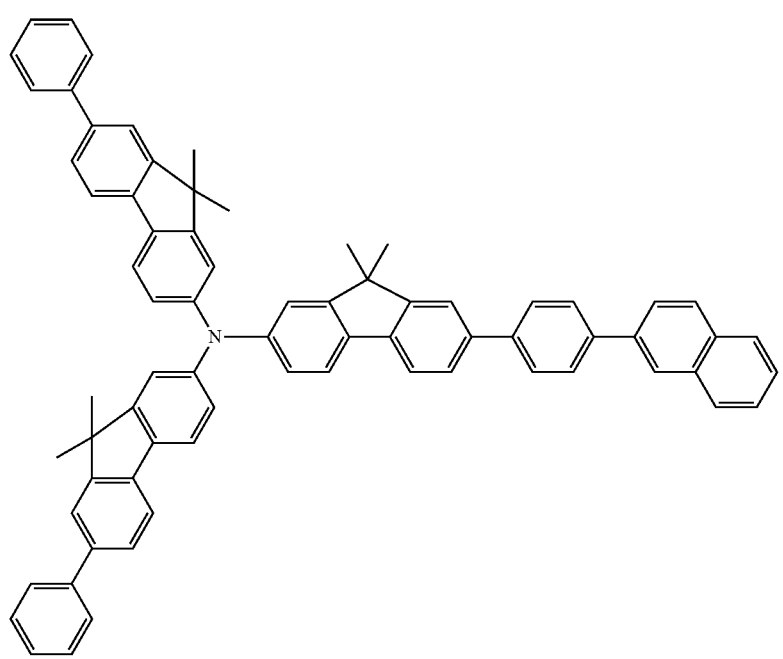

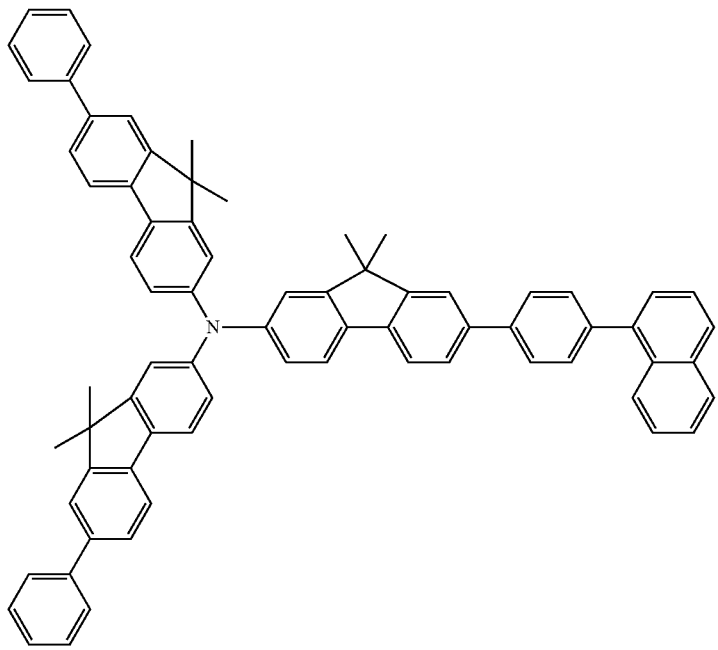
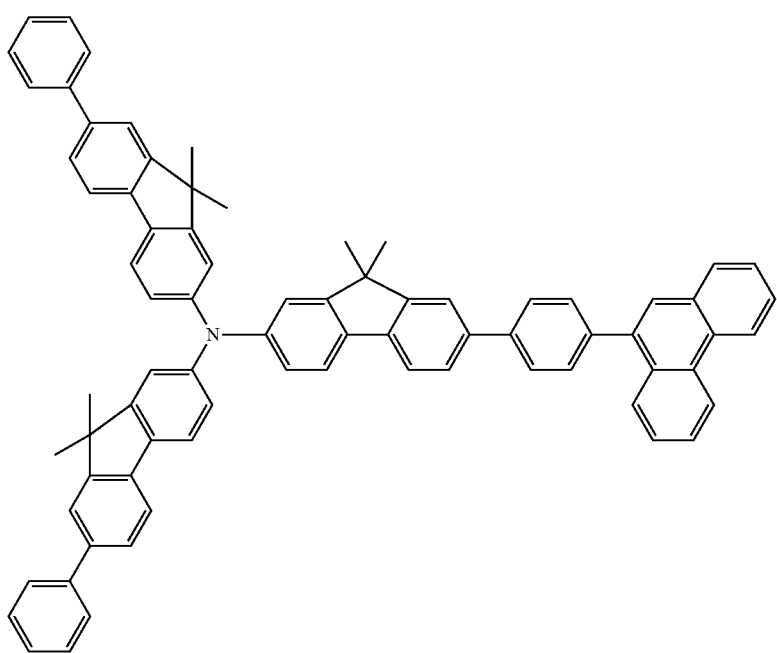

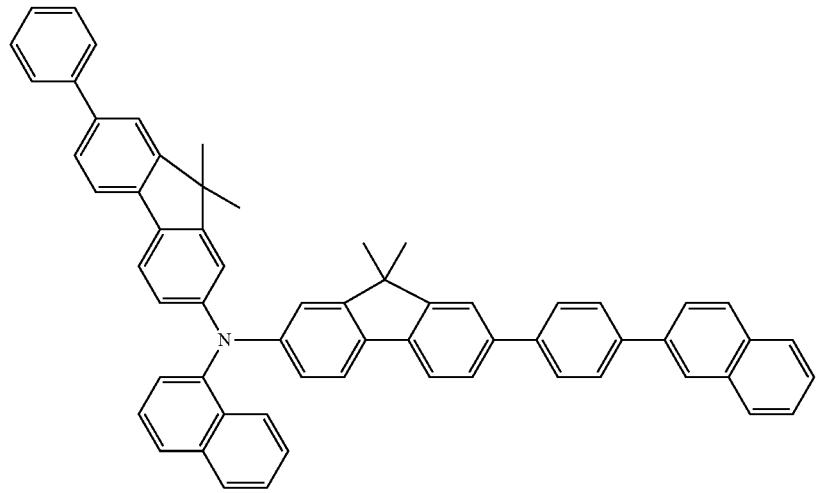
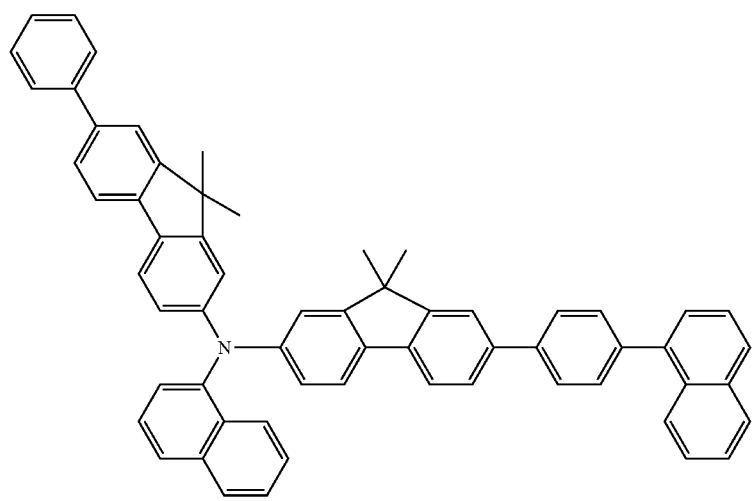
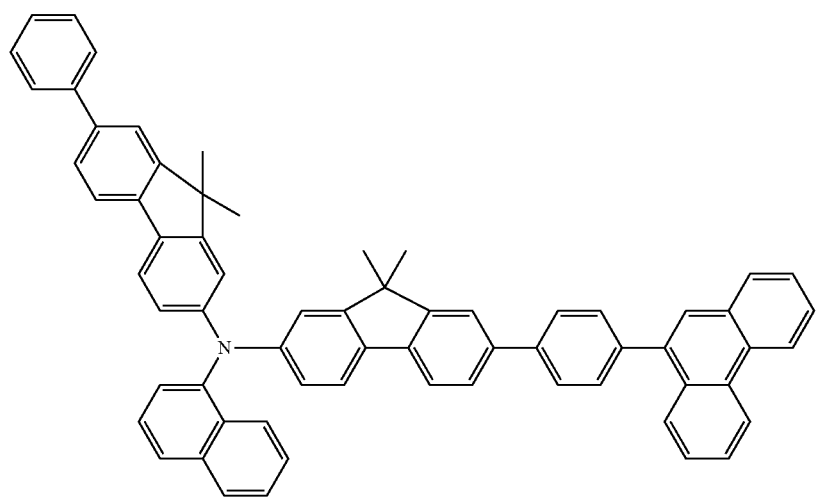

-continued
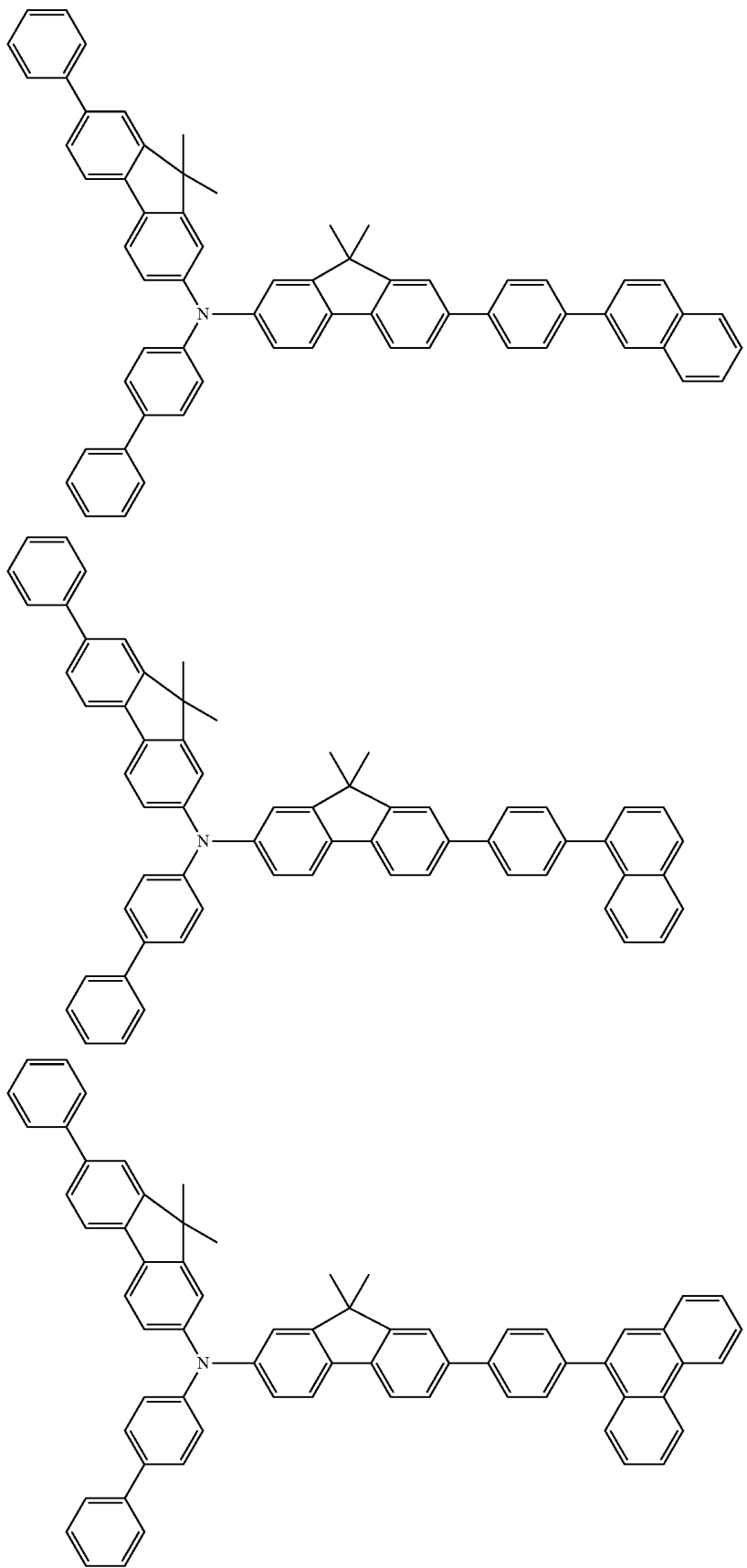

-continued
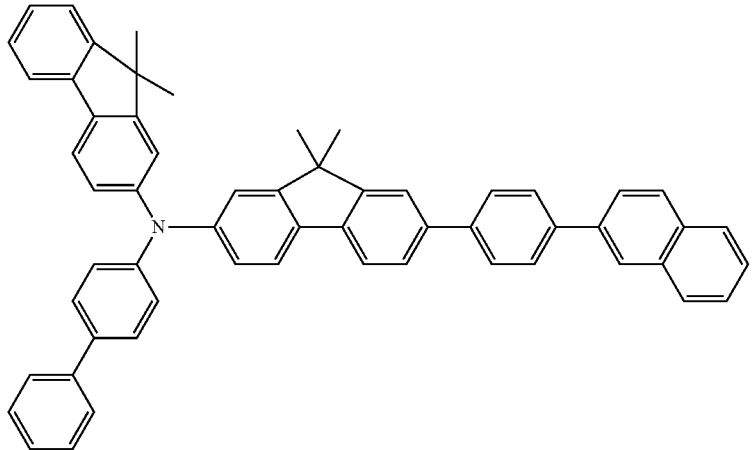
[Chemical formula 23]
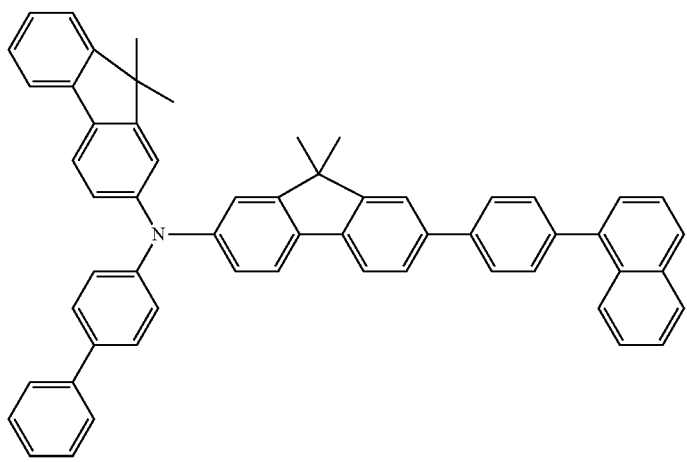
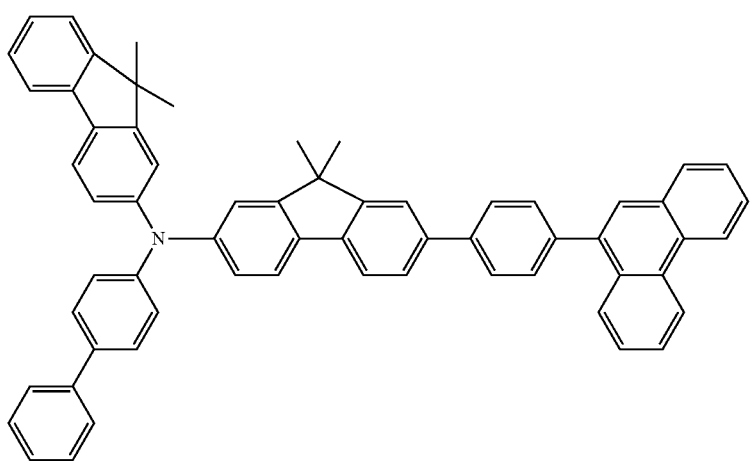

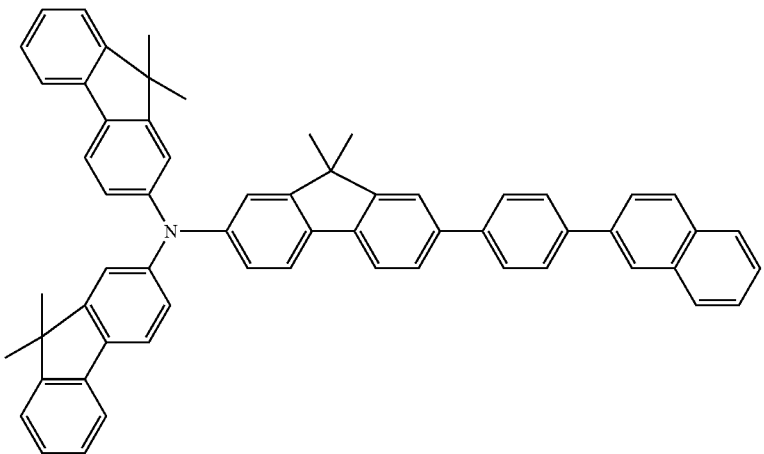
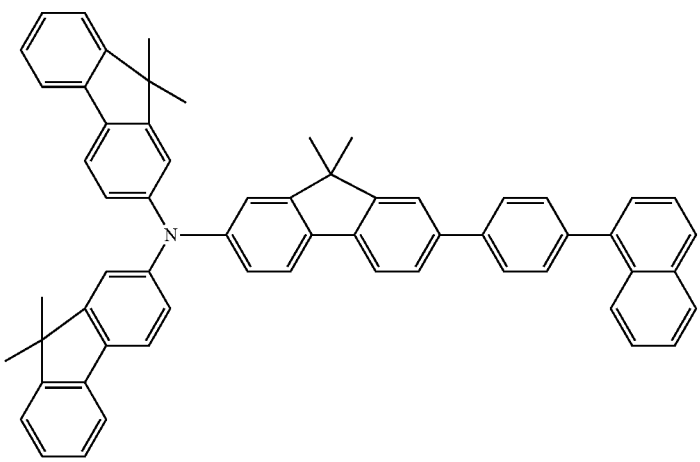
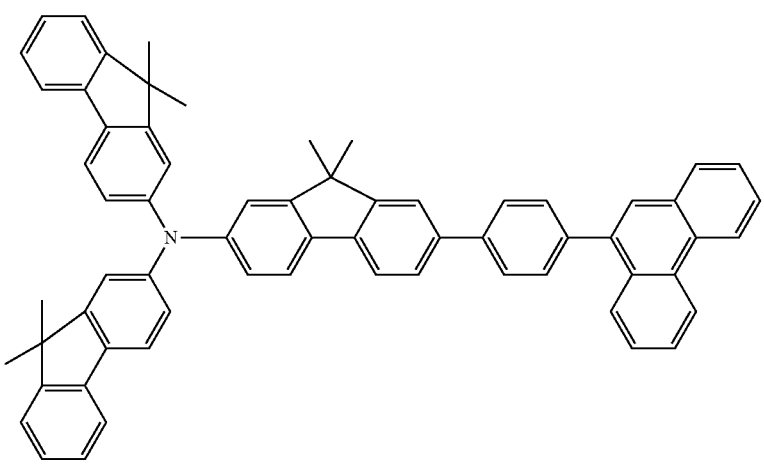

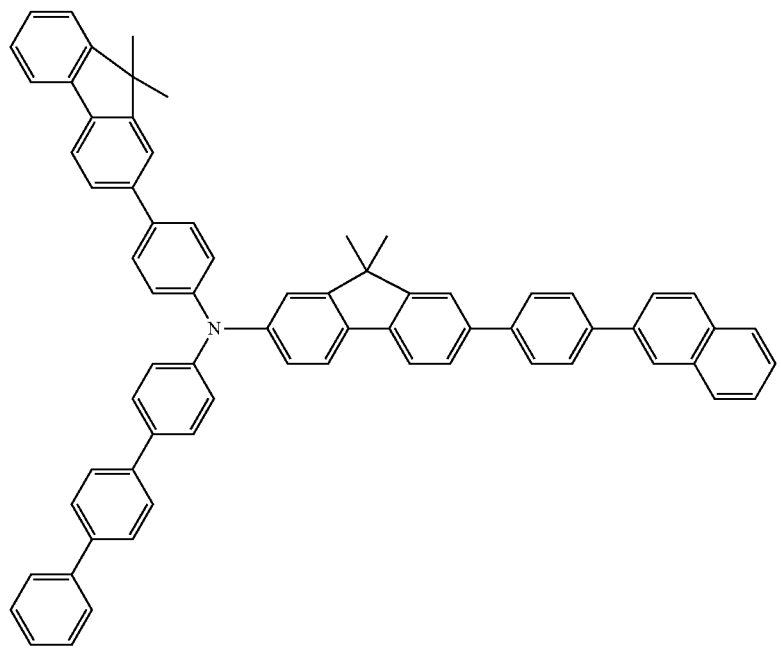
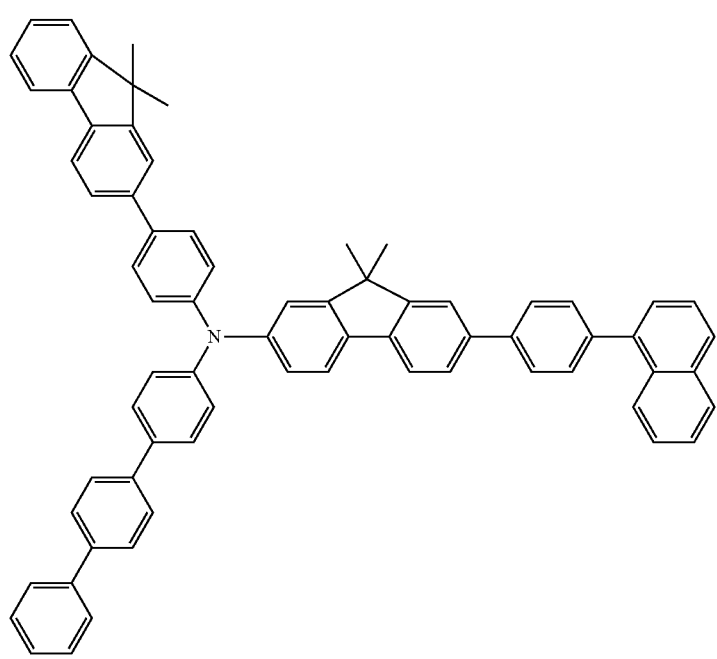

-continued
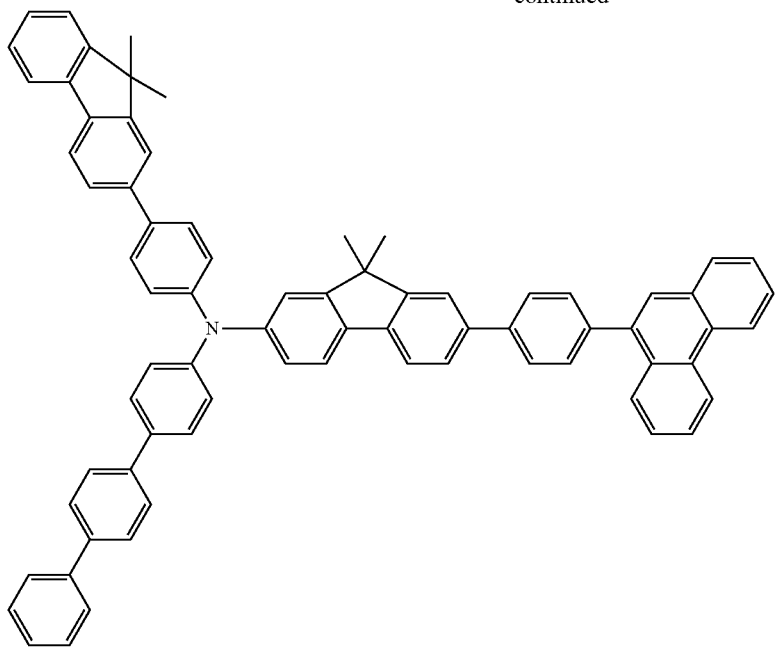
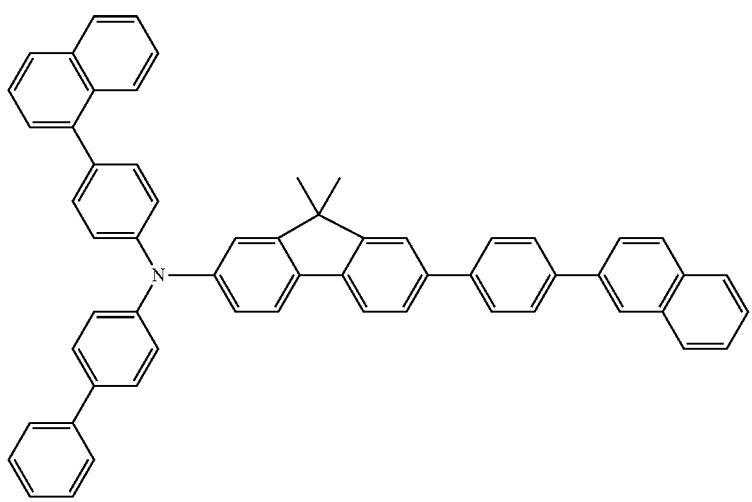
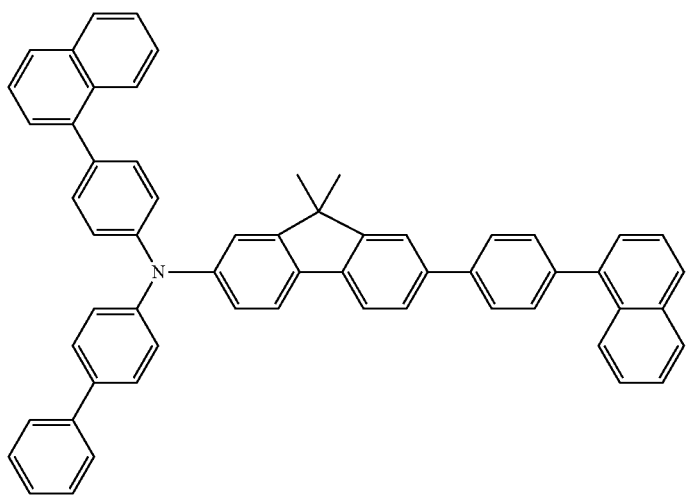

-continued
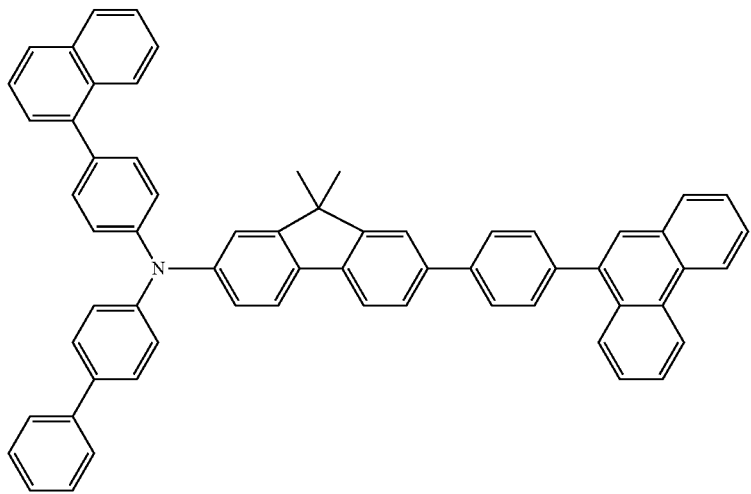
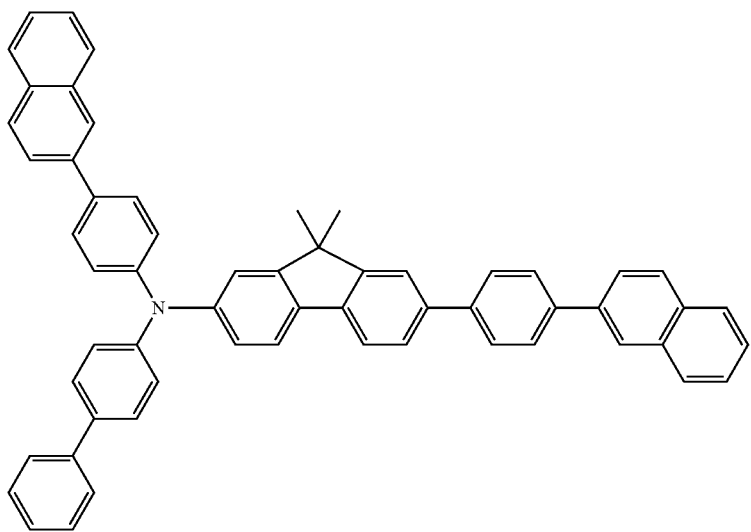
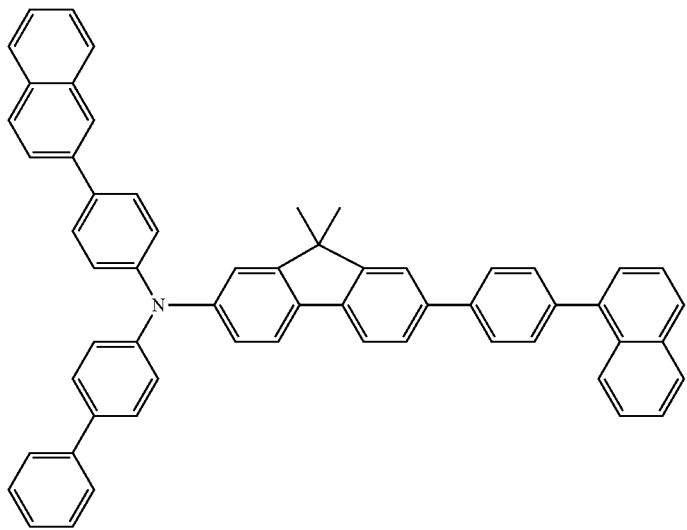

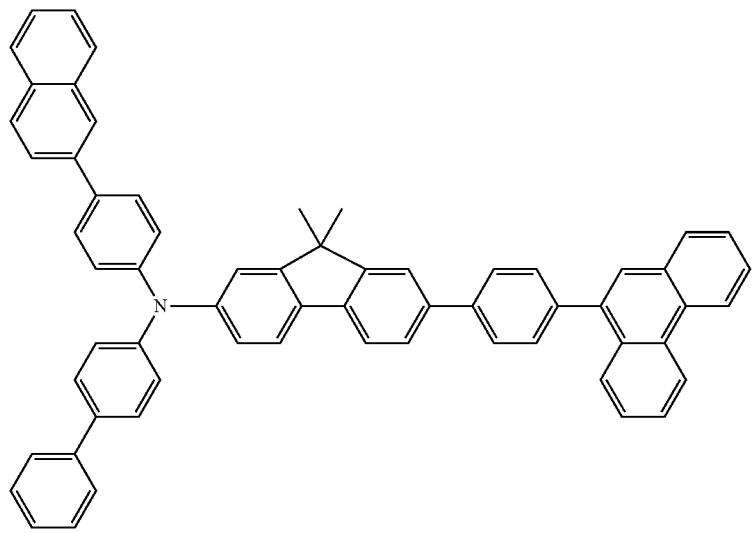
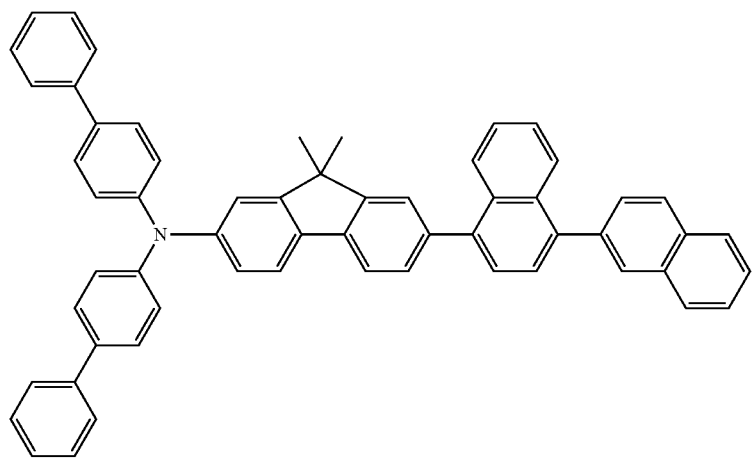
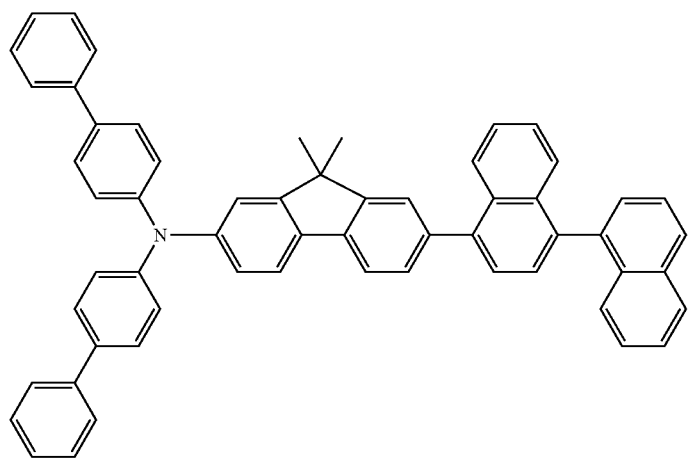

-continued

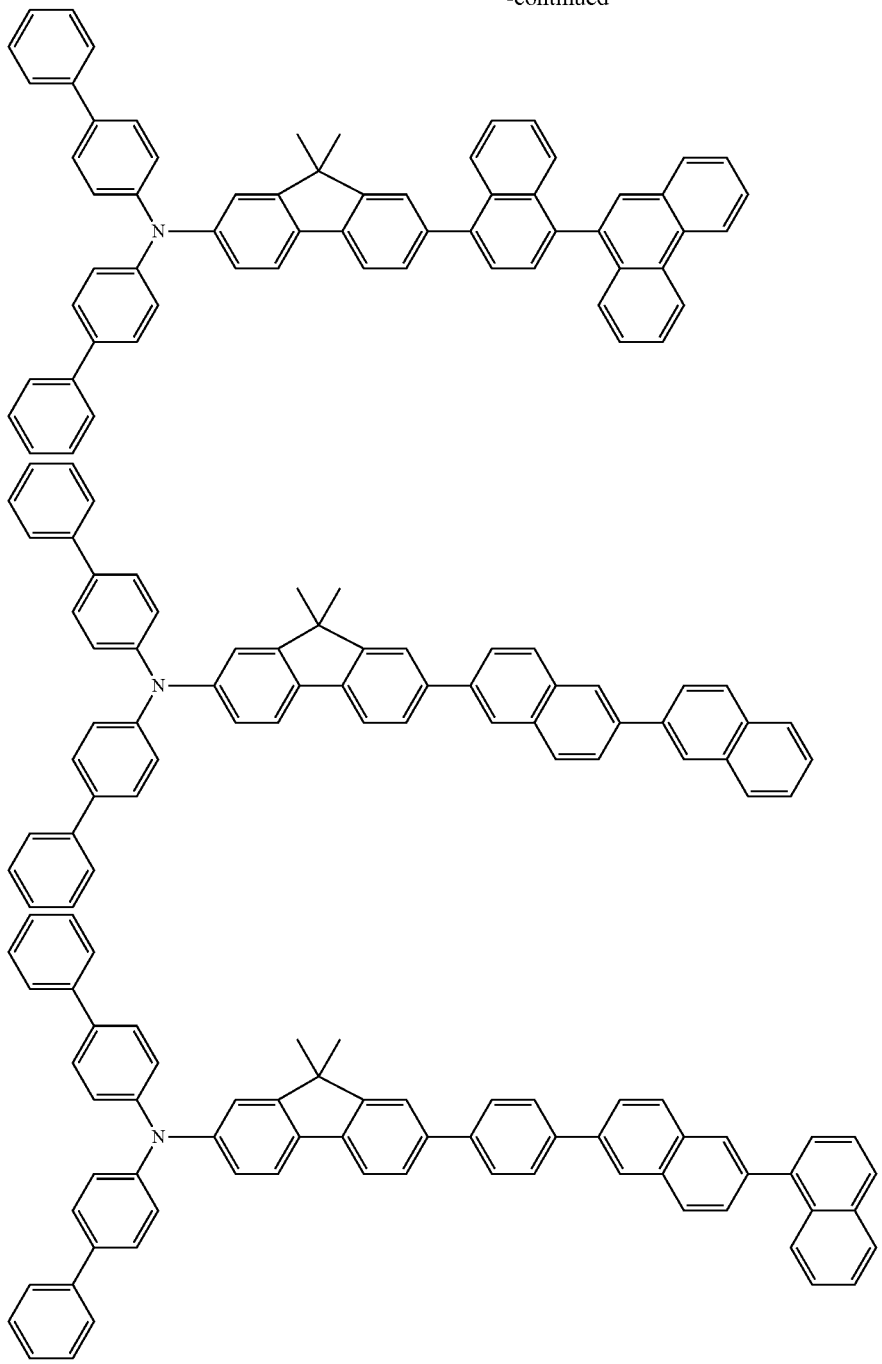

The aromatic amine derivative represented by the formula (1) of the present invention is used with preference as a material for organic electroluminescent elements. An organic electroluminescent element of the present invention has one or more organic thin film layers, including a light emitting layer, between a cathode and an anode, and at least one layer of the organic thin film layers contains any of the aromatic amine derivatives described above. In the organic electroluminescent element of the present invention, an aromatic amine derivative represented by the formula (1) is incorporated preferably into the hole injection layer or the hole transport layer.

Representative element configurations of the organic electroluminescent element of the present invention include the following configurations. Among these, the configuration of item (8) is usually used with preference, but the element configuration is not intended to be limited to these.

(1) Anode/light emitting layer/cathode
(2) Anode/hole injection layer/light emitting layer/cathode
(3) Anode/light emitting layer/electron injection layer/cathode
(4) Anode/hole injection layer/light emitting layer/electron injection layer/cathode
(5) Anode/organic semiconductor layer/light emitting layer/cathode (6) Anode/organic semiconductor layer/electron barrier layer/light emitting layer/cathode (7) Anode/organic semiconductor layer/light emitting layer/adhesion improving layer/cathode (8) Anode/hole injection layer/hole transport layer/light emitting layer/electron injection layer/cathode (9) Anode/insulating layer/light emitting layer/insulating layer/cathode

(10) Anode/inorganic semiconductor layer/insulating layer/light emitting layer/insulating layer/cathode

(11) Anode/organic semiconductor layer/insulating layer/light emitting layer/insulating layer/cathode

(12) Anode/insulating layer/hole injection layer/hole transport layer/light emitting layer/insulating layer/cathode

(13) Anode/insulating layer/hole injection layer/hole transport layer/light emitting layer/electron injection layer/cathode <Translucent Substrate>

The organic electroluminescent element of the present invention is produced by laminating, on a translucent substrate, a plural number of layers having the various layer configurations. The translucent substrate as used herein is a substrate that supports the organic electroluminescent element, and a smooth substrate having a transmittance of 50% or greater for light in the visible region in the wavelength range of 400 to 700 nm is preferred. Specific examples include a glass plate, a polymer plate, and the like. Particularly, examples of the glass plate include soda lime glass, barium/strontium-containing glass, lead glass, aluminosilicate glass, borosilicate glass, barium borosilicate glass, quartz, and the like. Furthermore, examples of the polymer plate include polycarbonate, acrylic, polyethylene terephthalate, polyether sulfide, polysulfone, and the like.

<Anode>

As the electroconductive material that is used for the anode of the organic electroluminescent element of the present invention, a material having a work function of greater than 4 eV is suitable. Examples that can be used include carbon, aluminum, vanadium, iron, cobalt, nickel, tungsten, silver, gold, platinum, palladium and the like, and alloys thereof; metal oxides such as tin oxide and indium oxide, which are used in ITO substrates and NESA substrates; and organic electroconductive resins such as polythiophene and polypyrrole.

<Cathode>

As the electroconductive material that is used for the cathode, a material having a work function of less than 4 eV is suitable. Examples that can be used include, but are not limited to, magnesium, calcium, tin, lead, titanium, yttrium, lithium, ruthenium, manganese, aluminum, lithium fluoride, and the like, and alloys thereof. Representative examples of the alloys include magnesium/silver, magnesium/indium, lithium/aluminum, and the like, but the examples are not limited to these. The ratio of such an alloy is controlled by the temperature of the deposition source, the atmosphere, the degree of vacuum, and the like, and an appropriate ratio is selected. If necessary, the anode and the cathode may be respectively formed to have a layer configuration with two or more layers.

The cathode can be produced by forming a thin film of the electroconductive material mentioned above, by a method such as deposition or sputtering.

In the case of extracting the light emitted from the light emitting layer through the cathode, the transmittance of the cathode for the emitted light is preferably adjusted to be greater than 10%. Furthermore, the sheet resistance of the cathode is preferably several hundred ohms per square or less, and the film thickness is usually 10 nm to 1 µm, and preferably 50 to 200 nm.

<Insulating Layer>

The organic electroluminescent element is prone to have pixel defects due to leakage or short circuit, because an electric field is applied to an ultrathin film. In order to prevent this, it is preferable to insert an insulating thin film layer between a pair of electrodes. Examples of the material that is used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. Mixtures or laminates of these materials may also be used.

<Light Emitting Layer>

The light emitting layer of the organic electroluminescent element combines the following functions of (1) to (3): (1) Injection function: a function by which holes can be injected from an anode or a hole injection layer, and electrons can be injected from a cathode or an electron injection layer, when an electric field is applied; (2) Transport function: a function of transferring injected charges (electrons and holes) by means of the force of an electric field; and (3) Light emission function: a function of providing a place for the recombination of electrons and holes and leading this provision to light emission.

The light emitting layer may have a difference between the ease of injection of holes and the ease of injection of electrons, and may also have a difference in the extent of transporting ability that is represented by the mobility of holes and electrons. Whatsoever, it is preferable to use a light emitting layer capable of transferring any one charge.

In the plural number of layers, if necessary, other known light emitting material, doping materials, hole injecting materials and electron injection material can also be used in addition to the aromatic amine derivative of the present invention. In the organic electroluminescent element, a decrease in luminance or service life due to quenching can be prevented by adopting a multilayer structure for the organic thin film layer. If necessary, a light emitting material, a doping material, a hole injecting material or an electron injecting material can be used in combination. Furthermore, depending on the doping material, an improvement in the light emission luminance or the luminous efficiency, or red or blue light emission may also be achieved.

The light emitting layer of the organic electroluminescent element of the present invention may contain any one or both of a styrylamine compound and an arylamine compound, as the doping material of the light emitting layer. When the doping materials mentioned above are used to form a light emitting layer, an organic electroluminescent element having high luminous efficiency and excellent color purity can be produced.

Examples of the host material or doping material that can be used in combination with the aromatic amine derivative of the present invention in the light emitting layer include, but are not limited to, fused-ring polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene and 1,4-bis(9'-ethynylanthracenyl)benzene, and derivatives thereof; organometallic complexes such as tris(8-quinolinolato)aluminum and bis-(2-methyl-8-quinolinolato)-4-(phenylphenolinato)aluminum;

triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamic acid ester derivatives, diketopyrrolopyrrole derivatives, acridone derivatives, quinacridone derivatives, and the like.

Furthermore, the light emitting layer, the hole injection layer and the electron injection layer may be respectively formed to have a layer configuration with two or more layers. At that time, in the case of the hole injection layer, a layer that injects holes from the electrode is referred to as a "hole injection layer", and a layer that receives holes from the hole injection layer and transports the holes to the light emitting layer is referred to as a "hole transport layer". Similarly, in the case of the electron injection layer, a layer that injects electrons from the electrode is referred to as an "electron injection layer", and a layer that receives electrons from the electron injection layer and transports the electrons to the light emitting layer is referred to as an "electron transport layer". These respective layers are selected and used based on various factors such as the energy level of the material, heat resistance, and adhesiveness to organic layers or to metal electrodes.

<Hole Injection Layer and Hole Transport Layer>

The hole injection layer and the hole transport layer are layers that assist with hole injection into the light emitting layer and transport holes to the light emission region, and these layers have high hole mobility and usually have ionization energy as small as 5.6 eV or less. The hole injecting material or hole transporting material that forms or is incorporated into such a hole injection layer or hole transport layer, is preferably a material which transports holes to the light emitting layer at a lower electric field intensity, and is more preferably a material which gives, for example, a hole mobility of at least $10^{-4}$ cm$^2$/Vs when an electric field of $10^4$ to $10^6$ V/cm is applied.

The aromatic amine derivative of the present invention is particularly preferably used in the hole injection layer and/or hole transport layer, but may be used only in the hole transport layer, or may be used only in the hole injection layer. Furthermore, it is also acceptable to form the hole injection layer and/or hole transport layer using the aromatic amine derivative of the present invention alone, or may also be used in mixture with other materials.

When the aromatic amine derivative of the present invention is used in both the hole transport layer and the hole injection layer, the aromatic amine derivative that is used in the hole transport layer and the aromatic amine derivative of the present invention that is used in the hole injection layer may be identical or different.

As the aromatic amine derivative to be used in the hole transport layer, an aromatic amine derivative in which Ar$_1$ in the formula (1) represents the organic group A, and Ar$_2$ and Ar$_3$ each independently represent the organic group B represented by the formula (5) or (6), is more preferred because the ionization energy value is close to the ionization energy value of the host material used in the light emitting layer, and the hole injection from the hole transport layer to the light emitting layer is promoted.

As the aromatic amine derivative to be used in the hole injection layer, an aromatic amine derivative in which Ar$_1$ to Ar$_3$ in the formula (1) each independently represent the organic group A, is more preferred because the ionization energy value is close to the ionization energy value of the anode, and the hole injection from the anode to the hole injection layer is promoted.

An aromatic amine derivative in which Ar$_1$ and Ar$_2$ in the formula (1) each independently represent the organic group A, and Ar$_3$ represents the organic group B represented by the formula (5) or (6), may be used with preference in any of the hole injection layer and the hole transport layer, because the ionization energy value adopts a value intermediate to the ionization energy value of the anode and the ionization energy value of the host material.

In addition, the organic electroluminescent element of the present invention is preferably such that the organic thin film layer has a hole transport layer and a hole injection layer, and an aromatic amine derivative in which Ar$_1$ and Ar$_2$ in the formula (1) both represent the organic group A, and also Ar$_3$ represents the organic group B represented by any one of the formulas (5) to (7), is contained respectively in the hole transport layer and the hole injection layer, because the ionization energy values of the hole injection layer and the hole transport layer are close to each other, and the hole injection barrier is lowered.

The organic electroluminescent element of the present invention is preferably such that an aromatic amine derivative in which Ar$_1$ and Ar$_2$ in the formula (1) both represent the organic group A, and also Ar$_3$ represents the organic group B represented by any of the formulas (5) to (7), is contained in the hole transport layer, and an aromatic amine derivative in which Ar$_1$ to Ar$_3$ each independently represent the organic group A is contained in the hole injection layer, because when the hole injection layer and the hole transport layer form a laminated structure, holes are injected stepwise from the anode to the light emitting layer, and the hole injection barrier is lowered.

The organic electroluminescent element of the present invention is preferably such that an aromatic amine derivative in which Ar$_1$ in the formula (1) represents the organic group A, and also Ar$_2$ and Ar$_3$ both represent the organic group B represented by any of the formulas (5) to (7) is contained in the hole transport layer, and an aromatic amine derivative in which Ar$_1$ and Ar$_2$ both represent the organic group A, and also Ar$_3$ represents the organic group B represented by any of the formulas (5) to (7) is contained in the hole injection layer, because when the hole injection layer and the hole transport layer form a laminated structure, holes are injected stepwise from the anode to the light emitting layer, and the hole injection barrier is lowered.

Furthermore, the organic electroluminescent element of the present invention is preferably such that an aromatic amine derivative in which Ar$_1$ in the formula (1) represents the organic group A, and also Ar$_2$ and Ar$_3$ both represent the organic group B represented by any of the formulas (5) to (7) is contained in the hole transport layer, and an aromatic amine derivative in which Ar$_1$ to Ar$_3$ each independently represent the organic group A is contained in the hole injection layer, because when the hole injection layer and the hole transport layer form a laminated structure, holes are injected stepwise from the anode to the light emitting layer, and the hole injection barrier is lowered.

In regard to other materials that are combined with or mixed with the aromatic amine derivative of the present invention and form the hole injection/transport layer, there are no particular limitations on the materials as long as the materials have the preferred properties described above. Conventionally, any material can be selected for use from those materials that are used as a charge transporting material for holes in photoconductor materials, or any known materials that are used in the hole injection/transport layer of organic electroluminescent elements. In the present specification, a material which has a hole transporting ability and can be used in the hole transport zone, is referred to as a "hole transporting material". Furthermore in the present specification, a material which has a hole injecting ability and can be used in the hole injection zone, is referred to as a "hole injecting material".

Specific examples of the material for the hole injection layer and the hole transport layer, other than the aromatic amine derivative of the present invention, include phthalocyanine derivatives, naphthalocyanine derivatives, porphyrin derivatives, oxazole derivatives, triazole derivatives, oxadiazole derivatives, imidazole derivatives, polyarylalkane derivatives, pyrazoline derivatives, pyrazolone derivatives, phenylenediamine derivatives, arylamine derivatives, aminosubstituted chalcone derivatives, styrylanthracene derivatives, fluorenone derivatives, hydrazone derivatives, stilbene derivatives, silazane derivatives, polysilane-based copolymers, aniline-based copolymers, and electroconductive polymer oligomers (particularly, thiophene oligomers), and the like. Preferred examples include porphyrin compounds, aromatic tertiary amine compounds, and styrylamine compounds, and particularly preferred examples include aromatic tertiary amine compounds.

Furthermore, examples of the material for the hole injection layer and the hole transport layer, other than the aromatic amine derivative of the present invention, include compounds having two fused aromatic rings in the molecule, such as 4,4'-bis(N-(1-naphthyl)-N-phenylamino)biphenyl (hereinafter, abbreviated to NPD), and 4,4',4"-tris(N-(3-methylphenyl)-N-phenylamino)triphenylamine (hereinafter, abbreviated to MTDATA) in which three triphenylamine units are linked in a star-burst form.

Furthermore, the material for the hole injection layer and the hole transport layer, other than the aromatic amine derivative of the present invention, may be a nitrogen-containing heterocyclic ring derivative represented by the following formula:

[Chemical formula 24]

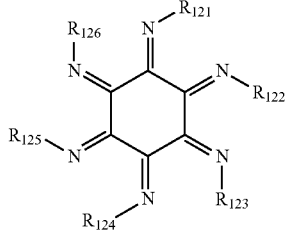

In the formula shown above, $R_{121}$ to $R_{126}$ each represent any of a substituted or unsubstituted alkyl group, a substituted or unsubstituted aryl group, a substituted or unsubstituted aralkyl group, and a substituted or unsubstituted heterocyclic group. Each of $R_{121}$ to $R_{126}$ may be identical with or different from the others. Furthermore, $R_{121}$ and $R_{122}$, $R_{123}$ and $R_{124}$, $R_{125}$ and $R_{126}$, $R_{121}$ and $R_{126}$, $R_{122}$ and $R_{123}$, or $R_{124}$ and $R_{125}$ may be joined together to form a fused ring.

Furthermore, a compound represented by the following formula can also be used:

[Chemical formula 25]

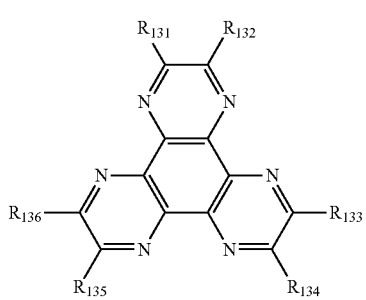

In the formula shown above, $R_{131}$ to $R_{136}$ each represent any substituent, and preferred examples include electron-withdrawing groups such as a cyano group, a nitro group, a sulfonyl group, a carbonyl group, a trifluoromethyl group, and halogen atoms.

Acceptor materials, which are represented by these materials, may also be used as the hole injecting material or the hole transporting material. Specific examples thereof include the same compounds as described above.

Among the hole injecting materials that can be used for the organic electroluminescent element of the present invention, more effective hole injecting materials are aromatic tertiary amine derivatives and phthalocyanine derivatives.

Examples of the aromatic tertiary amine derivatives include, but are not limited to, triphenylamine, tritolylamine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and the like, and oligomers and polymers having skeletons of these aromatic tertiary amines.

Examples of the phthalocyanine (Pc) derivatives include, but are not limited to, phthalocyanine derivatives such as $H_2Pc$, $CuPc$, $CoPc$, $NiPc$, $ZnPc$, $PdPc$, $FePc$, $MnPc$, $ClAlPc$, $ClGaPc$, $ClInPc$, $ClSnPc$, $Cl_2SiPc$, $(HO)AlPc$, $(HO)GaPc$, $VOPc$, $TiOPc$, $MoOPc$, and $GaPc-O-GaPc$; and naphthalocyanine derivatives. Furthermore, the organic electroluminescent element of the present invention is preferably constructed by forming a layer containing these aromatic tertiary amine derivatives and/or phthalocyanine derivatives, for example, the hole transport layer or hole injection layer, between the light emitting layer and the anode.

<Electron Injection/Transport Layer>

Next, the electron injection layer/transport layer will be described. The electron injection layer/transport layer is a layer that assists with the injection of electrons into the light emitting layer and transports the electrons to the light emission region, and has high electron mobility. Within this electron injection layer, a layer formed of a material having particularly high adhesiveness to the cathode may be provided as an adhesion improving layer.

Furthermore, it is known that in an organic electroluminescent element, since emitted light is reflected by an electrode (in this case, a cathode), the emitting light extracted directly from the anode interferes with the emitted light extracted via reflection by an electrode. In order to efficiently utilize this interference effect, the electron transport layer is appropriately selected to have a thickness of several nanometers (nm) to several micrometers (µm). However, in the case of having a particularly large layer thickness, it is preferable that when an electric field of $10^4$ to $10^6$ V/cm is applied, the electron mobility of the electron transport layer be $10^{-5}$ cm$^2$/Vs or greater, in order to avoid an increase in voltage.

Specific examples of the material that is used in the electron injection layer include, but are not limited to, fluorenone, anthraquinodimethane, diphenoquinone, thiopyrane dioxide, oxazole, oxadiazole, triazole, imidazole, perylenetetracarboxylic acid, fluorenylidenemethane, anthraquinodimethane, anthrone, and the like, and derivatives thereof. Furthermore, when an electron accepting material is added to the hole injecting material, and an electron donating material to the electron injecting material, the materials can be sensitized.

Electron injecting materials that are more effective for the organic electroluminescent element of the present invention are metal complex compounds and nitrogen-containing 5-membered ring derivatives. Examples of the metal complex compounds include, but are not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(1-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like.

The nitrogen-containing 5-membered derivatives as the electron injecting material are preferably, for example, oxazole, thiazole, oxadiazole, thiadiazole, and triazole derivatives. Specific examples include, but are not limited to, 2,5-bis(1-phenyl)-1,3,4-oxazole, dimethyl-POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, 1,4-bis[2-(5-phenyltriazolyl)]benzene, and the like.

In the organic electroluminescent element of the present invention, at least one kind of a light emitting material, a doping material, a hole injecting material and an electron injecting material may be incorporated in the light emitting layer, together with the aromatic amine derivative represented by the formula (1). Furthermore, for an enhancement of the stability against temperature, humidity, atmosphere and the like, of the organic electroluminescent element obtained by the present invention, a protective layer can also be provided on the surface of the element, or the whole element can be protected with a silicone oil, a resin or the like.

In order to make the organic electroluminescent element of the present invention to emit light with high efficiency, it is preferable to make at least one surface to be sufficiently transparent to the emission wavelength region of the element. Furthermore, it is also desirable to have a transparent substrate. A transparent electrode is constructed by a method such as deposition or sputtering using the electroconductive materials described above, so as to secure predetermined translucency. The electrode on the light emitting surface side is preferably adjusted to have a light transmittance of 10% or greater. There are no particular limitations on the substrate as long as the material has mechanical and thermal strength and is transparent, but examples include a glass substrate and a transparent resin film. Examples of the transparent resin film include films of polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoro ethylene-perfluoro alkyl vinyl ether copolymer, polyvinyl fluoride, a tetrafluoroethylene-ethylene copolymer, a tetrafluoro ethylene-hexafluoropropylene copolymer, polychlorotrifluoroethylene, polyvinylidene fluoride, polyester, polycarbonate, polyurethane, polyimide, polyether imide, polyimide, polypropylene, and the like.

The formation of the various layers of the organic electroluminescent element of the present invention can be carried out by applying any of dry film-forming methods such as vacuum deposition, sputtering, plasma and ion plating, and wet film-forming methods such as spin coating, dipping and flow coating. There are no particular limitations on the film thickness, but it is necessary to set the layers to have appropriate thicknesses. Tf the thickness is too large, a large applied voltage is needed in order to obtain a certain light output, and thus the efficiency becomes poor. If the thickness is too small, pinholes and the like are generated, and even if an electric field is applied, sufficient light emission luminance cannot be obtained. Usually, the layer thickness is suitably in the range of 5 nm to 10 μm, but is more preferably in the range of 10 nm to 0.2 μm.

In the case of a wet film-forming method, a material which forms each layer is dissolved or dispersed in an appropriate solvent such as ethanol, chloroform, tetrahydrofuran or dioxane, and thereby a thin film is formed. The solvent may be any solvent. As a solution appropriate for such a wet film-forming method, an organic EL material-containing solution which contains the aromatic amine derivative of the present invention and a solvent can be used as an organic EL material. Furthermore, for any organic thin film layer, an appropriate resin or additive may be used for the purpose of improving film-forming properties, preventing pinholes in the film, and the like. Examples of the resin that can be used include insulating resins such as polystyrene, polycarbonate, polyallylate, polyester, polyamide, polyurethane, polysulfone, polymethyl methacrylate, polymethyl acrylate and cellulose, and copolymers thereof; photoconductive resins such as poly-N-vinylcarbazole and polysilane; and electroconductive resins such as polythiophene and polypyrrole. Furthermore, examples of the additive include an oxidation inhibitor, an ultraviolet absorber, a plasticizer, and the like.

<Method for Producing Organic Electroluminescent Element>

An organic electroluminescent element can be produced by forming an anode, a light emitting layer, a hole injection/transport layer as necessary, and an electron injection/transport layer as necessary, by the various materials and layer forming method exemplified above, and further forming a cathode. Furthermore, an organic electroluminescent element can also be produced from a cathode to an anode, in an order reverse to the order described above.

A production example for an organic electroluminescent element having a configuration in which an anode/a hole injection layer/a light emitting layer/an electron injection layer/a cathode are sequentially provided on a translucent substrate, will be described below. First, a thin film made of an anode material is formed on an appropriate translucent substrate, to have a thickness of 1 μm or less (preferably, in the range of 10 to 200 nm) by a method such as deposition or sputtering, and thereby an anode is produced. Subsequently, a hole injection layer is provided on this anode. Formation of the hole injection layer can be carried out by a method such as a vacuum deposition method, a spin coating method, a casting method or an LB method as described above; however, from the viewpoint that a uniform film can be easily obtained, pinholes are not easily formed, and the like, it is preferable to form the hole injection layer by a vacuum deposition method. When the hole injection layer is formed by a vacuum deposition method, the deposition conditions may vary with the compound used (material for the hole injection layer), the crystal structure of the intended hole injection layer, the recombination structure or the like. However, in general, it is preferable to appropriately select the deposition source temperature to be in the range of 50° C. to 450° C., the degree of vacuum to be in the range of $10^{-7}$ to $10^{-3}$ Torr, the deposition rate to be in the range of 0.01 to 50 nm/sec, the substrate temperature to be in the range of −50° C. to 300° C., and the layer thickness to be in the range of 5 nm to 5 μm.

In addition, the light emitting layer, the electron injection layer and the anode may be formed by any method, and there are no particular limitations. Examples of the method of formation include a vacuum deposition method, an ionization deposition method, solution coating methods (for example, a spin coating method, a casting method, a dip coating method, a bar coating method, a roll coating method, a Langmuir-Blodgett method, and an inkjet method), and the like.

The organic electroluminescent element of the present invention can be used in planar emitters such as the flat panel display of wall TV's; light sources for photocopiers, printers, the back light of liquid crystal displays, meters and gauges, or the like; display panels; signal lights; and the like. Furthermore, the material of the present invention can also be used not only in the field of organic electroluminescent elements, but also in the fields of electrophotographic photoreceptors, photoelectric conversion elements, solar cells, image sensors, and the like.

EXAMPLES

Hereinafter, the present invention will be described in more detail based on Synthetic Examples and Examples.

The structural formulas of Intermediates 1 to 14 that are produced in Synthetic Examples 1 to 14 are as follows.

[Chemical formula 26]

Intermediate 1

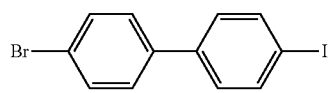

Intermediate 2

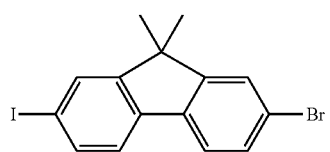

Intermediate 3

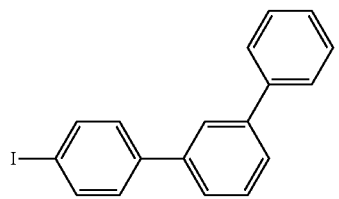

Intermediate 4

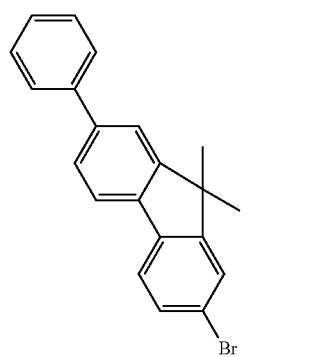

-continued

Intermediate 5

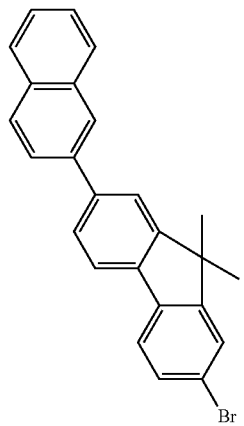

Intermediate 6

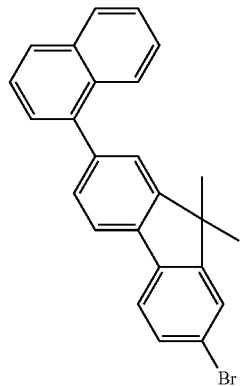

Intermediate 7

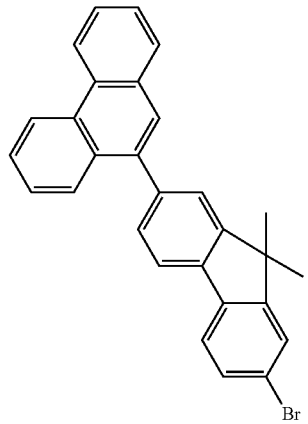

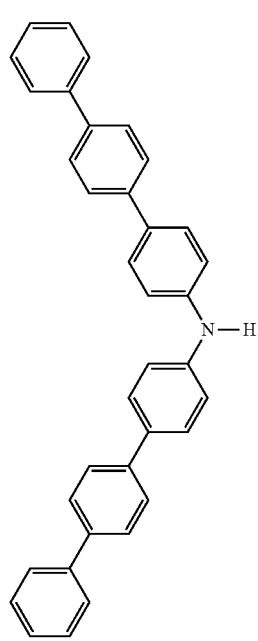
Intermediate 8
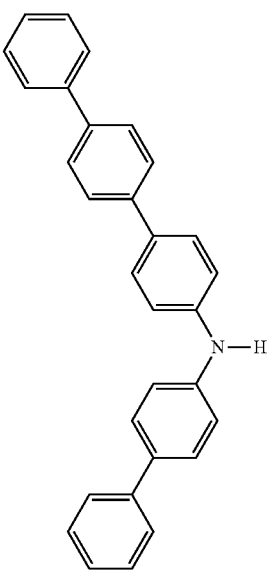
Intermediate 10
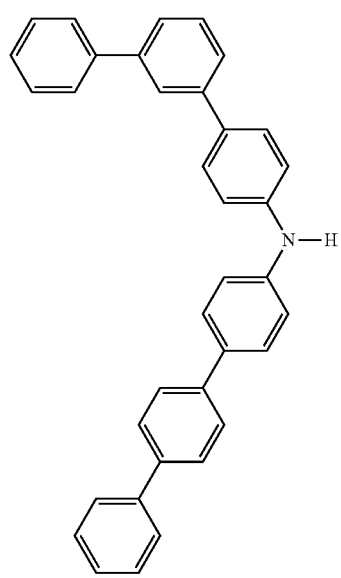
Intermediate 9
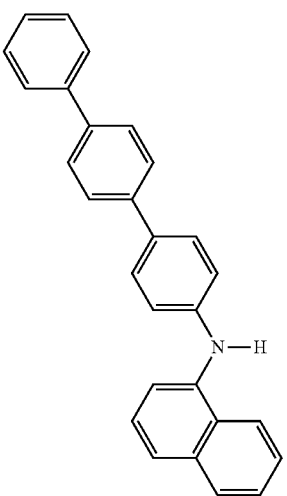
Intermediate 11

-continued

Intermediate 12

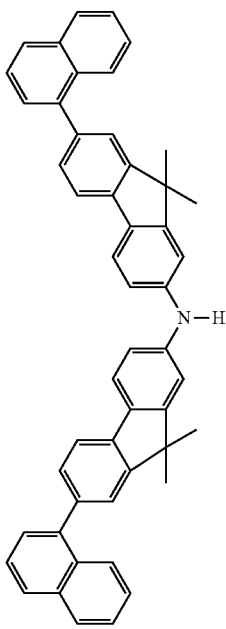

Intermediate 13

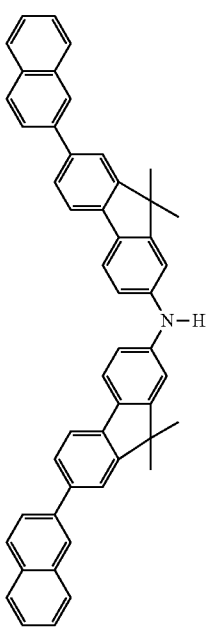

-continued

Intermediate 14

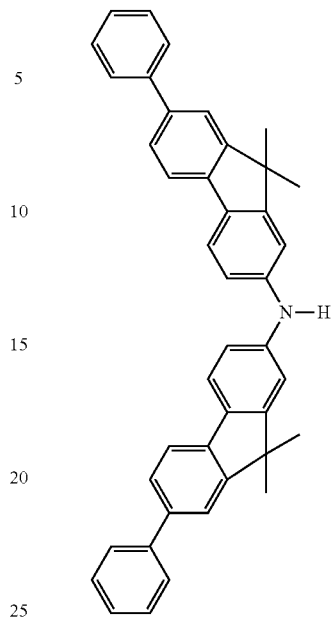

Synthetic Example 1

Synthesis of Intermediate 1

Under an argon gas stream, 47 g of 4-bromobiphenyl, 23 g of iodine, 9.4 g of periodic acid dihydrate, 42 ml of water, 360 ml of acetic acid, and 11 ml of sulfuric acid were introduced into a 1000-mL three-necked flask, and the resulting mixture was stirred for 30 minutes at 65° C. and then was allowed to react for 6 hours at 90° C. The reaction product was injected into ice water, and the mixture was filtered. The filter cake was washed with water and then was washed with methanol. Thus, 67 g of a white powder was obtained. In a FD-MS analysis, main peaks were obtained at m/z=358 and 360 for $C_{12}H_8BrI=359$, and the white powder was identified as intermediate 1.

Synthetic Example 2

Synthesis of Intermediate 2

A reaction was carried out in the same manner as in Synthetic Example 1, except that 2-bromo-9,9-dimethylfluorene was used instead of 4-bromobiphenyl, and thus 61 g of a white powder was obtained. In a FD-MS analysis, main peaks were obtained at m/z=398 and 400 for $C_{15}H_{12}BrI=399$, and the white powder was identified as intermediate 2.

Synthetic Example 3

Synthesis of Intermediate 3

250 g of m-terphenyl (manufactured by Sigma-Aldrich Company), 50 g of hydroiodic acid dihydrate, 75 g of iodine, 750 ml of acetic acid, and 25 ml of concentrated sulfuric acid were introduced into a three-necked flask, and the resulting mixture was allowed to react for 3 hours at 70° C. After the reaction, 5 L of methanol was introduced therein, and then the mixture was stirred for one hour. This resultant was collected by filtration, and the crystals thus obtained were purified by

Synthetic Example 4

Synthesis of Intermediate 4

In an argon atmosphere, to 39.9 g (100 mmol) of intermediate 2, 12.4 g (105 mmol) of phenylboronic acid, 2.31 g (2.00 mmol) of tetrakis(triphenylphosphine)palladium(0), were added 300 ml of toluene and 150 ml of a 2 M aqueous solution of sodium carbonate, and the resulting mixture was heated to reflux for 10 hours.

After completion of the reaction, the mixture was immediately filtered, and then the aqueous layer was removed. The organic layer was dried over sodium sulfate, and then was concentrated. The residue was purified by silica gel column chromatography, and thus 28.3 g of white crystals were obtained (yield 81%). The white crystals were identified as intermediate 4 by a FD-MS analysis.

Synthetic Example 5

Synthesis of Intermediate 5

A reaction was carried out in the same manner as in Synthetic Example 4, except that 2-naphthylboronic acid was used instead of phenylboronic acid, and thus 30.2 g of a white powder was obtained. The white powder was identified as intermediate 5 by a FD-MS analysis.

Synthetic Example 6

Synthesis of Intermediate 6

A reaction was carried out in the same manner as in Synthetic Example 4, except that 1-naphthylboronic acid was used instead of phenylboronic acid, and thus 32.1 g of a white powder was obtained. The white powder was identified as intermediate 6 by a FD-MS analysis.

Synthetic Example 7

Synthesis of Intermediate 7

A reaction was carried out in the same manner as in Synthetic Example 4, except that 9-phenanthrenylboronic acid was used instead of phenylboronic acid, and thus 34.7 g of a white powder was obtained. The white powder was identified as intermediate 7 by a FD-MS analysis.

Synthetic Example 8

Synthesis of Intermediate 8

Under an argon gas stream, 30.7 g of 4-bromo-p-terphenyl, 24.3 g of 4-amino-p-terphenyl, 13.0 g of t-butoxysodium (manufactured by Hiroshima Wako Co., Ltd.), 460 mg of tris(dibenzylideneacetone)dipalladium(0) (manufactured by sigma-Aldrich Company), 210 mg of tri-t-butylphosphine, and 500 ml of dehydrated toluene were introduced, and the resulting mixture was allowed to react for 8 hours at 80° C. After cooling, 2.5 liters of water was added to the reaction product, and the mixture was filtered through Celite. The filtrate was extracted with toluene, and was dried over anhydrous magnesium sulfate. The resultant was concentrated under reduced pressure, and a crude product thus obtained was purified with a column and was recrystallized from toluene. The crystals were collected by filtration, and then were dried. Thus, 28.7 g of a pale yellow powder was obtained. The pale yellow powder was identified as intermediate 8 by a FD-MS analysis.

Synthetic Example 9

Synthesis of Intermediate 9

A reaction was carried out in the same manner as in Synthetic Example 8, except that intermediate 3 was used instead of 4-bromo-p-terphenyl, and thus 30.7 g of a white powder was obtained. The white powder was identified as intermediate 9 by a FD-MS analysis.

Synthetic Example 10

Synthesis of Intermediate 10

A reaction was carried out in the same manner as in Synthetic Example 8, except that 4-bromobiphenyl was used instead of 4-bromo-p-terphenyl, and thus 25.3 g of a white powder was obtained. The white powder was identified as intermediate 10 by a FD-MS analysis.

Synthetic Example 11

Synthesis of Intermediate 11

A reaction was carried out in the same manner as in Synthetic Example 8, except that 1-bromonaphthalene was used instead of 4-bromo-p-terphenyl, and thus 23.5 g of a white powder was obtained. The white powder was identified as intermediate 11 by a FD-MS analysis.

Synthetic Example 12

Synthesis of Intermediate 12

Under an argon gas stream, 22.8 g of benzamide (manufactured by Tokyo Chemical Industry Co., Ltd.), 83.8 g of intermediate 6, 6.6 g of copper(I) iodide (manufactured by Wako Pure Chemical Industries, Ltd.), 6.1 g of N,N'-dimethylethylenediamine (manufactured by Sigma-Aldrich company), 52.8 g of potassium carbonate (manufactured by Wako Pure Chemical Industries, Ltd.), and 480 ml of xylene were introduced into a 1000-ml three-necked flask, and the resulting mixture was allowed to react for 36 hours at 130° C. After cooling, the reaction mixture was filtered, and the filter cake was washed with toluene. The resultant was further washed with water and methanol, and then was dried. Thus, 92 g of a pale yellow powder was obtained.

25.0 g of the powder, 24.8 g of potassium hydroxide (manufactured by Wako Pure Chemical Industries, Ltd.), 21 ml of ion-exchanged water, 28 ml of xylene (manufactured by Wako Pure Chemical Industries, Ltd.), and 15 ml of EtOH (manufactured by Wako Pure Chemical Industries, Ltd.) were introduced into a three-necked flask, and the resulting mixture was refluxed for 36 hours. After completion of the reaction, the reaction mixture was extracted with toluene, and was dried over magnesium sulfate. The resultant was concentrated under reduced pressure, and the crude product thus obtained was purified with a column. The resultant was recrystallized from toluene, and the crystals were collected by filtration and dried. Thus, 11.2 g of intermediate 12 was obtained as a white powder.

Synthetic Example 13

Synthesis of Intermediate 13

A reaction was carried out in the same manner as in Synthetic Example 12, except that intermediate 5 was used instead of intermediate 6, and thus 10.8 g of a white powder was obtained. The white powder was identified as intermediate 13 by a FD-MS analysis.

Synthetic Example 14

Synthesis of Intermediate 14

A reaction was carried out in the same manner as in Synthetic Example 12, except that intermediate 4 was used instead of intermediate 6, and thus 9.2 g of a white powder was obtained. The white powder was identified as intermediate 14 by a FD-MS analysis.

The structural formulas of compounds HT1 to HT12, which are the aromatic amine derivatives of the present invention produced in Synthesis Examples 1 to 12, are as follows.

[Chemical formula 27]

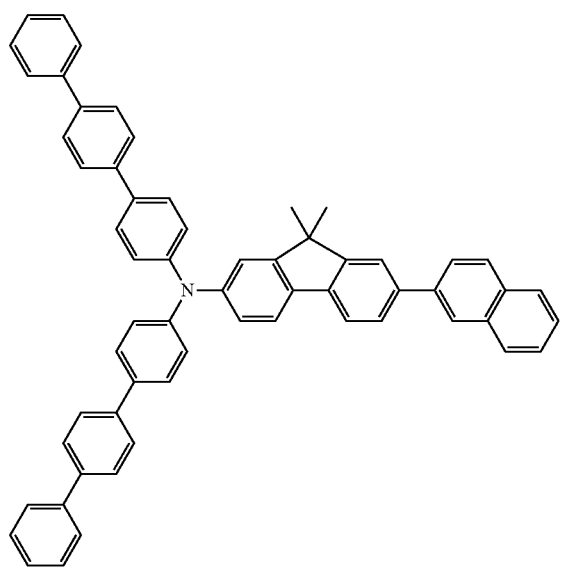

HT1

-continued

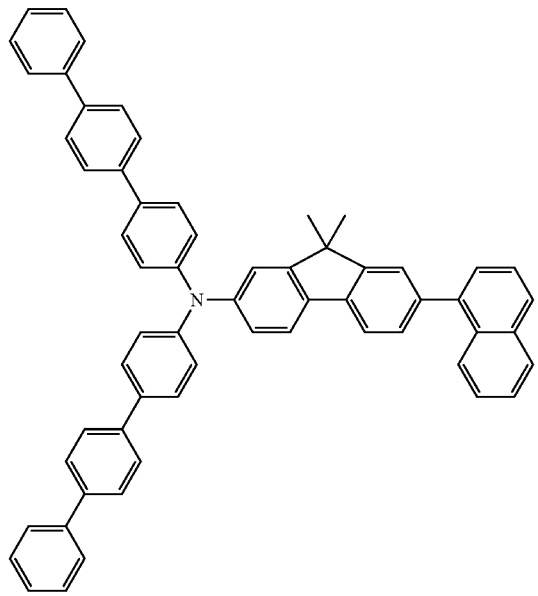

HT2

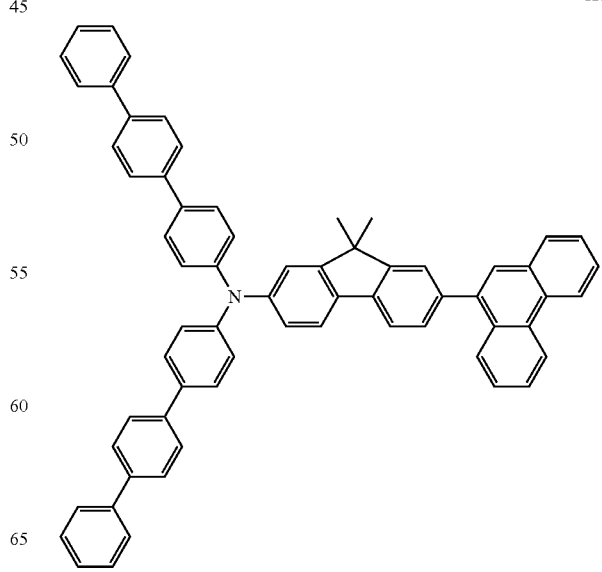

HT3

HT4
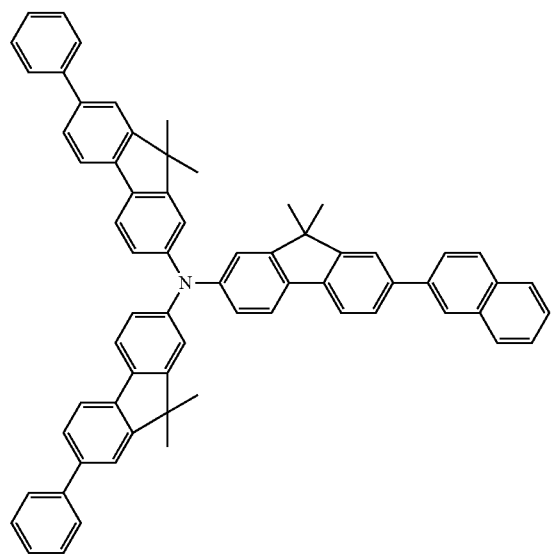
HT5
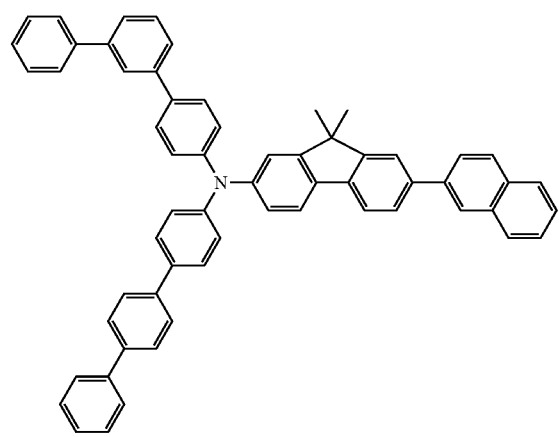
HT6
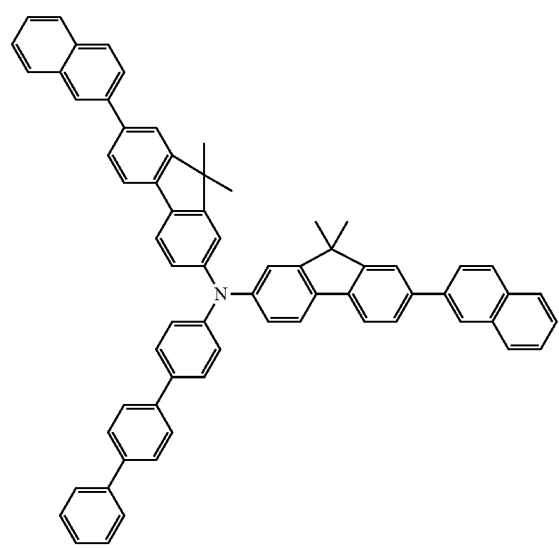
HT7
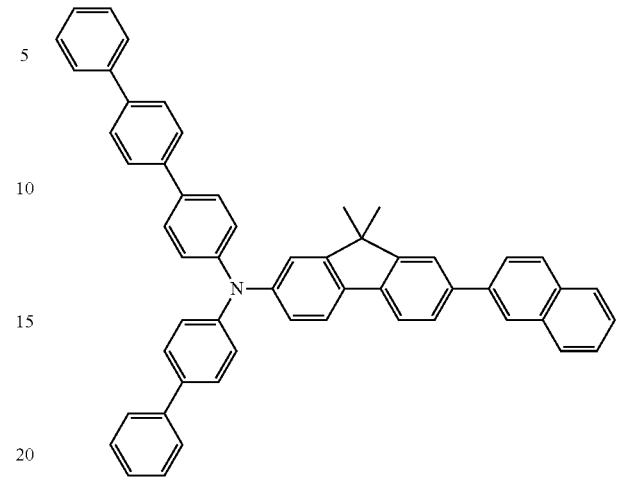
HT8
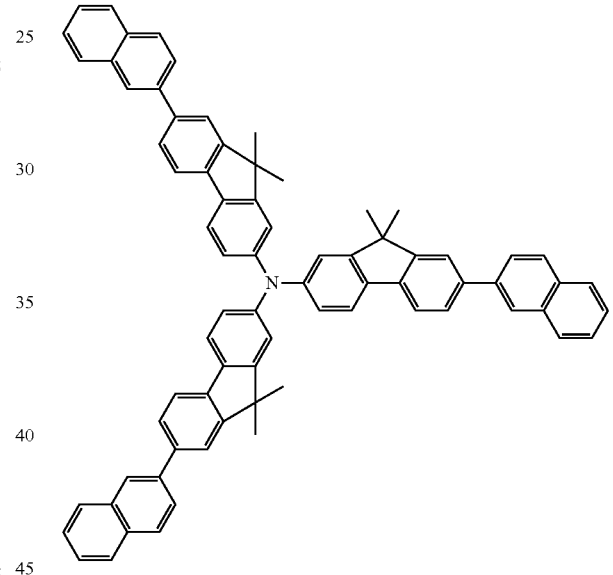
[Chemical formula 28]
HT9
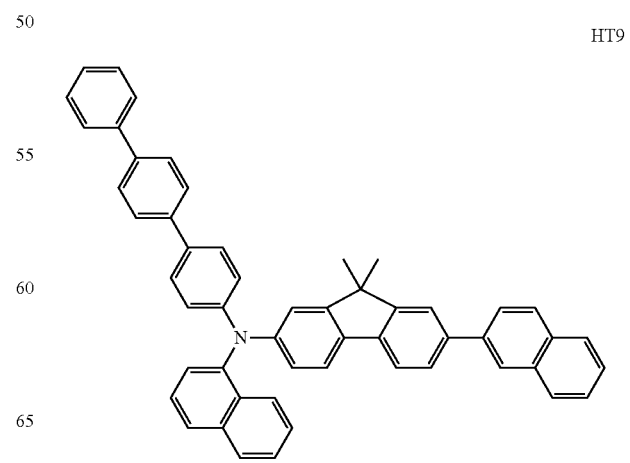

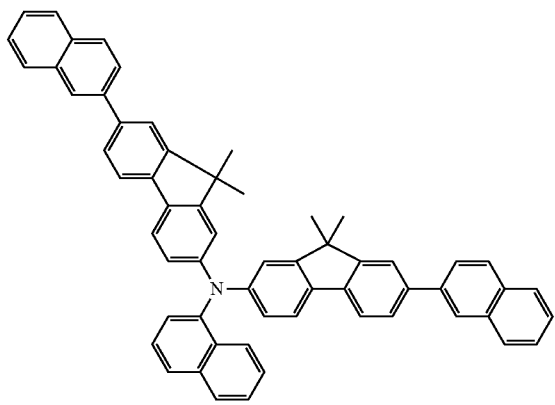

Synthesis Example 1

Synthesis of Compound HT1

Under an argon gas stream, 8.0 g of intermediate 5, 9.4 g of intermediate 8, 2.6 g of t-butoxysodium (manufactured by Hiroshima Wako Co., Ltd.), 92 mg of tris(dibenzylideneacetone)dipalladium(0) (manufactured by Sigma-Aldrich Company), 42 mg of tri-t-butylphosphine, and 100 ml of dehydrated toluene were introduced, and the resulting mixture was allowed to react for 8 hours at 80° C. After cooling, 500 ml of water was added thereto, and the mixture was filtered through Celite. The filtrate was extracted with toluene, and was dried over anhydrous magnesium sulfate. The resultant was concentrated under reduced pressure, and a crude product thus obtained was purified with a column and was recrystallized from toluene. The crystals were collected by filtration, and were dried. Thus, 8.6 g of a pale yellow powder was obtained. The pale yellow powder was identified as compound HT1 by a FD-MS (field desorption mass spectroscopy) analysis.

Synthesis Example 2

Synthesis of Compound HT2

A reaction was carried out in the same manner as in Synthesis Example 1, except that intermediate 6 was used instead of intermediate 5, and thus 9.1 g of a pale yellow powder was obtained. The pale yellow powder was identified as compound HT2 by a FD-MS analysis.

Synthesis Example 3

Synthesis of Compound HT3

A reaction was carried out in the same manner as in Synthesis Example 1, except that intermediate 7 was used instead of intermediate 5, and thus 8.2 g of a pale yellow powder was obtained. The pale yellow powder was identified as compound HT3 by a FD-MS analysis.

Synthesis Example 4

Synthesis of Compound HT4

A reaction was carried out in the same manner as in Synthesis Example 1, except that intermediate 14 was used instead of intermediate 8, and thus 10.1 g of a pale yellow powder was obtained. The pale yellow powder was identified as compound HT4 by a FD-MS analysis.

Synthesis Example 5

Synthesis of Compound HT5

A reaction was carried out in the same manner as in Synthesis Example 1, except that intermediate 9 was used instead of intermediate 8, and thus 9.8 g of a pale yellow powder was obtained. The pale yellow powder was identified as compound HT5 by a FD-MS analysis.

Synthesis Example 6

Synthesis of Compound HT6

A reaction was carried out in the same manner as in Synthesis Example 1, except that 4-bromo-p-terphenyl was used instead of intermediate 5 and intermediate 13 was used instead of intermediate 8, and thus 10.4 g of a pale yellow powder was obtained. The pale yellow powder was identified as compound HT6 by a FD-MS analysis.

Synthesis Example 7

Synthesis of Compound HT7

A reaction was carried out in the same manner as in Synthesis Example 1, except that intermediate 10 was used instead of intermediate 8, and thus 7.6 g of a pale yellow powder was obtained. The pale yellow powder was identified as compound HT7 by a FD-MS analysis.

Synthesis Example 8

Synthesis of Compound HT8

A reaction was carried out in the same manner as in Synthesis Example 1, except that intermediate 13 was used instead of intermediate 8, and thus 12.1 g of a pale yellow powder was obtained. The pale yellow powder was identified as compound HT8 by a FD-MS analysis.

Synthesis Example 9

Synthesis of Compound HT9

A reaction was carried out in the same manner as in Synthesis Example 1, except that intermediate 11 was used instead of intermediate 8, and thus 7.4 g of a pale yellow powder was obtained. The pale yellow powder was identified as compound HT9 by a FD-MS analysis.

Synthesis Example 10

Synthesis of Compound HT10

A reaction was carried out in the same manner as in Synthesis Example 1, except that 1-bromonaphthalene was used instead of intermediate 5 and intermediate 13 was used instead of intermediate 8, and thus 9.4 g of a pale yellow powder was obtained. The pale yellow powder was identified as compound HT10 by a FD-MS analysis.

Synthesis Example 11

Synthesis of Compound HT11

A reaction was carried out in the same manner as in Synthesis Example 1, except that bis(4-biphenylyl)amine was used instead of intermediate 8, and thus 8.7 g of a pale yellow powder was obtained. The pale yellow powder was identified as compound HT11 by a FD-MS analysis.

Synthesis Example 12

Synthesis of Compound HT12

A reaction was carried out in the same manner as in Synthesis Example 11, except that 2-bromo-9,9-dimethyl-7-[4-(2-naphthyl)phenyl]fluorene was used instead of intermediate 5, and thus 7.5 g of a pale yellow powder was obtained. The pale yellow powder was identified as compound HT12 by a FD-MS analysis.

Example 1-1

Production of Organic Electroluminescent Element

A glass substrate attached with an ITO transparent electrode (manufactured by Geomatec Co., Ltd.), having a size of 25 mm×75 mm×1.1 mm in thickness, was subjected to ultrasonic washing in isopropyl alcohol for 5 minutes, and then was subjected to UV-ozone washing for 30 minutes.

The transparent electrode line-attached glass substrate obtained after washing was mounted on a substrate holder of a vacuum deposition apparatus. First, a film of the compound HT1 (hereinafter, HT1 film) having a thickness of 80 nm was formed on the surface where the transparent electrode line was formed, such that the film of the compound HT1 covered the transparent electrode. The HT1 film functions as a hole injection layer and a hole transport layer.

A film of compound EM1 shown below was further formed by deposition to a thickness of 40 nm. At the same time, an amine compound D1 having styryl groups shown below was deposited as a light emitting molecule, such that the weight ratio of EM1 and D1 was 40:2. This film functions as a light emitting layer.

A film of Alq shown below was formed to be a thickness of 10 nm on the film that functions as a light emitting layer. This film functions as an electron injection layer. Subsequently, binary deposition was carried out using Li as a reducing dopant (Li source: manufactured by SAES Getters S.p.A.) and Alq, and thus an Alq:Li film (thickness 10 nm) was formed as an electron injection layer (cathode). Metal Al was deposited on this Alq:Li film, and thus a metal cathode was formed. Thus, an organic electroluminescent element was formed.

The organic electroluminescent element thus obtained was stored at 105° C. for 8 hours, and then the luminous efficiency was measured, while the emitted light color was observed. The luminous efficiency was determined by measuring the luminance using CS1000 manufactured by Konica Minolta Sensing, Inc. and calculating the luminous efficiency at 10 mA/cm$^2$. The results of measuring the half-life of light emission under DC constant current driving at an initial luminance of 5000 cd/m$^2$ and at room temperature are presented in Table 1.

[Chemical formula 29]

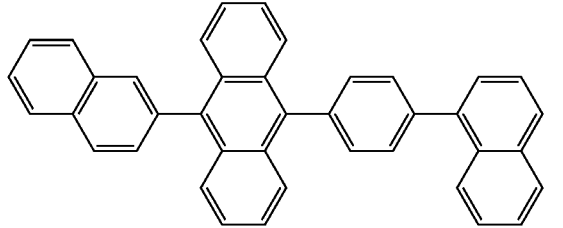

EM1

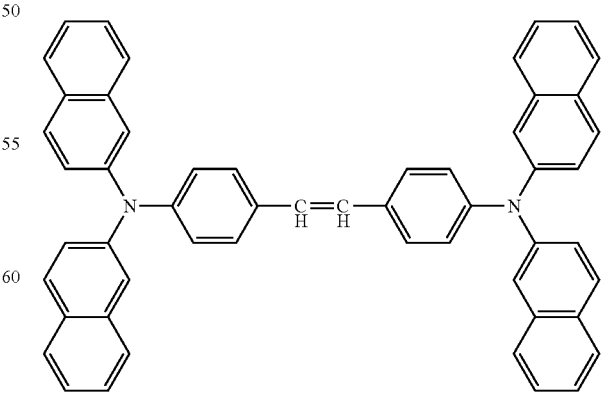

D1

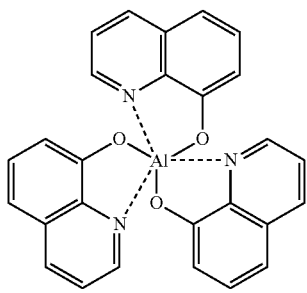

Alq

Examples 1-2 to 1-12

Production of Organic Electroluminescent Element

Organic electroluminescent elements were produced in the same manner as in Example 1-1, except that the compounds indicated in Table 1 were used instead of the compound HT1 as the hole transporting material. After the organic electroluminescent elements thus obtained were stored at 105° C. for 8 hours, the luminous efficiency was measured, and the emitted light color was observed. Furthermore, the results obtained by measuring the half-life of light emission under DC constant current driving at an initial luminance of 5000 cd/m² and at room temperature, are presented in Table 1.

Comparative Examples 1-1 to 1-3

Organic electroluminescent elements were produced in the same manner as in Example 1-1, except that comparative compounds 1 to 3 were used instead of the compound HT1 as the hole transporting material. After the organic electroluminescent elements thus obtained were stored at 105° C. for 8 hours, the luminous efficiency was measured, and the emitted light color was observed. Furthermore, the results obtained by measuring the half-life of light emission under DC constant current driving at an initial luminance of 5000 cd/m² and at room temperature, are presented in Table 1.

[Chemical formula 30]

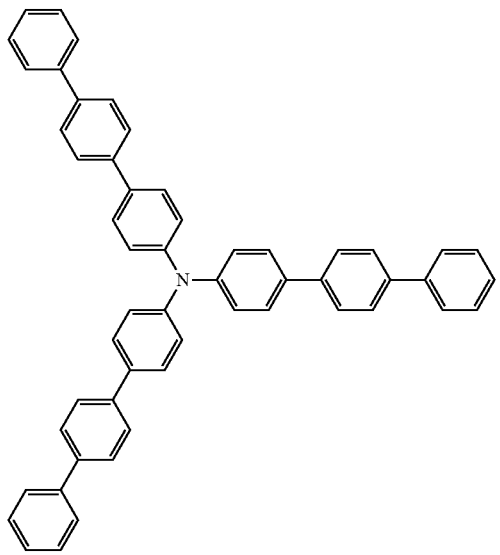

Comparative compound 1

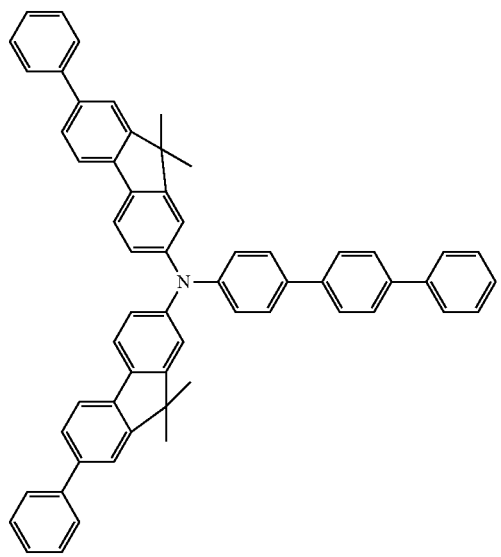

Comparative compound 2

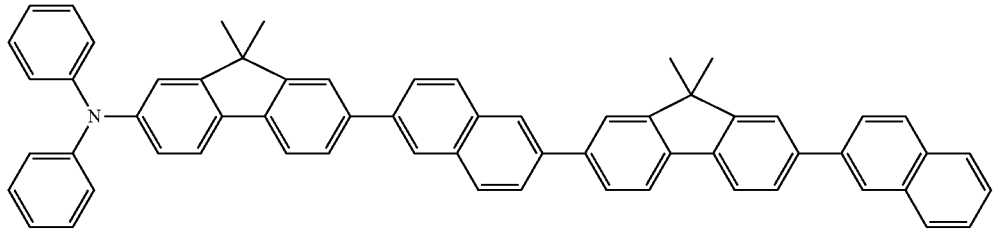

Comparative compound 3

Example 1-13

Production of Organic Electroluminescent Element

An organic electroluminescent element was produced in the same manner as in Example 1-1, except that the following arylamine compound D2 was used instead of the amine compound D1 having styryl groups. Me represents a methyl group. After the organic electroluminescent element thus obtained was stored at 105° C. for 8 hours, the luminous efficiency was measured, and the emitted light color was observed. Furthermore, the results obtained by measuring the half-life of light emission under DC constant current driving at an initial luminance of 5000 cd/m² and at room temperature, are presented in Table 1.

[Chemical formula 31]

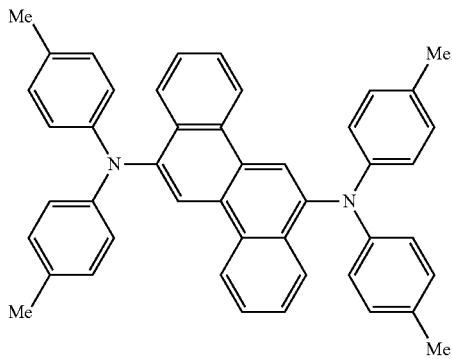

D2

Comparative Example 1-4

An organic electroluminescent element was produced in the same manner as in Example 1-13, except that the comparative compound 1 was used instead of the compound HT1 as the hole transporting material. After the organic electroluminescent element thus obtained was stored at 105° C. for 8 hours, the luminous efficiency was measured, and the emitted light color was observed. Furthermore, the results obtained by measuring the half-life of light emission under DC constant current driving at an initial luminance of 5000 cd/m² and at room temperature, are presented in Table 1.

TABLE 1

| | Hole transporting material | Luminous efficient (cd/A) | Emitted light color | Half-life (h) |
|---|---|---|---|---|
| Example 1-1 | HT 1 | 5.5 | Blue | 460 |
| Example 1-2 | HT 2 | 5.6 | Blue | 440 |
| Example 1-3 | HT 3 | 5.1 | Blue | 420 |
| Example 1-4 | HT 4 | 5.2 | Blue | 450 |
| Example 1-5 | HT 5 | 5.5 | Blue | 470 |
| Example 1-6 | HT 6 | 5.4 | Blue | 480 |
| Example 1-7 | HT 7 | 5.2 | Blue | 430 |
| Example 1-8 | HT 8 | 5.6 | Blue | 430 |
| Example 1-9 | HT 9 | 5.6 | Blue | 450 |
| Example 1-10 | HT 10 | 5.5 | Blue | 440 |
| Example 1-11 | HT 11 | 5.6 | Blue | 440 |
| Example 1-12 | HT 12 | 5.2 | Blue | 430 |
| Example 1-13 | HT 1 | 5.4 | Blue | 450 |
| Comparative Example 1-1 | Comparative compound 1 | 5.2 | Blue | 220 |
| Comparative Example 1-2 | Comparative compound 2 | 5.3 | Blue | 320 |
| Comparative Example 1-3 | Comparative compound 3 | 4.2 | Blue | 90 |
| Comparative Example 1-4 | Comparative compound 1 | 5.5 | Blue | 230 |

As can be seen from Table 1, the organic electroluminescent elements of Examples which use the aromatic amine derivatives of the present invention as the hole transporting material, maintain high luminous efficiency even if exposed to a high temperature environment, and have long emission lifetimes.

Example 2-1

Production of Organic Electroluminescent Element

A glass substrate attached with an ITO transparent electrode (manufactured by Geomatec Co., Ltd.), having a size of 25 mm×75 mm×1.1 mm in thickness, was subjected to ultrasonic washing in isopropyl alcohol for 5 minutes, and then was subjected to UV-ozone washing for 30 minutes.

The transparent electrode line-attached glass substrate obtained after washing was mounted on a substrate holder of a vacuum deposition apparatus. First, a film of the compound HT4 (hereinafter, HT4 film) having a thickness of 60 nm was formed on the surface where the transparent electrode line was formed, such that the HT4 film covered the transparent electrode. The HT4 film functions as a hole injection layer.

Compound TM1 shown below was deposited on this HT4 film, and thus a hole transport layer having a thickness of 20 nm was formed. Furthermore, the compound EM1 was deposited thereon, and thus a light emitting layer having a thickness of 40 nm was formed. At the same time, the amine compound D1 having styryl groups was deposited thereon as a light emitting molecule, such that the weight ratio of EM1 and D1 (EM1:D1) was 40:2. This film functions as a light emitting layer.

[Chemical formula 32]

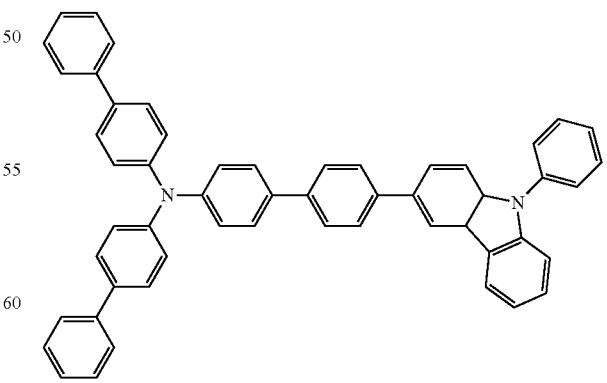

TM 1

A film of the organometallic complex (Alq) was formed to be a thickness of 10 nm on the film that functions as a light emitting layer. This film functions as an electron injection layer. Subsequently, binary deposition was carried out using Li as a reducing dopant (Li source: manufactured by SAES Getters S.p.A.) and Alq, and thus an Alq:Li film (thickness 10 nm) was formed as an electron injection layer (cathode). Metallic Al was deposited on this Alq:Li film, and thus a metal cathode was formed. Thus, an organic electroluminescent element was formed.

The organic electroluminescent element thus obtained was stored at 105° C. for 8 hours, and then the luminous efficiency was measured, and the emitted light color was observed. The luminous efficiency was determined by measuring the luminance using CS1000 manufactured by Konica Minolta Sensing, Inc. and calculating the luminous efficiency at 10 mA/cm$^2$. The results of measuring the half-life of light emission under DC constant current driving at an initial luminance of 5000 cd/m$^2$ and at room temperature are presented in Table 2.

Examples 2-2 and 2-3

Production of Organic Electroluminescent Element

Organic electroluminescent elements were produced in the same manner as in Example 2-1, except that the compounds indicated in Table 2 were used instead of the compound HT4 as the hole transporting material. After the organic electroluminescent elements thus obtained were stored at 105° C. for 8 hours, the luminous efficiency was measured, and the emitted light color was observed. Furthermore, the results obtained by measuring the half-life of light emission under DC constant current driving at an initial luminance of 5000 cd/m$^2$ and at room temperature, are presented in Table 2.

Example 2-4

Production of Organic Electroluminescent Element

An organic electroluminescent element was produced in the same manner as in Example 2-1, except that HT1 was used instead of the compound TM1 as the hole transporting material. After the organic electroluminescent element thus obtained was stored at 105° C. for 8 hours, the luminous efficiency was measured, and the emitted light color was observed. Furthermore, the results obtained by measuring the half-life of light emission under DC constant current driving at an initial luminance of 5000 cd/m$^2$ and at room temperature, are presented in Table 2.

Examples 2-5 to 2-21

Production of Organic Electroluminescent Elements

Organic electroluminescent elements were produced in the same manner as in Example 2-1, except that the compounds indicated in Table 2 were used as the hole injecting material and the hole transporting material. After the organic electroluminescent elements thus obtained were stored at 105° C. for 8 hours, the luminous efficiency was measured, and the emitted light color was observed. Furthermore, the results obtained by measuring the half-life of light emission under DC constant current driving at an initial luminance of 5000 cd/m$^2$ and at room temperature, are presented in Table 2.

Comparative Examples 2-1 to 2-3

Organic electroluminescent elements were produced in the same manner as in Example 2-1, except that the comparative compounds 1-3 were used instead of the compound HT4 as the hole injecting material. After the organic electroluminescent elements thus obtained were stored at 105° C. for 8 hours, the luminous efficiency was measured, and the emitted light color was observed. Furthermore, the results obtained by measuring the half-life of light emission under DC constant current driving at an initial luminance of 5000 cd/m$^2$ and at room temperature, are presented in Table 2.

TABLE 2

| | Hole injecting material | Hole transporting material | Driving voltage (V) | Emitted light color | Half-life (h) |
|---|---|---|---|---|---|
| Example 2-1 | HT4 | TM 1 | 6.9 | Blue | 470 |
| Example 2-2 | HT6 | TM 1 | 7.1 | Blue | 450 |
| Example 2-3 | HT8 | TM 1 | 6.9 | Blue | 480 |
| Example 2-4 | HT4 | HT 1 | 6.6 | Blue | 480 |
| Example 2-5 | HT4 | HT 2 | 6.7 | Blue | 460 |
| Example 2-6 | HT4 | HT 5 | 6.8 | Blue | 490 |
| Example 2-7 | HT4 | HT 7 | 6.7 | Blue | 450 |
| Example 2-8 | HT4 | HT 11 | 6.5 | Blue | 460 |
| Example 2-9 | HT6 | HT 1 | 6.8 | Blue | 470 |
| Example 2-10 | HT6 | HT 2 | 6.9 | Blue | 450 |
| Example 2-11 | HT6 | HT 5 | 7.0 | Blue | 480 |
| Example 2-12 | HT6 | HT 7 | 6.9 | Blue | 440 |
| Example 2-13 | HT6 | HT 11 | 6.7 | Blue | 450 |
| Example 2-14 | HT8 | HT 1 | 6.6 | Blue | 470 |
| Example 2-15 | HT8 | HT 2 | 6.6 | Blue | 470 |
| Example 2-16 | HT8 | HT 5 | 6.8 | Blue | 490 |
| Example 2-17 | HT8 | HT 7 | 6.8 | Blue | 460 |
| Example 2-18 | HT8 | HT 11 | 6.6 | Blue | 460 |
| Comparative Example 2-1 | Comparative compound 1 | TM 1 | 8.0 | Blue | 250 |
| Comparative Example 2-2 | Comparative compound 2 | TM 1 | 7.3 | Blue | 320 |
| Comparative Example 2-3 | Comparative compound 3 | TM 1 | 7.8 | Blue | 150 |

As can be seen from Table 2, the organic electroluminescent elements of Examples which use the aromatic amine derivatives of the present invention as the hole injecting material, have low driving voltages and have long emission lifetimes.

The present patent application claims priority based on Japanese Patent Application No. JP2009-068306 filed in the Japanese Patent Office on Mar. 19, 2009, the contents of which are incorporated herein by reference.

INDUSTRIAL APPLICABILITY

The aromatic amine derivative of the present invention is suitable as a material for constructing organic electroluminescent elements.

The invention claimed is:
1. An organic electroluminescent element containing an organic thin film layer composed of plural layers including at least a light emitting layer and a hole transport layer, the organic thin film layer being between a cathode and an anode, and the hole transport layer contains an aromatic amine derivative represented by the following formula (1):

wherein Ar$_1$ represents an organic group A represented by the following formula (2) or (2-2);

Ar$_2$ represents the organic group A, or an organic group B represented by the following formula (3);

Ar$_3$ represents the organic group A, the organic group B, or an organic group C represented by the following formula (3-2);

when two or more of Ar$_1$ to Ar$_3$ each represent the organic group A, the two or more organic groups A may be identical or different;

when two of Ar$_1$ to Ar$_3$ each represent the organic group B, the two organic groups B may be identical or different;

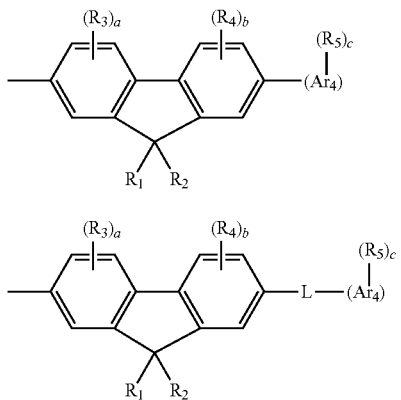

wherein Ar$_4$ represents a substituted or unsubstituted fused-ring group having 10 to 14 ring-forming carbon atoms selected from the group consisting of a 1-naphthyl group, a 2-naphthyl group, a 1-phenanthryl group, a 2-phenanthryl group, a 3-phenanthryl group, and a 9-phenanthryl group;

R$_1$ to R$_5$ each independently represent a hydrogen atom, a linear, branched or cyclic alkyl group having 1 to 10 carbon atoms, or an aryl group having 6 to 12 ring-forming carbon atoms;

L represents a substituted or unsubstituted arylene group having 6 to 10 ring-forming carbon atoms;

a, b and c each independently represent an integer from 0 to 2;

two of R$_3$, R$_4$ and R$_5$ may be joined together to form an unsaturated ring structure; and when a, b or c is 2, R$_3$ and R$_3$, R$_4$ and R$_4$ or R$_5$ and R$_5$ may be joined together to form an unsaturated ring structure;

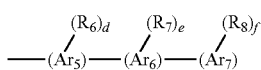

wherein Ar$_5$ and Ar$_6$ each independently represent a substituted or unsubstituted arylene group having 6 to 14 ring-forming carbon atoms;

Ar$_7$ represents a single bond, or a substituted or unsubstituted arylene group having 6 to 14 ring-forming carbon atoms;

R$_6$ to R$_8$ each independently represent a hydrogen atom, a linear, branched or cyclic alkyl group having 1 to 10 carbon atoms, or an aryl group having 6 to 12 ring-forming carbon atoms;

d, e and f each independently represent an integer from 0 to 2;

two of R$_6$, R$_7$ and R$_8$ may be joined together to form an unsaturated ring structure; and when d, e or f is 2, R$_6$ and R$_6$, R$_7$ and R$_7$, or R$_8$ and R$_8$ may be joined together to form an unsaturated ring structure; and

wherein Ar$_8$ represents a substituted or unsubstituted arylene group having 10 to 14 ring-forming carbon atoms;

R$_{11}$ represents a hydrogen atom, a linear, branched or cyclic alkyl group having 1 to 10 carbon atoms, or an aryl group having 6 to 12 ring-forming carbon atoms; and g represents an integer from 0 to 2.

2. An organic electroluminescent element containing an organic thin film layer composed of plural layers including at least a light emitting layer and plural hole transport layers, the organic thin film layer being between a cathode and an anode, and one of the hole transport layers which is in direct contact with the light emitting layer contains an aromatic amine derivative represented by the following formula (1):

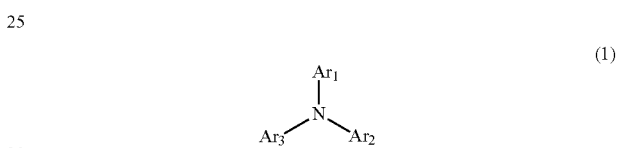

wherein Ar$_1$ represents an organic group A represented by the following formula (2) or (2-2);

Ar$_2$ represents the organic group A, or an organic group B represented by the following formula (3);

Ar$_3$ represents the organic group A, the organic group B, or an organic group C represented by the following formula (3-2);

when two or more of Ar$_1$ to Ar$_3$ each represent the organic group A, the two or more organic groups A may be identical or different;

when two of Ar$_1$ to Ar$_3$ each represent the organic group B, the two organic groups B may be identical or different;

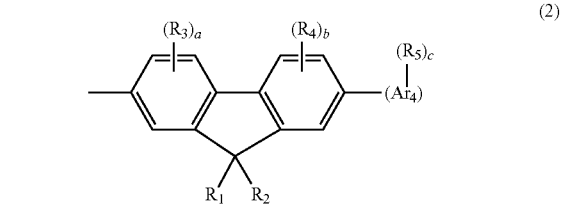

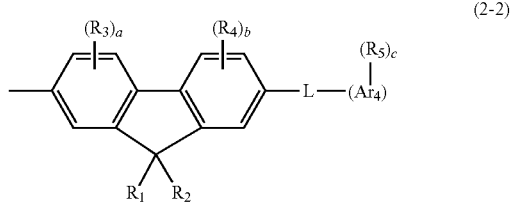

wherein Ar$_4$ represents a substituted or unsubstituted fused-ring group having 10 to 14 ring-forming carbon atoms selected from the group consisting of a 1-naphthyl group, a 2-naphthyl group, a 1-phenanthryl group, a 2-phenanthryl group, a 3-phenanthryl group, and a 9-phenanthryl group;

$R_1$ to $R_5$ each independently represent a hydrogen atom, a linear, branched or cyclic alkyl group having 1 to 10 carbon atoms, or an aryl group having 6 to 12 ring-forming carbon atoms;

L represents a substituted or unsubstituted arylene group having 6 to 10 ring-forming carbon atoms;

a, b and c each independently represent an integer from 0 to 2;

two of $R_3$, $R_4$, and $R_5$ may be joined together to form an unsaturated ring structure; and when a, b or c is 2, $R_3$ and $R_3$, $R_4$ and $R_4$, or $R_5$ and $R_5$ may be joined together to form an unsaturated ring structure;

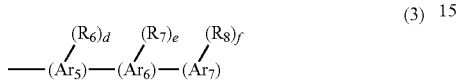

(3)

wherein $Ar_5$ and $Ar_6$ each independently represent a substituted or unsubstituted arylene group having 6 to 14 ring-forming carbon atoms;

$Ar_7$ represents a single bond, or a substituted or unsubstituted arylene group having 6 to 14 ring-forming carbon atoms;

$R_6$ to $R_8$ each independently represent a hydrogen atom, a linear, branched or cyclic alkyl group having 1 to 10 carbon atoms, or an aryl group having 6 to 12 ring-forming carbon atoms;

d, e and f each independently represent an integer from 0 to 2;

two of $R_6$, $R_7$ and $R_8$ may be joined together to form an unsaturated ring structure; and when d, e or f is 2, $R_6$ and $R_6$, $R_7$ and $R_7$, or $R_8$ and $R_8$ may be joined together to form an unsaturated ring structure; and

(3-2)

wherein $Ar_8$ represents a substituted or unsubstituted arylene group having 10 to 14 ring-forming carbon atoms;

$R_{11}$ represents a hydrogen atom, a linear, branched or cyclic alkyl group having 1 to 10 carbon atoms, or an aryl group having 6 to 12 ring-forming carbon atoms; and g represents an integer from 0 to 2.

3. An organic electroluminescent element containing an organic thin film layer composed of plural layers including at least a light emitting layer and a hole injection layer, the organic thin film layer being between a cathode and an anode, and the hole injection layer contains an aromatic amine derivative represented by the following formula (1):

(1)

wherein $Ar_1$ represents an organic group A represented by the following formula (2) or (2-2);

$Ar_2$ represents the organic group A, or the organic group B represented by the following formula (3);

$Ar_3$ represents the organic group A, the organic group B, or an organic group C represented by the following formula (3-2);

when two or more of $Ar_1$ to $Ar_3$ each represent the organic group A, the two or more organic groups A may be identical or different;

when two of $Ar_1$ to $Ar_3$ each represent the organic group B, the two organic groups B may be identical or different;

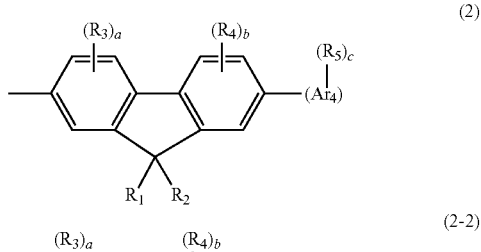

(2)

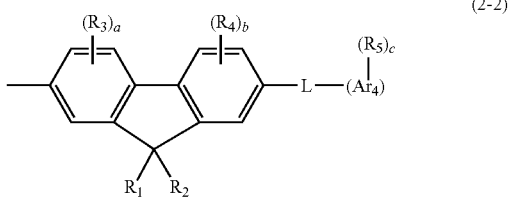

(2-2)

wherein $Ar_4$ represents a substituted or unsubstituted fused-ring group having 10 to 14 ring-forming carbon atoms selected from the group consisting of a 1-naphthyl group, a 2-naphthyl group, a 1-phenanthryl group, a 2-phenanthryl group, a 3-phenanthryl group, and a 9-phenanthryl group;

$R_1$ to $R_5$ each independently represent a hydrogen atom, a linear, branched or cyclic alkyl group having 1 to 10 carbon atoms, or an aryl group having 6 to 12 ring-forming carbon atoms;

L represents a substituted or unsubstituted arylene group having 6 to 10 ring-forming carbon atoms;

a, b and c each independently represent an integer from 0 to 2;

two of $R_3$, $R_4$, and $R_5$ may be joined together to form an unsaturated ring structure; and when a, b or c is 2, $R_3$ and $R_3$, $R_4$ and $R_4$, or $R_5$ and $R_5$ may be joined together to form an unsaturated ring structure;

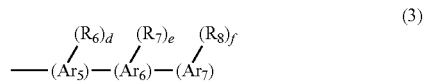

(3)

wherein $Ar_5$ and $Ar_6$ each independently represent a substituted or unsubstituted arylene group having 6 to 14 ring-forming carbon atoms;

$Ar_7$ represents a single bond, or a substituted or unsubstituted arylene group having 6 to 14 ring-forming carbon atoms;

$R_6$ to $R_8$ each independently represent a hydrogen atom, a linear, branched or cyclic alkyl group having 1 to 10 carbon atoms, or an aryl group having 6 to 12 ring-forming carbon atoms;

d, e and f each independently represent an integer from 0 to 2;

two of $R_6$, $R_7$ and $R_8$ may be joined together to form an unsaturated ring structure; and when d, e or f is 2, $R_6$ and $R_6$, $R_7$ and $R_7$, or $R_8$ and $R_8$ may be joined together to form an unsaturated ring structure; and

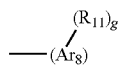
(3-2)

wherein $Ar_8$ represents a substituted or unsubstituted arylene group having 10 to 14 ring-forming carbon atoms;

$R_{11}$ represents a hydrogen atom, a linear, branched or cyclic alkyl group having 1 to 10 carbon atoms, or an aryl group having 6 to 12 ring-forming carbon atoms; and g represents an integer from 0 to 2.

4. An organic electroluminescent element containing an organic thin film layer composed of plural layers including at least a light emitting layer and plural hole injection layers, the organic thin film layer being between a cathode and an anode, and one of the hole injection layers which is in direct contact with the anode contains an aromatic amine derivative represented by the following formula (1):

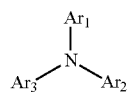
(1)

wherein $Ar_1$ represents an organic group A represented by the following formula (2) or (2-2);

$Ar_2$ represents the organic group A, or an organic group B represented by the following formula (3);

$Ar_3$ represents the organic group A, the organic group B, or an organic group C represented by the following formula (3-2);

when two or more of $Ar_1$ to $Ar_3$ each represent the organic group A, the two or more organic groups A may be identical or different;

when two of $Ar_1$ to $Ar_3$ each represent the organic group B, the two organic groups B may be identical or different;

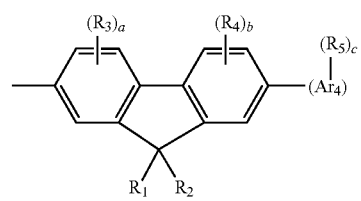
(2)

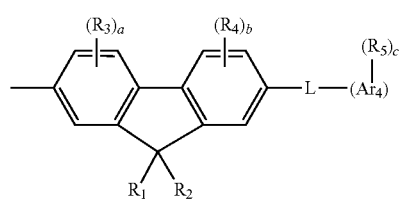
(2-2)

wherein $Ar_4$ represents a substituted or unsubstituted fused-ring group having 10 to 14 ring-forming carbon atoms selected from the group consisting of a 1-naphthyl group, a 2-naphthyl group, a 1-phenanthryl group, a 2-phenanthryl group, a 3-phenanthryl group, and a 9-phenanthryl group;

$R_1$ to $R_5$ each independently represent a hydrogen atom, a linear, branched or cyclic alkyl group having 1 to 10 carbon atoms, or an aryl group having 6 to 12 ring-forming carbon atoms;

L represents a substituted or unsubstituted arylene group having 6 to 10 ring-forming carbon atoms;

a, b and c each independently represent an integer from 0 to 2;

two of $R_3$, $R_4$, and $R_5$ may be joined together to form an unsaturated ring structure; and when a, b or c is 2, $R_3$ and $R_3$, $R_4$ and $R_4$, or $R_5$ and $R_5$ may be joined together to form an unsaturated ring structure;

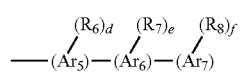
(3)

wherein $Ar_5$ and $Ar_6$ each independently represent a substituted or unsubstituted arylene group having 6 to 14 ring-forming carbon atoms;

$Ar_7$ represents a single bond, or a substituted or unsubstituted arylene group having 6 to 14 ring-forming carbon atoms;

$R_6$ to $R_8$ each independently represent a hydrogen atom, a linear, branched or cyclic alkyl group having 1 to 10 carbon atoms, or an aryl group having 6 to 12 ring-forming carbon atoms;

d, e and f each independently represent an integer from 0 to 2;

two of $R_6$, $R_7$ and $R_8$ may be joined together to form an unsaturated ring structure; and when d, e or f is 2, $R_6$ and $R_6$, $R_7$ and $R_7$, or $R_8$ and $R_8$ may be joined together to form an unsaturated ring structure; and

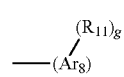
(3-2)

wherein $Ar_8$ represents a substituted or unsubstituted arylene group having 10 to 14 ring-forming carbon atoms;

$R_{11}$ represents a hydrogen atom, a linear, branched or cyclic alkyl group having 1 to 10 carbon atoms, or an aryl group having 6 to 12 ring-forming carbon atoms; and g represents an integer from 0 to 2.

* * * * *